United States Patent
Hardy et al.

(10) Patent No.: US 7,473,682 B2
(45) Date of Patent: Jan. 6, 2009

(54) ANGIOGENIC PEPTIDES AND USES THEREOF

(75) Inventors: Britta Hardy, Tel Aviv (IL); Alexander Battler, Ramat-HaSharon (IL); Annat Raiter, Kfar Saba (IL); Ran Kornowski, Ramat-HaSharon (IL); Chana Weiss, Givat Shmuel (IL)

(73) Assignee: Ramot at Tel Aviv University Ltd., Tel-Aviv (IL)

( * ) Notice: Subject to any disclaimer, the term of this patent is extended or adjusted under 35 U.S.C. 154(b) by 0 days.

(21) Appl. No.: 10/577,679

(22) PCT Filed: Oct. 28, 2004

(86) PCT No.: PCT/IL2004/000992

§ 371 (c)(1),
(2), (4) Date: Apr. 28, 2006

(87) PCT Pub. No.: WO2005/039616

PCT Pub. Date: May 6, 2005

(65) Prior Publication Data

US 2007/0082849 A1    Apr. 12, 2007

Related U.S. Application Data

(60) Provisional application No. 60/558,558, filed on Apr. 2, 2004, provisional application No. 60/514,895, filed on Oct. 29, 2003.

(51) Int. Cl.
A61K 38/10    (2006.01)
A61K 38/16    (2006.01)

(52) U.S. Cl. .......................................... 514/14; 514/2
(58) Field of Classification Search ...................... None
See application file for complete search history.

(56) References Cited

U.S. PATENT DOCUMENTS 6,638,911 B1 * 10/2003 Blaschuk et al. ............. 514/15

2005/0112168 A1 * 5/2005 Puzas .......................... 424/423

FOREIGN PATENT DOCUMENTS

| EP | 1136082 | 9/2001 |
|----|---------|--------|
| WO | WO 02/02593 | 1/2002 |
| WO | WO 03/037172 | 8/2003 |

OTHER PUBLICATIONS

Zhang et al., Cancer Letters, 2001, v171, 153-164.*
Balian, WO 03/072593, 2003, pp. 1-22 with 1-9 of figures/drawings.*
Puzas "Human TRAP Peptide SEQ ID No. 24", Database Geneseq 'Online!, Database Accession No. ABR44764, 2003. Abstract.
Bainbridge et al. "A Peptide Encoded by Exon 6 of VEGF (EG3306) Inhibits VEGF-IncludedAngiogenesis In Vitro and Ischaemic Retinal Neovascularisation In Vivo", Biochemidal and Biophysical Research Communications, 302: 793-799, 2003.
Conway et al. "Molecular Mechanisms of Blood Vessel Growth", Cardiovascular Research, 49: 507-521, 2001.
Giordano et al. "Biopanning and Rapid Analysis of Selective Interactive Ligands",Nature Medicine, 11(7), 1249-1253, 2001.
Hetian et al.. "A Novel Peptide Isolated from a Phage Display Library Inhibits Tumor Growth and Metastasis by Blocking the Binding of Vascular Endothelial Growth Factor to its Kinase Domain Receptor", The Journal of Biological Chemistry, 277(45): 43137-43142, 200 2.
Liu et al. "Combinataorial Peptide Library Methods for Immunobiology Research", Experimental Hematology, 31: 11-30, 2003.
Puzas "Human TRAP Peptide SEQ ID No. 24", Database Geneseq 'Online!, Database Accession No. ABR44764, 2003. Abstract.
Ramarao "Human Sperm Activator Peptide (Husap), Sperm 5 Pro.", Database Geneseq 'Online!, Database Accession No. AAE32981, 2003. Abstract.
Binétruy-Tournaire et al. "Identification of A Peptide Blocking Vascular Endothelial Growth Factor (VEGF)-Mediated Angiogenesis", The EMBO Journal, 19(7): 1525-1533, 2000.

* cited by examiner

*Primary Examiner*—Anish Gupta
*Assistant Examiner*—Ronald T Niebauer

(57) ABSTRACT

A peptide comprising an amino acid sequence as set forth in SEQ ID NO: 2, 4, 6, 8, 10 or 12 is provided. The peptide being at least 6 and no more than 50 amino acid residues in length. Also provided are therapeutic applications using such peptides.

12 Claims, 39 Drawing Sheets
(39 of 39 Drawing Sheet(s) Filed in Color)

Figures 6a-i

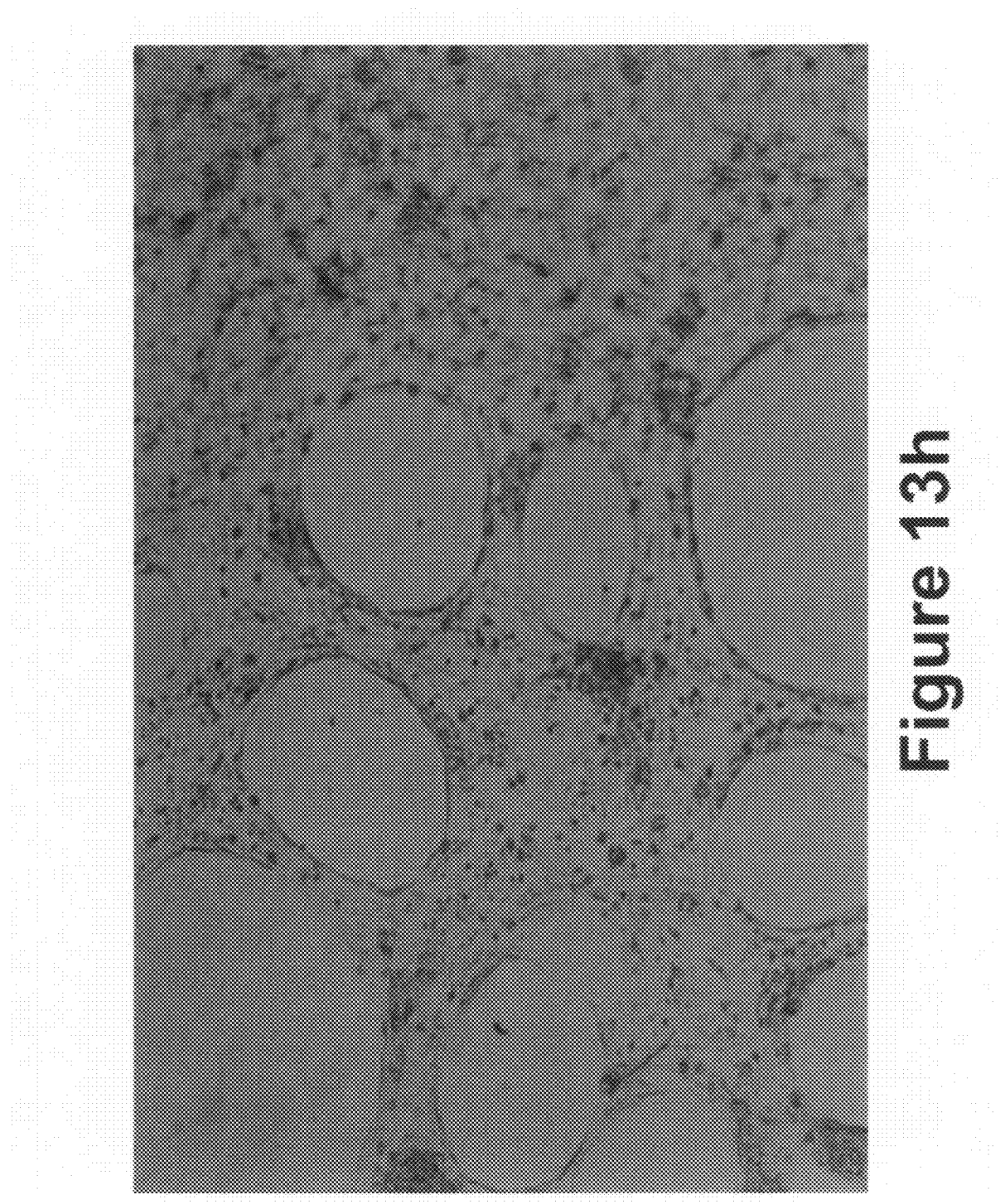

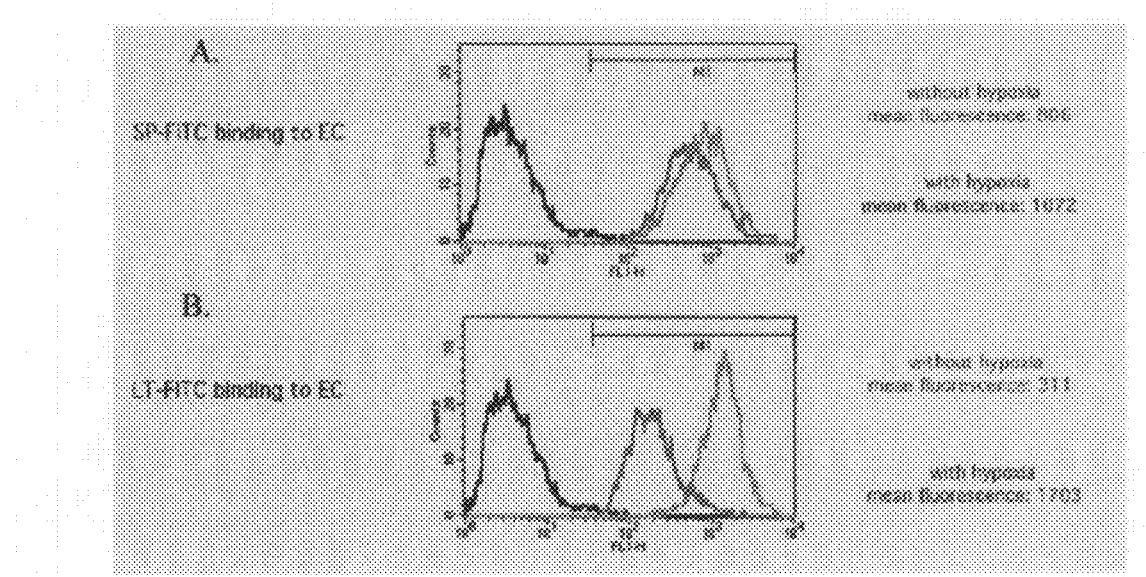
Figures 16a-b

Seq 1:  VPWMEPAYQRFL  (VL; SEQ ID NO:2)
Seq 2:  LLADTTHHRPWT  (LT; SEQ ID NO:4)
Seq 3:  QPWLEQAYYSTF  (QF; SEQ ID NO:6)
Seq 4:  SAHGTSTGVPWP  (SP; SEQ ID NO:8)
Seq 5:  YPHIDSLGHWRR  (YR; SEQ ID NO:10)
Seq 6:  TLPWLEESYWRP  (TR; SEQ ID NO:12)

Figure 22a

Seq 1:  VPWMEPAYQRFL  (VL; SEQ ID NO:2)
Seq 3:  QPWLEQAYYSTF  (QF; SEQ ID NO:6)
Seq 5:  YPHIDSLGHWRR  (YR; SEQ ID NO:10)
Seq 6:  TLPWLEESYWRP  (TR; SEQ ID NO:12))

Motif scaned by e-motif
Hypertext Transfer Protocol://dna.stanford.edu/emotif/emotif-scan.dot.html
pw[ll][de].y (SEQ ID NO:27)
Pro Trp Xaa Xaa Xaa Xaa Tyr (SEQ ID NO:32)

Figure 22b

VEGF_MOUSE    Vascular endothelial growth factor B precursor
         PVSQFDGPSHQKKVV PWIDVY ARATCQPREVVVPLS  (amino acids 22-57 of SEQ ID NO:28)

PWIDVY   (SEQ ID NO:31 amino acids 37-42 of
SEQ ID NO:28)
PVSQFDGPSHQKKVVPWIDVYARATCQPREVVVPL Mouse (SEQ ID NO:29)
PVSQ D P HQ+KVV WIDVY RATCQPREVVVPL Alignment of VEGF-B
PVSQPDAPGHQRKVVSWIDVYTRATCQPREVVVPL Human (SEQ ID NO:30)
     Seq 1:  VPWMEPAYQRFL (SEQ ID NO:2)
     Seq 3:  QPWLEQAYYSTF (SEQ ID NO:6)
     Seq 5:  YPHIDSLGHWRR (SEQ ID NO:10)
     Seq 6:  TLPWLEESYWRP (SEQ ID NO:12)

Figure 22c

SEQUENCE LISTING

<160> NUMBER OF SEQ ID NOS: 32

<210> SEQ ID NO 1
<211> LENGTH: 36
<212> TYPE: DNA
<213> ORGANISM: Artificial sequence
<220> FEATURE:
<223> OTHER INFORMATION: Phage displayed peptide DNA sequence

<400> SEQUENCE: 1
gttccgtgga tggagccggc ttatcagagg tttctg                                 36

<210> SEQ ID NO 2
<211> LENGTH: 12
<212> TYPE: PRT
<213> ORGANISM: Artificial sequence
<220> FEATURE:
<223> OTHER INFORMATION: Phage displayed peptide

<400> SEQUENCE: 2

Val Pro Trp Met Glu Pro Ala Tyr Gln Arg Phe Leu
1               5                   10

<210> SEQ ID NO 3
<211> LENGTH: 36
<212> TYPE: DNA
<213> ORGANISM: Artificial sequence
<220> FEATURE:
<223> OTHER INFORMATION: Phage displayed peptide DNA sequence

<400> SEQUENCE: 3
ctgcttgcgg atacgacgca tcataggccg tggact                                 36

<210> SEQ ID NO 4
<211> LENGTH: 12
<212> TYPE: PRT
<213> ORGANISM: Artificial sequence
<220> FEATURE:
<223> OTHER INFORMATION: Phage displayed peptide

<400> SEQUENCE: 4

Leu Leu Ala Asp Thr Thr His His Arg Pro Trp Thr
1               5                   10

<210> SEQ ID NO 5
<211> LENGTH: 36
<212> TYPE: DNA
<213> ORGANISM: Artificial sequence
<220> FEATURE:
<223> OTHER INFORMATION: Phage displayed peptide DNA sequence

<400> SEQUENCE: 5
cagccttggt tggagcaggc ttattatagt acgttt                              36

<210> SEQ ID NO 6
<211> LENGTH: 12
<212> TYPE: PRT
<213> ORGANISM: Artificial sequence
<220> FEATURE:
<223> OTHER INFORMATION: Phage displayed peptide

<400> SEQUENCE: 6

Gln Pro Trp Leu Glu Gln Ala Tyr Tyr Ser Thr Phe
1               5                   10

<210> SEQ ID NO 7
<211> LENGTH: 36
<212> TYPE: DNA
<213> ORGANISM: Artificial sequence
<220> FEATURE:
<223> OTHER INFORMATION: Phage displayed peptide DNA sequence

<400> SEQUENCE: 7
tctgcgcatg ggacgtctac tggtgttccg tggccg                              36

<210> SEQ ID NO 8
<211> LENGTH: 12
<212> TYPE: PRT
<213> ORGANISM: Artificial sequence
<220> FEATURE:
<223> OTHER INFORMATION: Phage displayed peptide

<400> SEQUENCE: 8

Ser Ala His Gly Thr Ser Thr Gly Val Pro Trp Pro
1               5                   10

<210> SEQ ID NO 9
<211> LENGTH: 36
<212> TYPE: DNA
<213> ORGANISM: Artificial sequence
<220> FEATURE:
<223> OTHER INFORMATION: Phage displayed peptide DNA sequence

<400> SEQUENCE: 9
tatccgcata ttgattcgct tggtcattgg cggcgg                              36

<210> SEQ ID NO 10
<211> LENGTH: 12
<212> TYPE: PRT
<213> ORGANISM: Artificial sequence
<220> FEATURE:
<223> OTHER INFORMATION: Phage displayed peptide

<400> SEQUENCE: 10

Tyr Pro His Ile Asp Ser Leu Gly His Trp Arg Arg
1               5                   10

<210> SEQ ID NO 11
<211> LENGTH: 36
<212> TYPE: DNA
<213> ORGANISM: Artificial sequence
<220> FEATURE:
<223> OTHER INFORMATION: Phage displayed peptide DNA sequence

<400> SEQUENCE: 11
actttgccgt ggctggagga gtcttattgg cgtcct                              36

```
<210> SEQ ID NO 12
<211> LENGTH: 12
<212> TYPE: PRT
<213> ORGANISM: Artificial sequence
<220> FEATURE:
<223> OTHER INFORMATION: Phage displayed peptide

<400> SEQUENCE: 12

Thr Leu Pro Trp Leu Glu Glu Ser Tyr Trp Arg Pro
1               5                   10

<210> SEQ ID NO 13
<211> LENGTH: 6
<212> TYPE: PRT
<213> ORGANISM: Artificial sequence
<220> FEATURE:
<223> OTHER INFORMATION: Consensus motif derived from integration of
      biologically active phage displayed peptides
<220> FEATURE:
<221> NAME/KEY: misc_feature
<222> LOCATION: (3)..(3)
<223> OTHER INFORMATION: Leucine or Isoleucine
<220> FEATURE:
<221> NAME/KEY: misc_feature
<222> LOCATION: (4)..(4)
<223> OTHER INFORMATION: Aspartate or Glutamate
<220> FEATURE:
<221> NAME/KEY: misc_feature
<222> LOCATION: (5)..(5)
<223> OTHER INFORMATION: Xaa can be any naturally occurring amino acid

<400> SEQUENCE: 13

Pro Trp Xaa Xaa Xaa Tyr
1               5

<210> SEQ ID NO 14
<211> LENGTH: 5
<212> TYPE: PRT
<213> ORGANISM: Artificial sequence
<220> FEATURE:
<223> OTHER INFORMATION: Synthetic peptide

<400> SEQUENCE: 14

Val Pro Trp Leu Glu
1               5

<210> SEQ ID NO 15
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 15
ctacctccac catgccaagt g                                                   21

<210> SEQ ID NO 16
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 16
tgcgctgata gacatccatg a                                                   21

<210> SEQ ID NO 17
<211> LENGTH: 20
<212> TYPE: DNA
```

```
<213> ORGANISM: Artificial sequence
<220> FEATURE:
<223> OTHER INFORMATION: Single strand DNA oligonucleotide

<400> SEQUENCE: 17
ttcctgccga tgcatgtcta                                              20

<210> SEQ ID NO 18
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 18
tgttcgctgc ctgacactgt                                              20

<210> SEQ ID NO 19
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 19
tcaggcagct cacagtccta gag                                          23

<210> SEQ ID NO 20
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 20
acttgtcgtc tgattctcca ggtt                                         24

<210> SEQ ID NO 21
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 21
tcagcgcatg gcaataatag a                                            21

<210> SEQ ID NO 22
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 22
accaaggtgc tagccatctt attc                                         24

<210> SEQ ID NO 23
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 23
agtgtaccct aactagccga ggaa                                         24
```

-continued

```
<210> SEQ ID NO 24
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 24
gcctgtgcag tgcaatacct t                                              21

<210> SEQ ID NO 25
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 25
gtcggagtca acggatttgg                                                20

<210> SEQ ID NO 26
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 26
ggcaacaata tccactttac cagagt                                         26

<210> SEQ ID NO 27
<211> LENGTH: 7
<212> TYPE: PRT
<213> ORGANISM: Artificial sequence
<220> FEATURE:
<223> OTHER INFORMATION: Consensus motif derived from integration of
      biologically active phage displayed peptides
<220> FEATURE:
<221> NAME/KEY: misc_feature
<222> LOCATION: (3)..(3)
<223> OTHER INFORMATION: Iso-leucine or Leucine
<220> FEATURE:
<221> NAME/KEY: misc_feature
<222> LOCATION: (4)..(4)
<223> OTHER INFORMATION: Aspartic or Glutamic acid
<220> FEATURE:
<221> NAME/KEY: misc_feature
<222> LOCATION: (5)..(6)
<223> OTHER INFORMATION: Any amino acid

<400> SEQUENCE: 27

Pro Trp Xaa Xaa Xaa Xaa Tyr
1               5

<210> SEQ ID NO 28
<211> LENGTH: 207
<212> TYPE: PRT
<213> ORGANISM: Mus musculus

<400> SEQUENCE: 28

Met Ser Pro Leu Leu Arg Arg Leu Leu Leu Val Ala Leu Leu Gln Leu
1               5                   10                  15

Ala Arg Thr Gln Ala Pro Val Ser Gln Phe Asp Gly Pro Ser His Gln
            20                  25                  30

Lys Lys Val Val Pro Trp Ile Asp Val Tyr Ala Arg Ala Thr Cys Gln
        35                  40                  45
```

```
Pro Arg Glu Val Val Pro Leu Ser Met Glu Leu Met Gly Asn Val
    50                  55                  60
Val Lys Gln Leu Val Pro Ser Cys Val Thr Val Gln Arg Cys Gly Gly
65                  70                  75                  80
Cys Cys Pro Asp Asp Gly Leu Glu Cys Val Pro Thr Gly Gln His Gln
                85                  90                  95
Val Arg Met Gln Ile Leu Met Ile Gln Tyr Pro Ser Ser Gln Leu Gly
            100                 105                 110
Glu Met Ser Leu Glu Glu His Ser Gln Cys Glu Cys Arg Pro Lys Lys
        115                 120                 125
Lys Glu Ser Ala Val Lys Pro Asp Arg Val Ala Ile Pro His His Arg
    130                 135                 140
Pro Gln Pro Arg Ser Val Pro Gly Trp Asp Ser Thr Pro Gly Ala Ser
145                 150                 155                 160
Ser Pro Ala Asp Ile Ile His Pro Thr Pro Ala Pro Gly Ser Ser Ala
                165                 170                 175
Arg Leu Ala Pro Ser Ala Val Asn Ala Leu Thr Pro Gly Pro Ala Ala
            180                 185                 190
Ala Ala Ala Asp Ala Ala Ala Ser Ser Ile Ala Lys Gly Gly Ala
        195                 200                 205

<210> SEQ ID NO 29
<211> LENGTH: 35
<212> TYPE: PRT
<213> ORGANISM: Mus musculus

<400> SEQUENCE: 29

Pro Val Ser Gln Phe Asp Gly Pro Ser His Gln Lys Lys Val Val Pro
1               5                   10                  15
Trp Ile Asp Val Tyr Ala Arg Ala Thr Cys Gln Pro Arg Glu Val Val
            20                  25                  30
Val Pro Leu
        35

<210> SEQ ID NO 30
<211> LENGTH: 35
<212> TYPE: PRT
<213> ORGANISM: Homo sapiens

<400> SEQUENCE: 30

Pro Val Ser Gln Pro Asp Ala Pro Gly His Gln Arg Lys Val Val Ser
1               5                   10                  15
Trp Ile Asp Val Tyr Thr Arg Ala Thr Cys Gln Pro Arg Glu Val Val
            20                  25                  30
Val Pro Leu
        35

<210> SEQ ID NO 31
<211> LENGTH: 6
<212> TYPE: PRT
<213> ORGANISM: Mus musculus

<400> SEQUENCE: 31

Pro Trp Ile Asp Val Tyr
1               5

<210> SEQ ID NO 32
<211> LENGTH: 7
```

```
<212> TYPE: PRT
<213> ORGANISM: Artificial sequence
<220> FEATURE:
<223> OTHER INFORMATION: Consensus motif derived from integration of
      biologically active phage displayed peptides
<220> FEATURE:
<221> NAME/KEY: misc_feature
<222> LOCATION: (3)..(6)
<223> OTHER INFORMATION: Any amino acid

<400> SEQUENCE: 32

Pro Trp Xaa Xaa Xaa Xaa Tyr
1               5
```

ANGIOGENIC PEPTIDES AND USES THEREOF

RELATED APPLICATIONS

This application is a National Phase Application of PCT Patent Application No. PCT/IL2004/000992 having International Filing Date of Oct. 28, 2004, which claims the benefit of U.S. Provisional Patent Application No. 60/514,895 filed on Oct. 29, 2003 and U.S. Provisional Patent Application No. 60/558,558 filed on Apr. 2, 2004. The contents of the above Applications are all incorporated herein by reference.

FIELD AND BACKGROUND OF THE INVENTION

The present invention relates to peptides that are capable of promoting angiogenesis and to the use thereof in the treatment of angiogenesis-dependent diseases, such as ischemic vascular diseases.

Angiogenesis is the process of generating new capillary blood vessels and involves an interplay between cells and soluble factors (1). In brief, activated endothelial cells migrate and proliferate to form new vessels, which are surrounded by layers of periendothelial cells; small blood vessels are surrounded by pericytes and large blood vessels are surrounded by smooth muscle cells.

Numerous factors regulate the angiogenic process. These include soluble factors and tissue oxygen. In the past two decades, a number of angiogenic molecules which positively regulate the angiogenic process were elucidated. These include Vascular Endothelium Growth Factor (VEGF), basic Fibroblast Growth Factor (bFGF), acidic FGF/FGF-1, hypoxia-inducible factor-1α (HIF-1α), and others (2). As mentioned, oxygen conditions also have important implications for the physiological and pathological angiogenic process (3). Under hypoxic conditions, VEGF gene expression is induced both in endothelial cells and pericytes to produce secretory forms of VEGF. VEGF, in turn, may bind to VEGF receptor-2 (Kdr) or VEGF receptor-1 (VEGFR-1; Flt-1) expressed on endothelial cells in an autocrine or paracrine manner, thereby causing proliferation of endothelial cells, which may lead to angiogenesis. Basal amounts of vascular VEGF synthesized under normoxia promote the maintenance of microvascular homeostasis (5). Expression of VEGF receptor 1 mRNA (Flt-1) was found to be up-regulated in peri-ischemic endothelial cells and in the infracted core of endothelial cells and periphery, with peak expression of VEGFR-1 in endothelial cells. Gene expression of VEGFR-1 is directly inducible by hypoxia, as in the case of VEGF. Twenty-four hours following hypoxia-induced VEGF gene expression, concurrent with the expression of the VEGFR-1 and 2 (Kdr) genes, endothelial cells begin to proliferate (6, 7).

Hypoxia-inducible gene products that participate in these cellular responses include erytropoietin, VEGF, and glycolytic enzymes (8). Hypoxia can directly enhance the expression of bFGF mRNA in pericytes. Increased expression of bFGF may play an important role in pericyte proliferation and in differentiation of pericytes and smooth muscle cells (9).

Angiogenesis-dependent diseases result when the angiogenic process is disregulated, resulting in excessive amounts of new blood vessels or an insufficient number of blood vessels. Insufficient angiogenesis is related to a large number of diseases and conditions, such as coronary artery diseases and delayed wound healing. To date, cardiovascular diseases are the leading cause of mortality in the United States, Europe, and Israel. In the United States, approximately one million deaths per year are attributed to cardiac causes, fifty percent of which are attributed to Coronary Artery Disease (CAD). The major morbidity from CAD is a result of obstructive coronary artery narrowing and the resultant myocardial ischemia CAD affects more than 13 million people, and its annual economic burden is in excess of sixty billion U.S. Dollars.

Mechanical revascularization of obstructive coronary stenoses by percutaneous techniques, including percutaneous transluminal angioplasty and stent implantation, is used to restore normal coronary artery blood flow. In addition, coronary artery occlusion bypass surgery is performed using arterial and venous conduits as grafts onto the coronary arterial tree. These treatment modalities have significant limitations in individuals with diffuse atherosclerotic disease or severe small vessel coronary artery disease, in diabetic patients, as well as in individuals who have already undergone surgical or percutaneous procedures.

For these reasons, therapeutic angiogenesis, aimed at stimulating new blood vessel growth, is highly desirable. The therapeutic concept of angiogenesis therapy is based on the premise that the existing potential for vascular growth inherent to vascular tissue can be utilized to promote the development of new blood vessels under the influence of the appropriate angiogenic molecules.

Therapeutic angiogenesis defines the intervention used to treat local hypovascularity by stimulating or inducing neovascularization for the treatment of ischemic vascular disease.

Animal studies have proven the feasibility of enhancing collateral perfusion and function via angiogenic compounds. Those experiments proved that exogenous administration of angiogenic growth factors or their genetic constructs could promote collateral vessel growth in experimental models of chronic ischemia. Although such studies demonstrated proof of concept, additional studies raise issues that still have not been resolved, such as the duration of exposure of the vessels to angiogenic factors and the brief half-lives of such proteins (10).

Synthetic peptides encompassing portions of proteins have become supportive tools for understanding the molecular mechanisms associated with protein biological functions. The use of short peptides constructed from specific regions of human FGF and VEGF that have the potential to efficiently agonize or antagonize the biological functions of the growth factor family members has been described (11). Several groups have reported the use of intact cells to screen a phage display peptide library to identify cell surface-binding peptides (12). A peptide-based ligand receptor map of the VEGF family was constructed by screening human endothelial cells stimulated with VEGF with a peptide library (13). Another study has described the screening of a 12-mer phage display peptide library on VEGF-2 receptor protein (14).

While reducing the present invention to practice, the present inventors used a 12-mer phage display peptide library to uncover peptides which are able to bind the cell-surface of endothelial cells incubated under normoxic or hypoxic conditions. Such peptides were shown to trigger angiogenic processes including endothelial cell-proliferation and vascularization. As such, these peptides can be used to treat various angiogenesis-dependent diseases, such as ischemic vascular diseases. Furthermore, characterization of the nature of endothelial cell signaling by these peptides will provide the

SUMMARY OF THE INVENTION

According to one aspect of the present invention there is provided peptide selected from the group consisting of SEQ ID NOs: 2, 4, 6, 8, 10, and 12.

According to another aspect of the present invention there is provided a peptide comprising an amino acid sequence selected from the group consisting of SEQ ID NOs: 2, 4, 6, 8, 10, and 12, the peptide being no more than 50 amino acid residues in length.

According to yet another aspect of the present invention there is provided a peptide comprising an amino acid sequence as set forth in SEQ ID NO:13, 27, or 32, the peptide being at least 6 and no more than 50 amino acid residues in length.

According to still another aspect of the present invention there is provided a composition-of-matter comprising at least two peptides, each independently selected from the group consisting of SEQ ID NOs: 2, 4, 6, 8, 10, and 12.

According to an additional aspect of the present invention there is provided a pharmaceutical composition comprising a therapeutically effective amount of a peptide having an amino acid sequence as set forth in SEQ ID NO:13, 27, or 32, the peptide being at least 6 and no more than 50 amino acid residues in length, and a pharmaceutically acceptable carrier or diluent.

According to yet an additional aspect of the present invention there is provided a pharmaceutical composition comprising a therapeutically effective amount of a peptide selected from the group consisting of SEQ ID NOs: 2, 4, 6, 8, 10, and 12 and a pharmaceutically acceptable carrier or diluent.

According to still an additional aspect of the present invention there is provided a pharmaceutical composition comprising a therapeutically effective amount of a peptide having an amino acid sequence selected from thee group consisting of SEQ ID NOs: 2, 4, 6, 8, 10, and 12, the peptide being no more than 50 amino acid residues in length, and a pharmaceutically acceptable carrier or diluent.

According to a further aspect of the present invention there is provided a method of promoting angiogenesis in a tissue of a subject, the method comprising providing to the subject a therapeutically effective amount of a peptide having an amino acid sequence as set forth in SEQ ID NO:13, 27, 32 the peptide being at least 6 and no more than 50 amino acid residues in length, to thereby promote angiogenesis in the subject.

According to further features in preferred embodiments of the invention described below, the peptide is selected from the group consisting of SEQ ID NOs:2, 6, and 12.

According to still further features in the described preferred embodiments the amino acid sequence is selected from the group consisting of SEQ ID NOs:2, 6, and 12.

According to still further features in the described preferred embodiments the peptide is a linear peptide or a cyclic peptide.

According to yet a further aspect of the present invention there is provided a method of promoting angiogenesis in a tissue of a subject, the method comprising providing to the subject a therapeutically effective amount of a peptide selected from the group consisting of SEQ ID NOs: 2, 4, 6, 8, 10, and 12, to thereby promote angiogenesis in the subject.

According to still a further aspect of the present invention there is provided a method of promoting angiogenesis in a tissue of a subject, the method comprising providing to the subject a therapeutically effective amount of a peptide having an amino acid sequence selected from the group consisting of SEQ ID NOs: 2, 4, 6, 8, 10, and 12, the peptide being no more than 50 amino acid residues in length, to thereby promote angiogenesis in the subject.

According to still further features in the described preferred embodiments the subject suffers from arteriosclerosis, retinopathy, remodeling disorder, von Hippel-Lindau syndrome, diabetes, and/or hereditary hemorrhagic telengiectasia.

According to still a further aspect of the present invention there is provided a nucleic acid construct comprising a polynucleotide sequence encoding the peptide of the present invention.

According to still further features in the described preferred embodiments the nucleic acid construct further comprises a promoter.

According to still a further aspect of the present invention there is provided a composition for targeting a drug to endothelial cells, the composition comprising the drug fused to a peptide having an amino acid sequence as set forth in SEQ ID NO:13, 27, or 32, the peptide being at least 6 and no more than 50 amino acid residues in length.

According to still further features in the described preferred embodiments the drug is selected from the group consisting of a toxin, a chemotherapeutic agent, and a radioisotope.

According to still a further aspect of the present invention there is provided a composition for targeting a drug to endothelial cells, the composition comprising the drug fused to a peptide selected from the group consisting of SEQ ID NOs: 2, 4, 6, 8, 10, and 12.

According to still a further aspect of the present invention there is provided a composition for targeting a drug to endothelial cells, the composition comprising the drug fused to a peptide having an amino acid sequence selected from the group consisting of SEQ ID NOs: 2, 4, 6, 8, 10, and 12, the peptide being no more than 50 amino acid residues in length.

According to still a further aspect of the present invention there is provided a method of identifying putative angiogenic molecules, the method comprising: (a) providing endothelial cells having peptides bound thereto, each of the peptides having an amino acid sequence selected from the group consisting of SEQ ID NOs: 2, 4, 6, 8, 10, and 12, the peptide being no more than 50 amino acid residues in length; and (b) identifying a molecule capable of displacing the peptides from the endothelial cells to thereby identify putative angiogenic molecules.

The present invention successfully addresses the shortcomings of the presently known configurations by providing peptides which are capable of promoting angiogenesis and as such can be used to treat angiogenesis-dependent diseases, such as ischemic vascular diseases.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The file of this patent contains at least one drawing executed in color photograph. Copies of this patent with color photograph(s) will be provided by the Patent and Trademark Office upon request and payment of necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

Figure 1A:
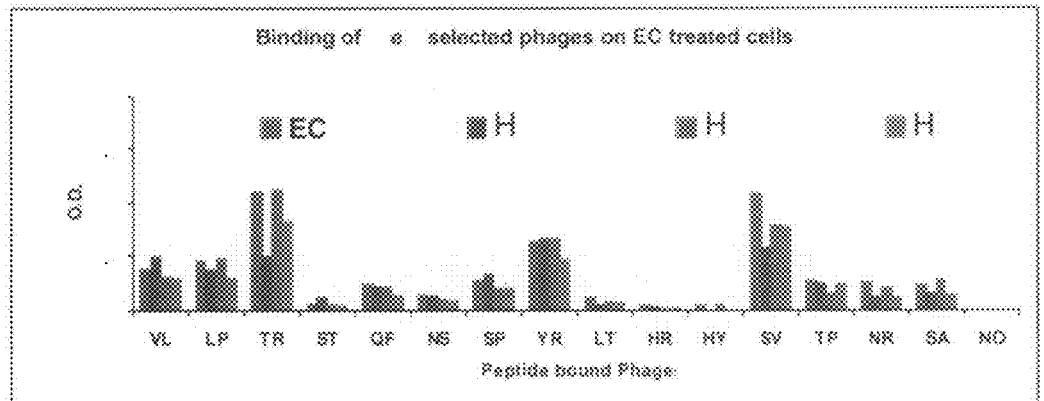
Figure 1B:
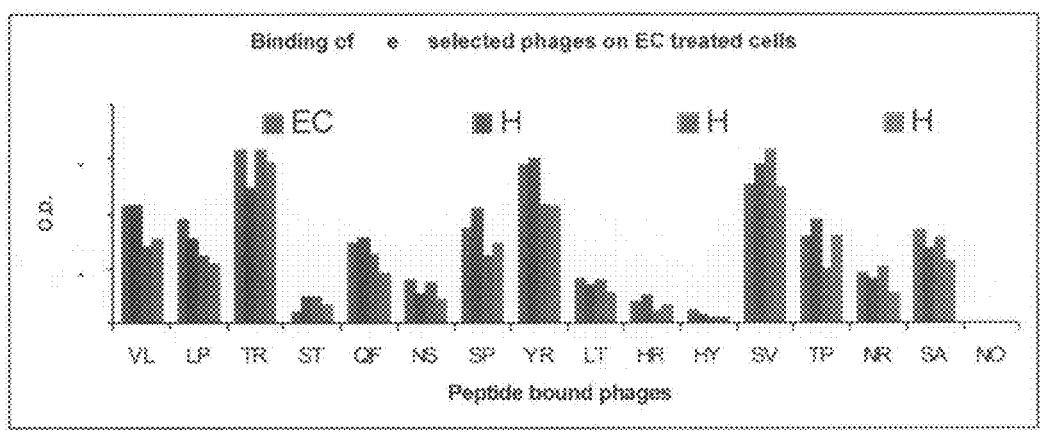

FIGS. 1a-b are bar graphs depicting the binding of peptide-presenting phages at a concentration of $10^9$ (FIG. 1a) or $10^{10}$ (FIG. 1b) phage per well, to ECs under normoxic conditions and following 3, 6, and 24 hours of hypoxia. The bars represent the binding to ECs of 15 different peptide-presenting phage (VL, LP, TR, ST, QF, NS, SP, YR, LT, HR, HY, SV, TP, NR, and SA) and the control (NO, unmodified M13 phage) following a 2-hour incubation. Absorbance at 450 nm, produced by anti-M13 HRP antibody, which detects peptide-presenting phages attached to ECs in the presence of tetramethyl benzidine liquid substrate, was measured using an ELISA reader.

Figure 2:
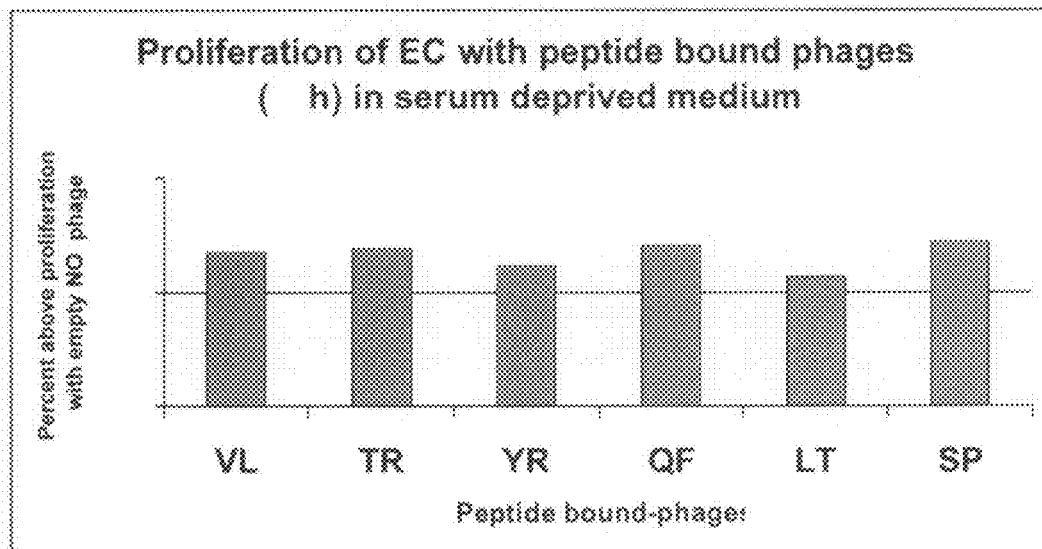

FIG. 2 is a bar graph depicting the effect of peptide-presenting phages on ECs proliferation. Six peptide-presenting phages (VL, TR, YR, QF, LT, SP) each at a concentration of $10^6$ were incubated with ECs in serum free media for 24 hours. Data was obtained by measuring radioactive [$^3$H]-Thymidine uptake into ECs (cpm/min) in the last 6 hours of incubation, and presented as a percent above ECs proliferation induced by control phages (NO, unmodified M13 phages).

Figure 3A:
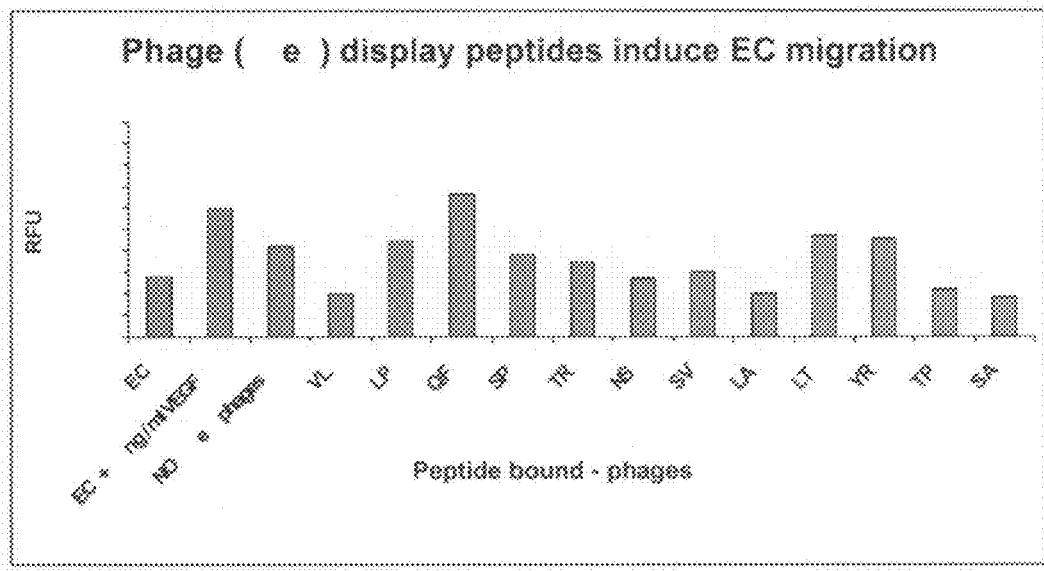
Figure 3B:
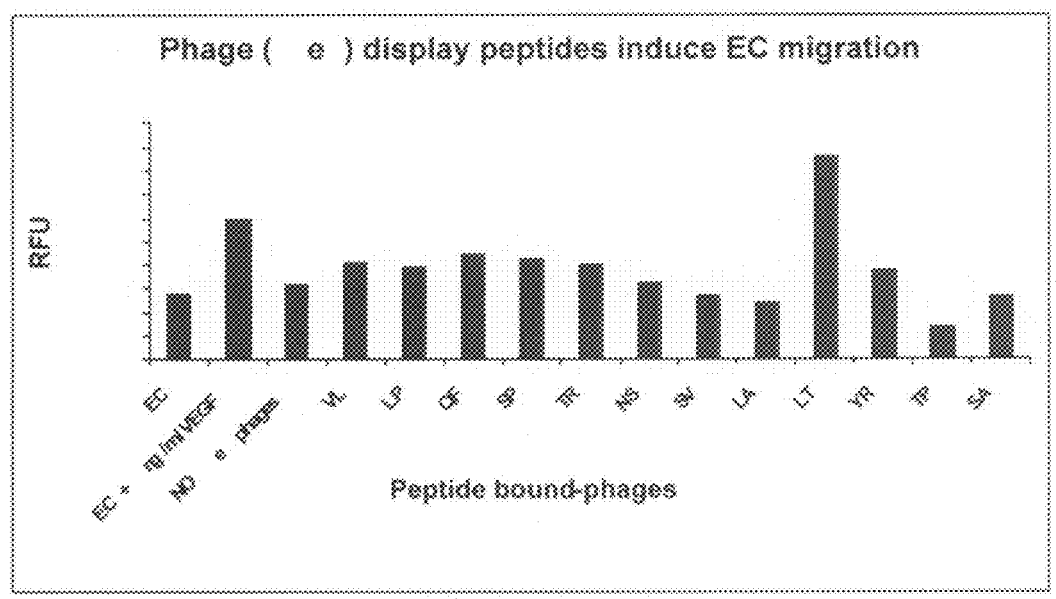

FIGS. 3a-b are bar graphs depicting the effect of direct activation of peptide-presenting phages on ECs migration. The migration of ECs was assayed in the presence of $10^5$ (FIG. 3a) or $10^6$ (FIG. 3b) peptide-presenting phages per well and was compared to negative (ECs, or ECs in the presence of NO phages—unmodified M13 phages) or positive (the angiogenic molecule—VEGF) control. The bars compare ECs migration induced by 12 peptide-presenting phages (VL, LP, QF, SP, TR, NS, SV, LA, LT, YR, TP and SA) following 5 hours of incubation in migration chambers. Data was obtained by measuring the fluorescent enhancement of the CyQuant GR dye molecular probe bound to cellular nucleic acid of lysed migratory cells using the Fluorescent ELISA reader at 480/520 nm and is expressed as Relative Fluorescence Units (RFU).

Figure 4A:
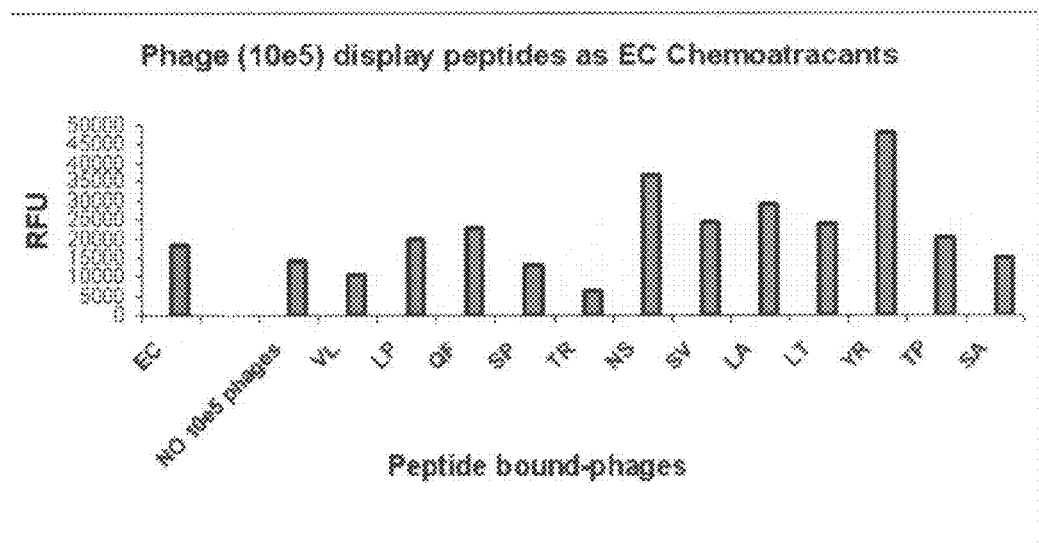
Figure 4B:
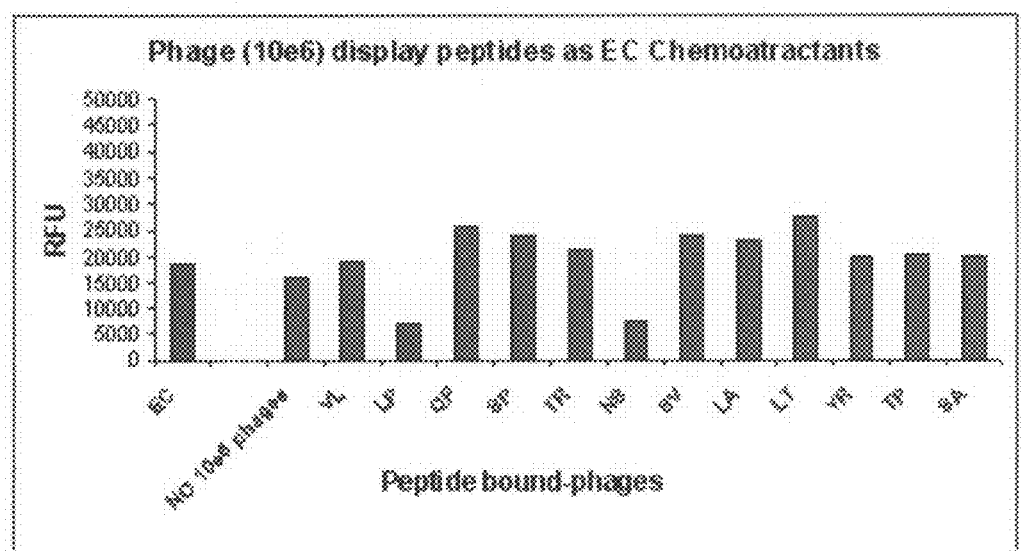

FIGS. 4a-b are bar graphs depicting chemo-attraction of ECs by peptide-presenting phages added to the feeder tray of the migration chamber. Peptide-presenting phages were used at a concentration of $10^5$ (FIG. 4a) or $10^6$ (FIG. 4b) phages per well and were compared to negative controls (ECs or ECs in the presence of NO phages—unmodified M13 phages). The bars compare ECs chemo-attraction induced by 12 peptide-presenting phages (VL, LP, QF, SP, TR, NS, SV, LA, LT, YR, TP and SA) following 5 hours of incubation in migration chamber. Data was obtained and presented as described for FIGS. 3a-b, hereinabove.

Figure 5:
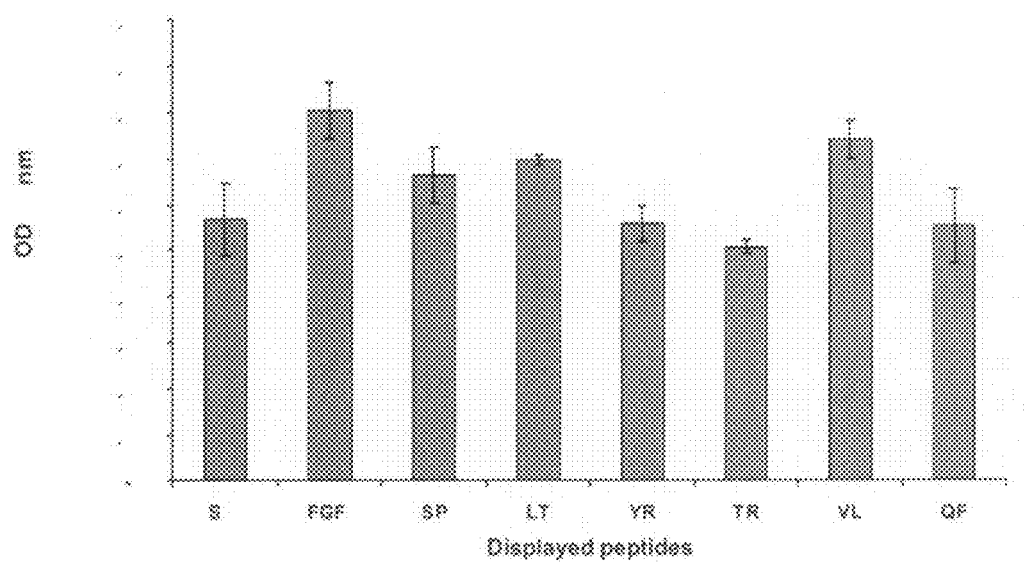

FIG. 5 is a bar graph depicting the proliferation of ECs in arterial rings in the presence of peptide-presenting phages ($10^6$) as compared with negative control (NO phage, unmodified M13 phages) and positive control (the angiogenic molecule-FGF). The bars compare ECs proliferation induced by six peptide-presenting phages (SP, LT, YR, TR, VL, and QF) following 7 days incubation in DMEM containing 10% FCS (37° C. with 5% $CO_2$). Data was obtained by an XTT assay (O.D. 450 nm).

Figure 6:
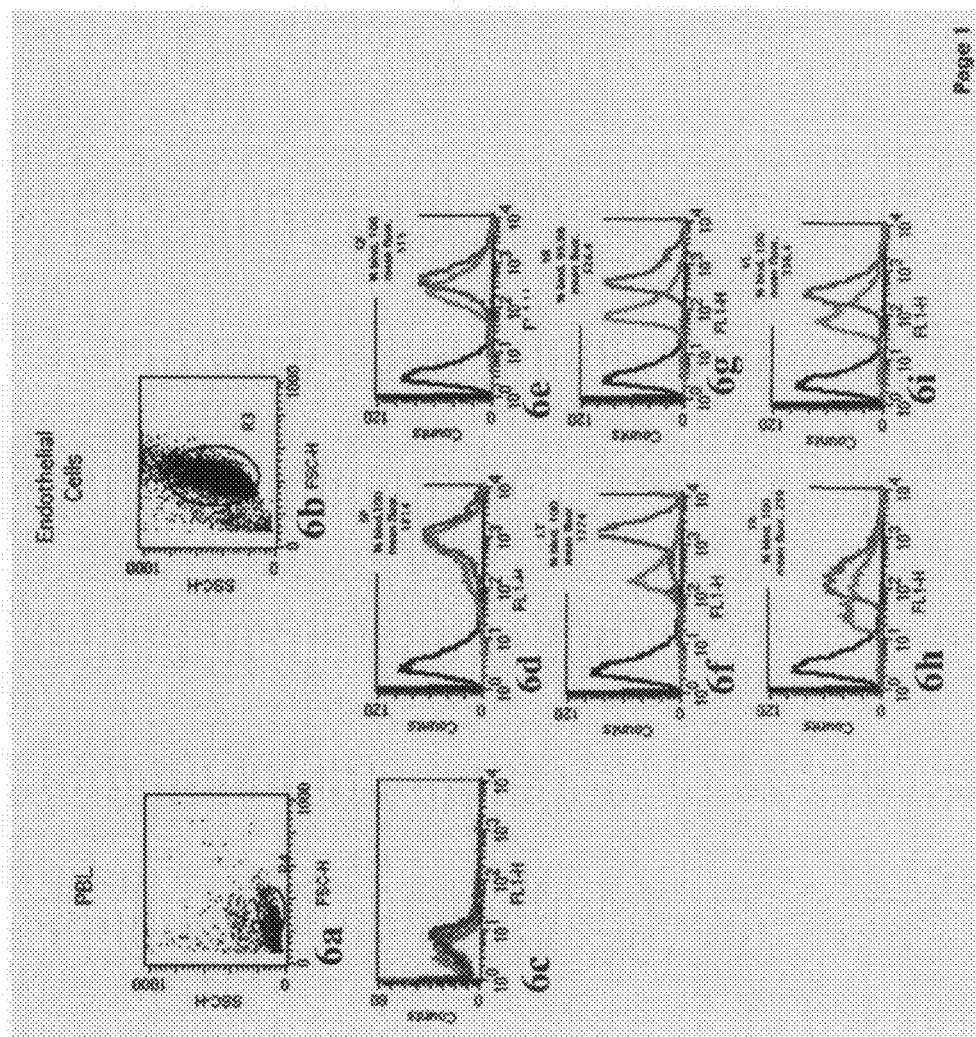

FIGS. 6a-i are graphs depicting the specific binding of synthetic peptides to Peripheral Blood Lymphocytes (PBL, FIG. 6a) or ECs (FIG. 6b-i). The graphs represent flow cytometry analysis of 100,000 cells incubated for 2 hours with 4 or 6 µg of synthetic peptides. FIGS. 6a-b are the results of flow cytometry analysis presenting the gates chosen either for (FIG. 6a) peripheral blood lymphocytes or for (FIG. 6b) endothelial cells analysis. The dots represent the dispersion of FITC labeled cells, according to their size (horizontal axis) versus their granulation (vertical axis). FIGS. 6c-i are the results of flow cytometry analysis presenting the percent binding to ECs and mean fluorescence of synthetic peptides: FIG. 6c—no peptide; FIG. 6d—SP; FIG. 6e—QF; FIG. 6f—LT; FIG. 6g—YR; FIG. 6h—TR; FIG. 6i—VL. The graphs represent flow cytometry analysis of $10^6$ ECs incubated for 2 hours with 4 µg of synthetic peptides (green line), 6 µg of synthetic peptides (red line), or isotype control (black line).

Figure 7:
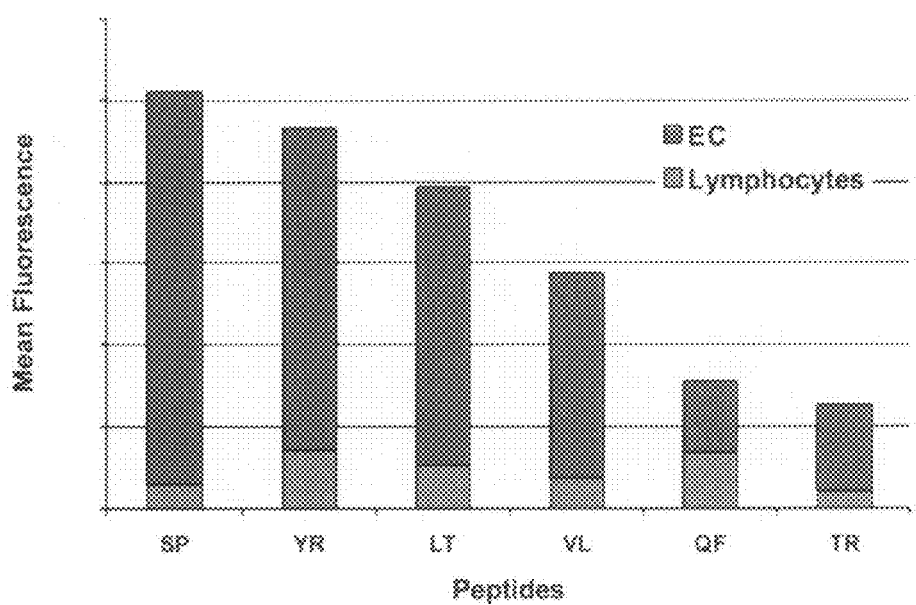

FIG. 7 is a bar graph demonstrating binding of synthetic peptides to PBL and ECs. The graph represents flow cytometry analysis of 5 µg FITC labeled synthetic peptide (SP, YR, LT, VL, QF and TR) bound to 100,000 PBLs and ECs. The bars compare mean fluorescence (emitted by the labeled synthetic peptides following 2 hours incubation with PBLs or ECs. Data was collected using FACS.

Figure 8A:
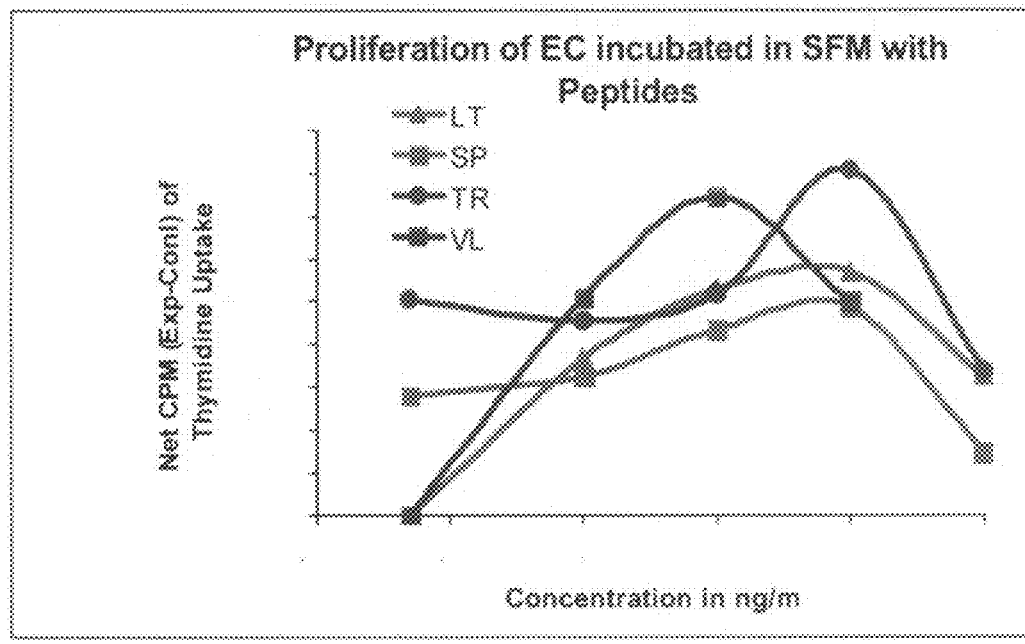
Figure 8B:
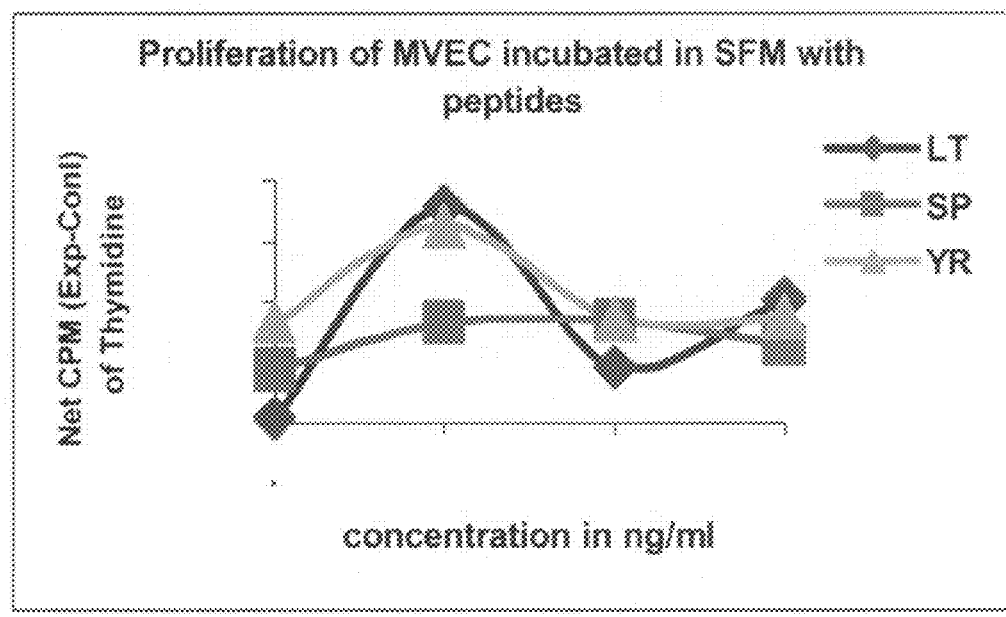

FIGS. 8a-b are graphs depicting the effect of synthetic peptides on cells proliferation. FIG. 8a illustrates the proliferation of ECs induced by LP, ST, TR, and VL at concentrations of 0.05, 0.1, 1, 10, and 100 ng/ml, following 24 hours incubation in EBM-2. FIG. 8b illustrates the proliferation of MVECs induced by LT SP, or YR at concentrations of 0.1, 1, 10, and 100 ng/ml following 24 hours incubation in EBM-MV. Results are expressed as [$^3$H]-Thymidine uptake by cells incubated with peptides minus control (cells incubated in EBM-2 and EBM-MV, respectively). Data was obtained by measuring radioactive [$^3$H]-Thymidine uptake into cells in a scintillation β counter by cpm/min in the last 6 hours of incubation.

Figure 9A:
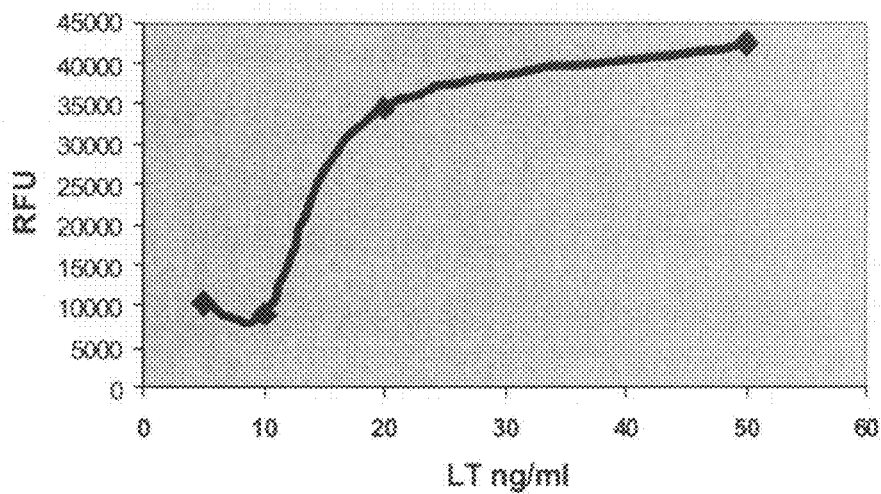
Figure 9B:
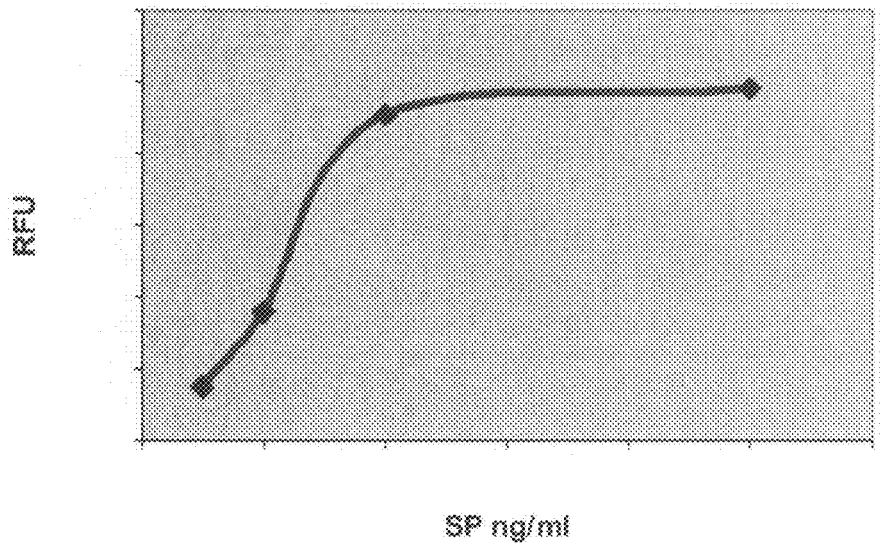
Figure 9C:
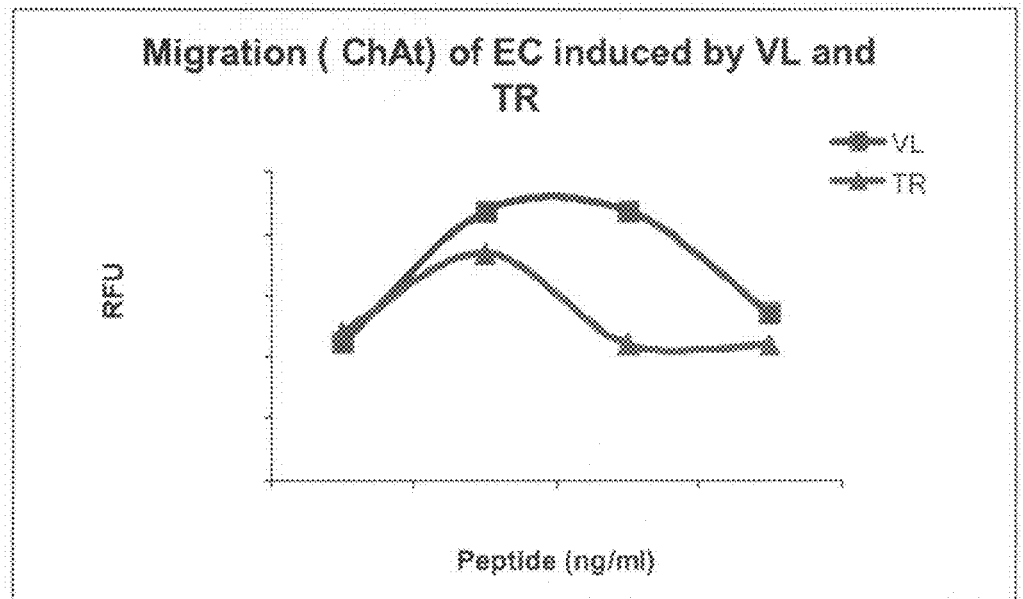

FIGS. 9a-c are graphs depicting the effect of the synthetic peptides on ECs migration. FIG. 9a-c are graphs illustrating the migration of ECs induced by LT (FIG. 9a), SP (FIG. 9b), or VL and TR (FIG. 9c) at concentrations of 5, 10, 20 and 50 ng/ml following 5 hours of incubation in migration chamber. Data was obtained and presented as described for FIGS. 3a-b, hereinabove.

Figure 10:
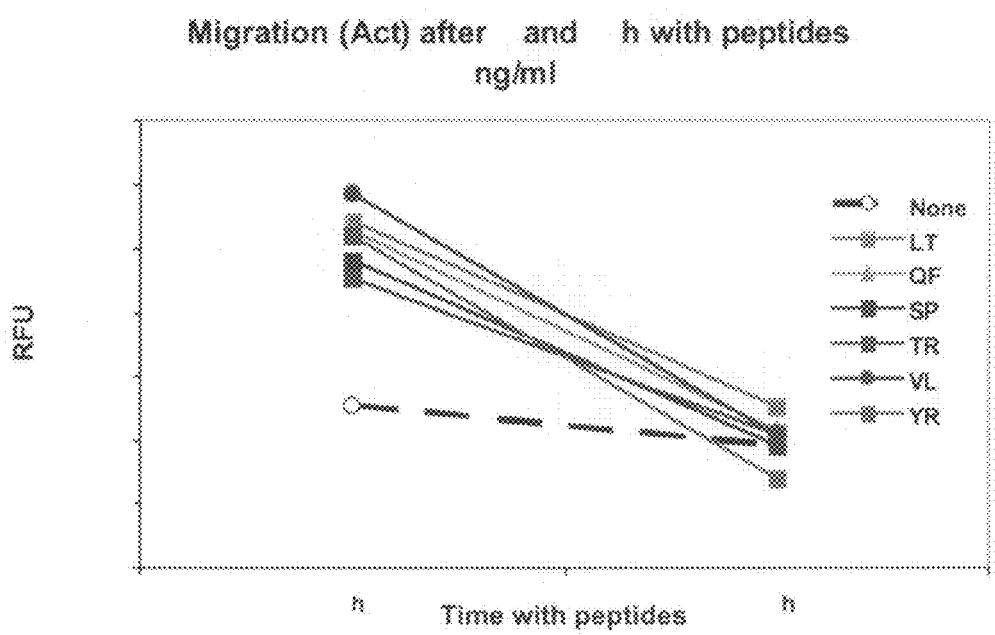

FIG. 10 is a graph depicting the time dependent effect of peptide incubation on ECs migration. The figure presents the migration of ECs as induced by 1 ng/ml synthetic peptide (LT, QF, SP, TR, VL and YR) following 5 and 15 hours of incubation in migration chamber. Data was obtained and presented as described for FIGS. 3a-b, hereinabove.

Figure 11A:
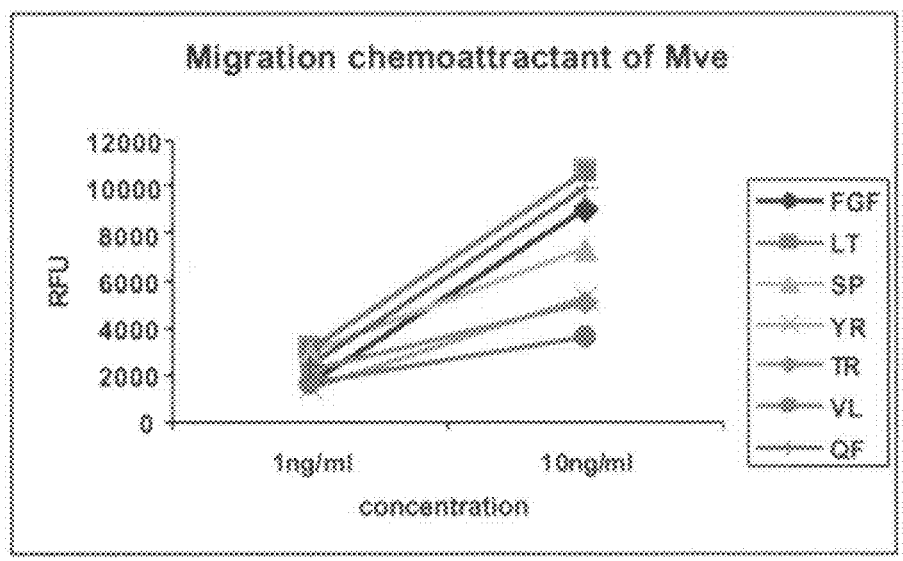
Figure 11B:
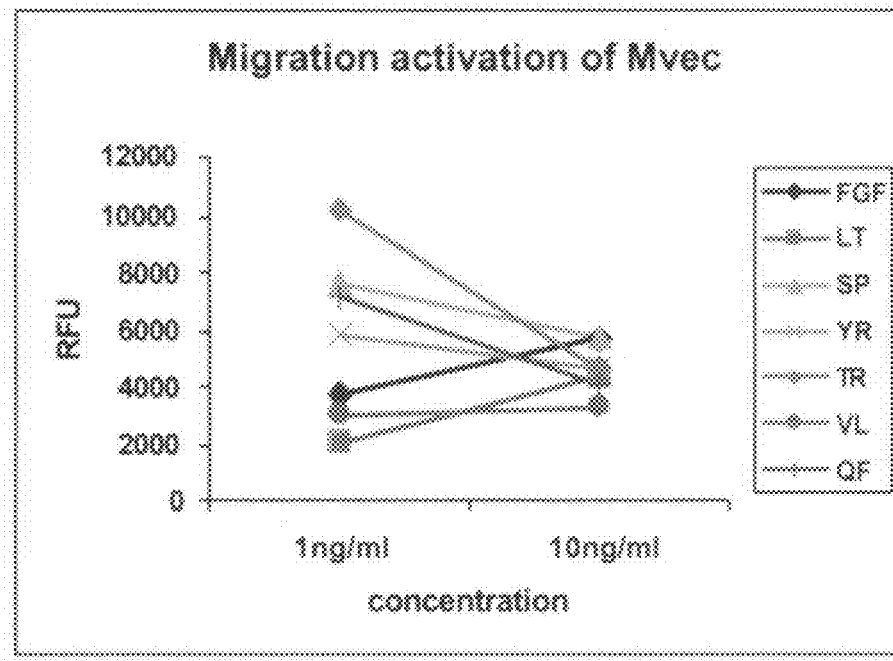

FIGS. 11a-b are graphs depicting effect of the synthetic peptides on MVECs migration. The graphs are illustrating the migration of MVECs (FIG. 11a) and migration activation of MVECs (FIG. 11b) induced by LT, SP, YR, TR, VL, QF and FGF at concentrations of 1 and 10 ng/ml, following 5 hours of incubation in migration chamber. Data was obtained and presented as described for FIGS. 3a-b, hereinabove.

Figure 12:
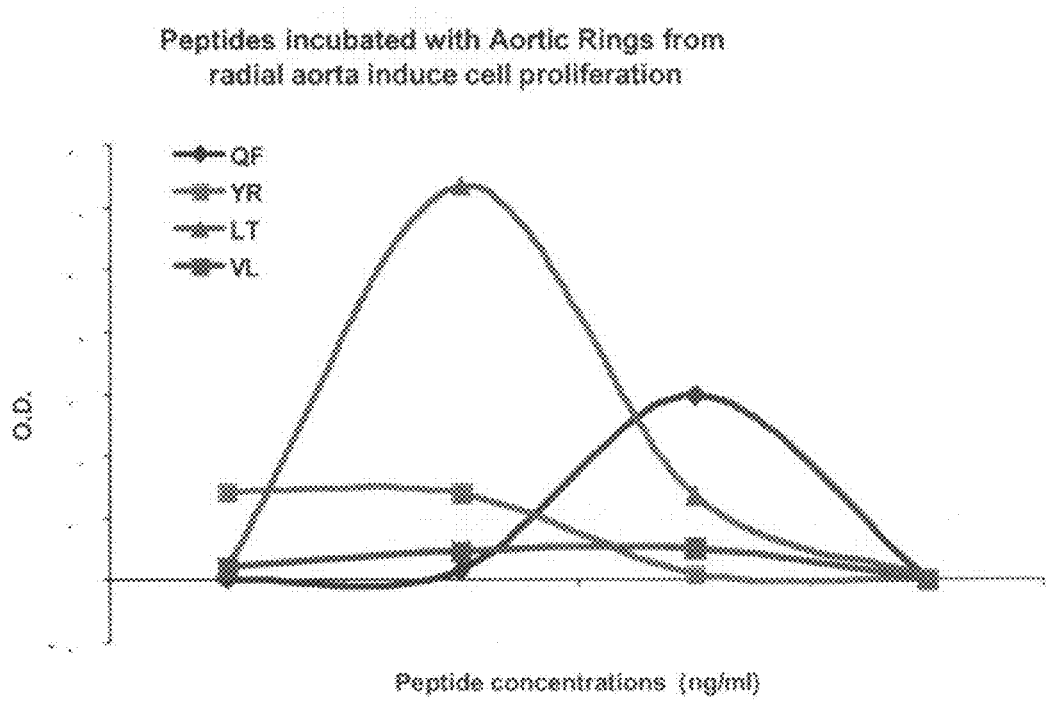

FIG. 12 is a graph depicting the effect of synthetic peptides on arterial ring sprouting. The graph presents the proliferation of ECs in arterial rings induced by four synthetic peptides (i.e., QF, YR, LT and VL) at concentrations 1, 10, 100 and 1000 ng/ml following 7 days incubation in DMEM containing 10% FCS (37° C. with 5% $CO_2$). Data was obtained by estimation of cell proliferation by an XTT assay (O.D. 450 mm).

Figure 13A:
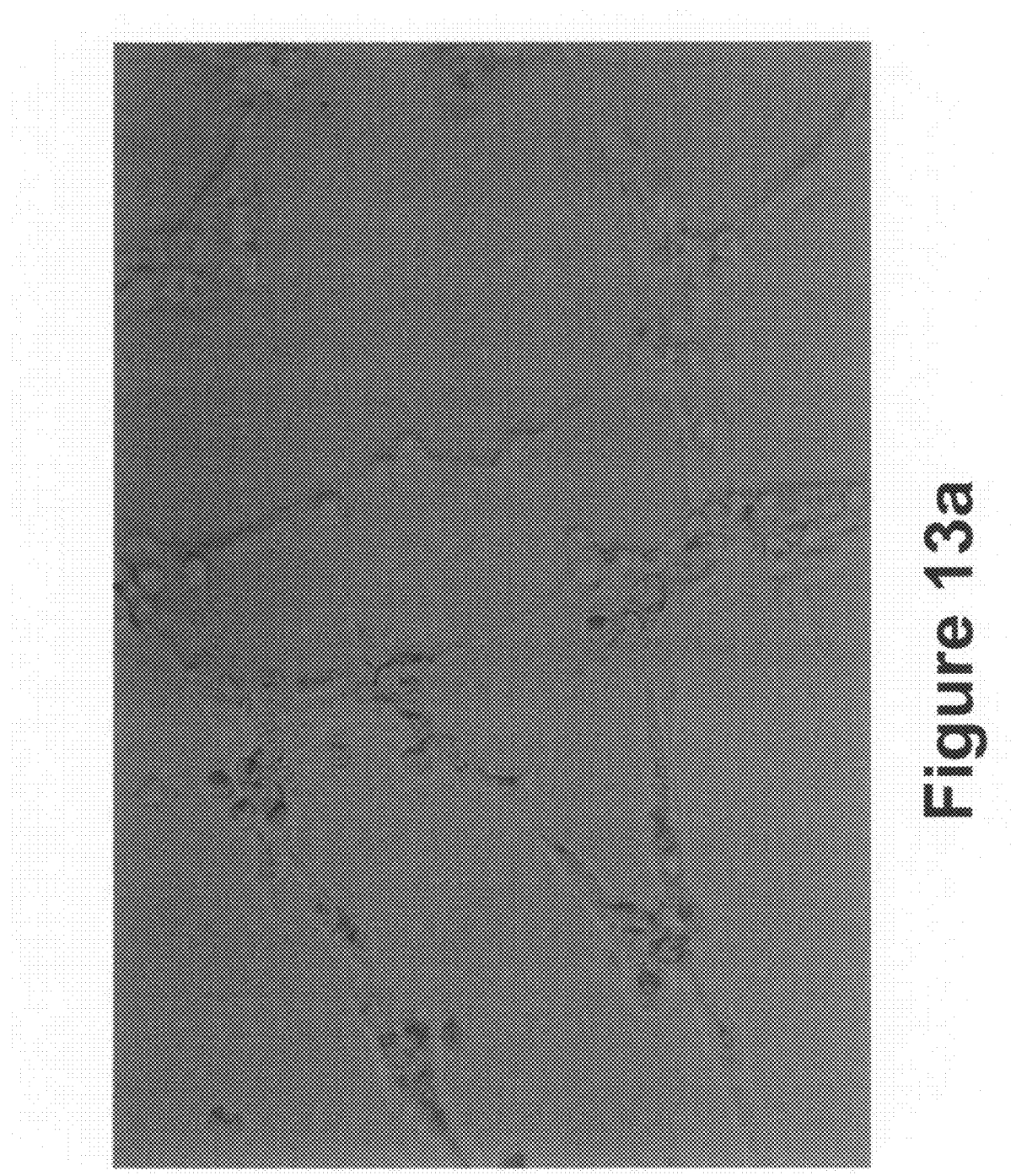
Figure 13B:
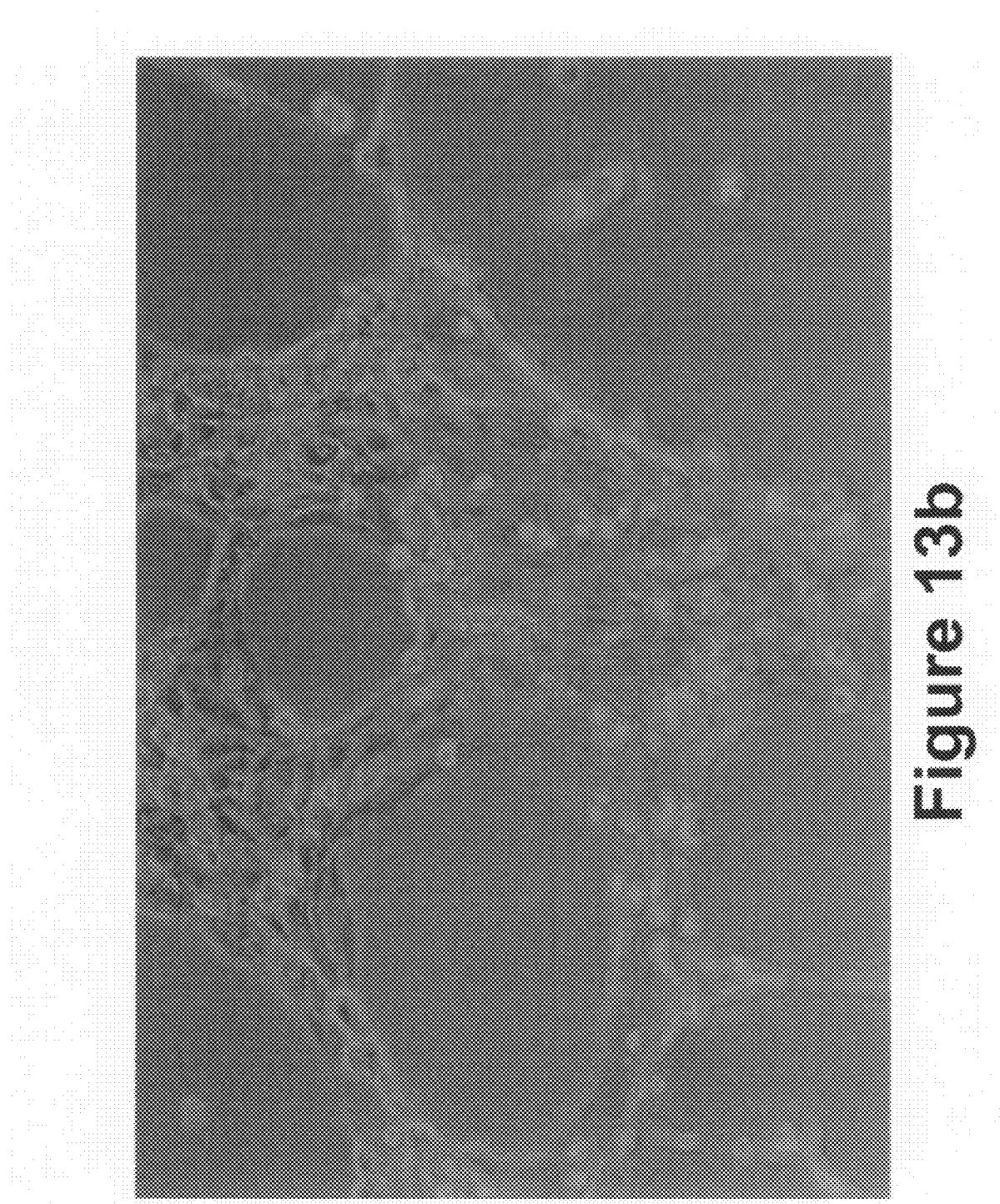
Figure 13C:
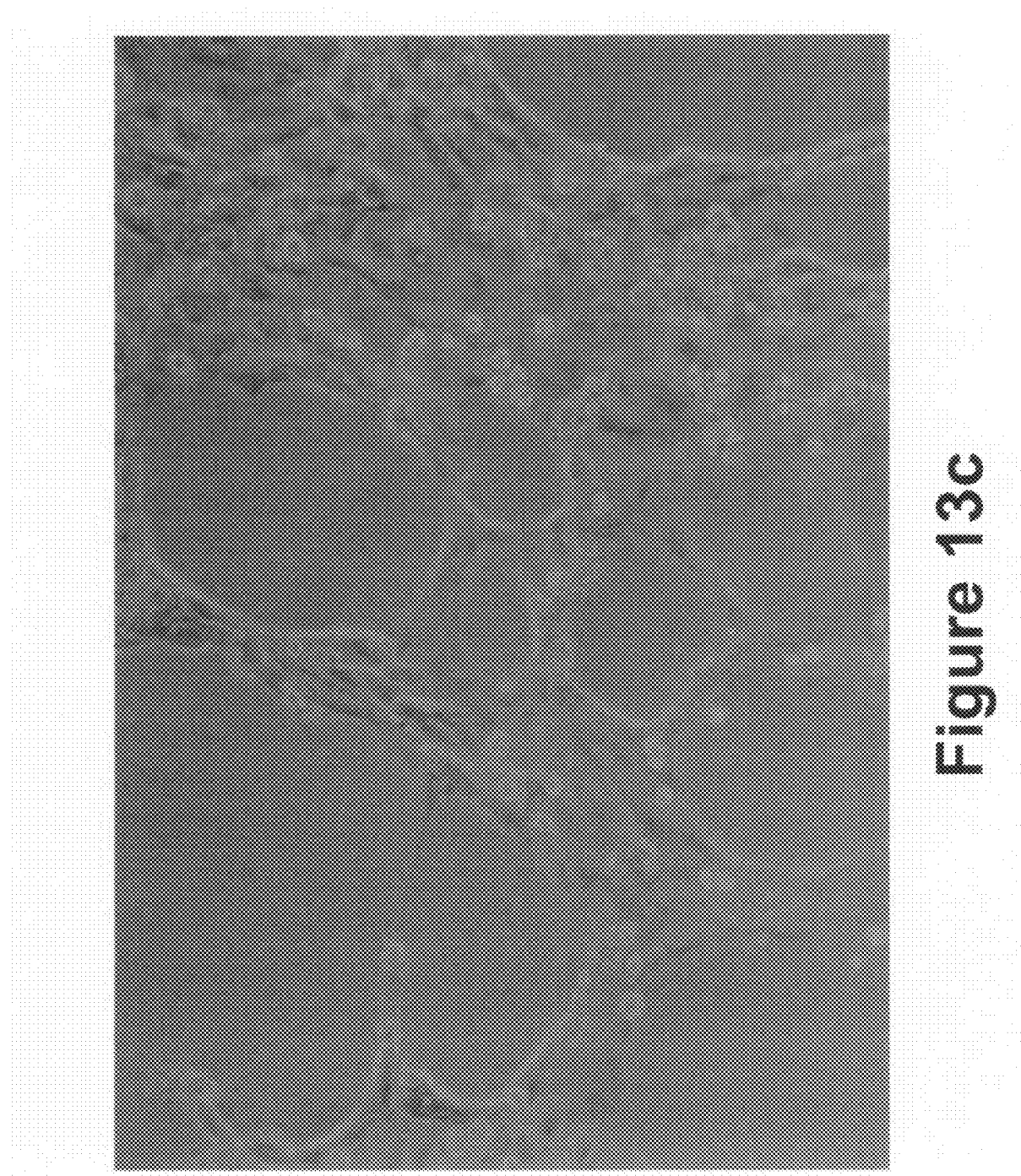
Figure 13D:
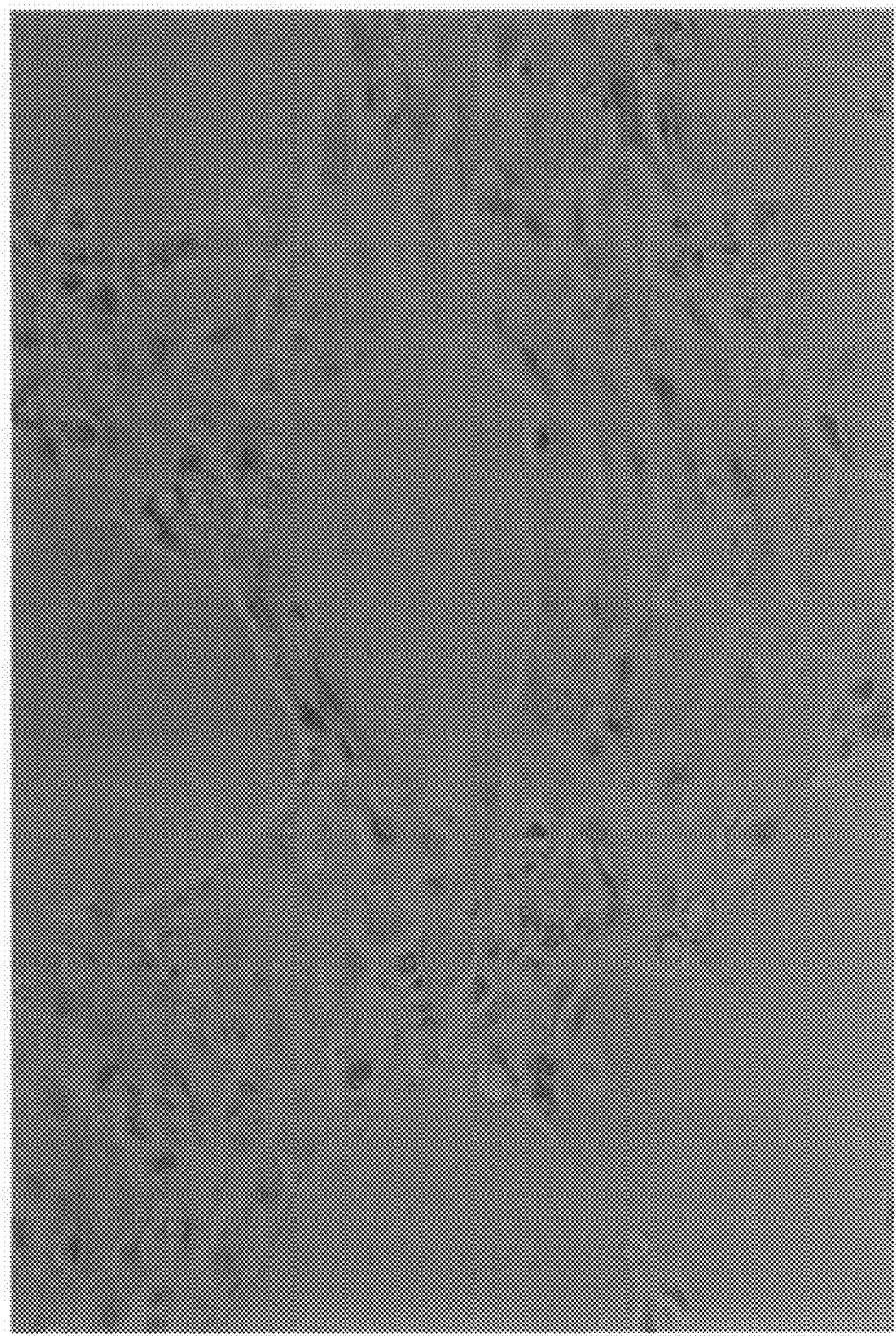
Figure 13E:
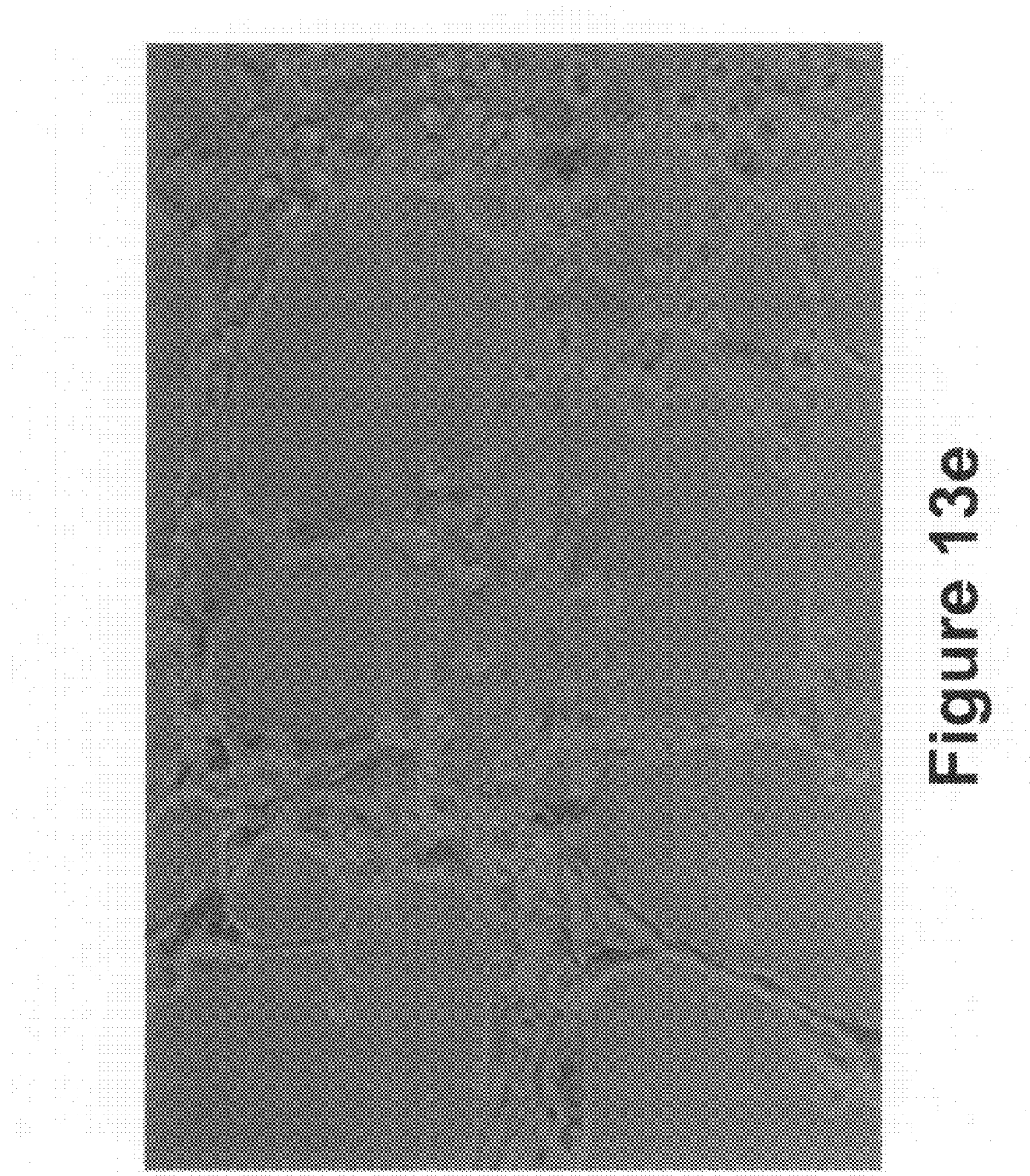
Figure 13F:
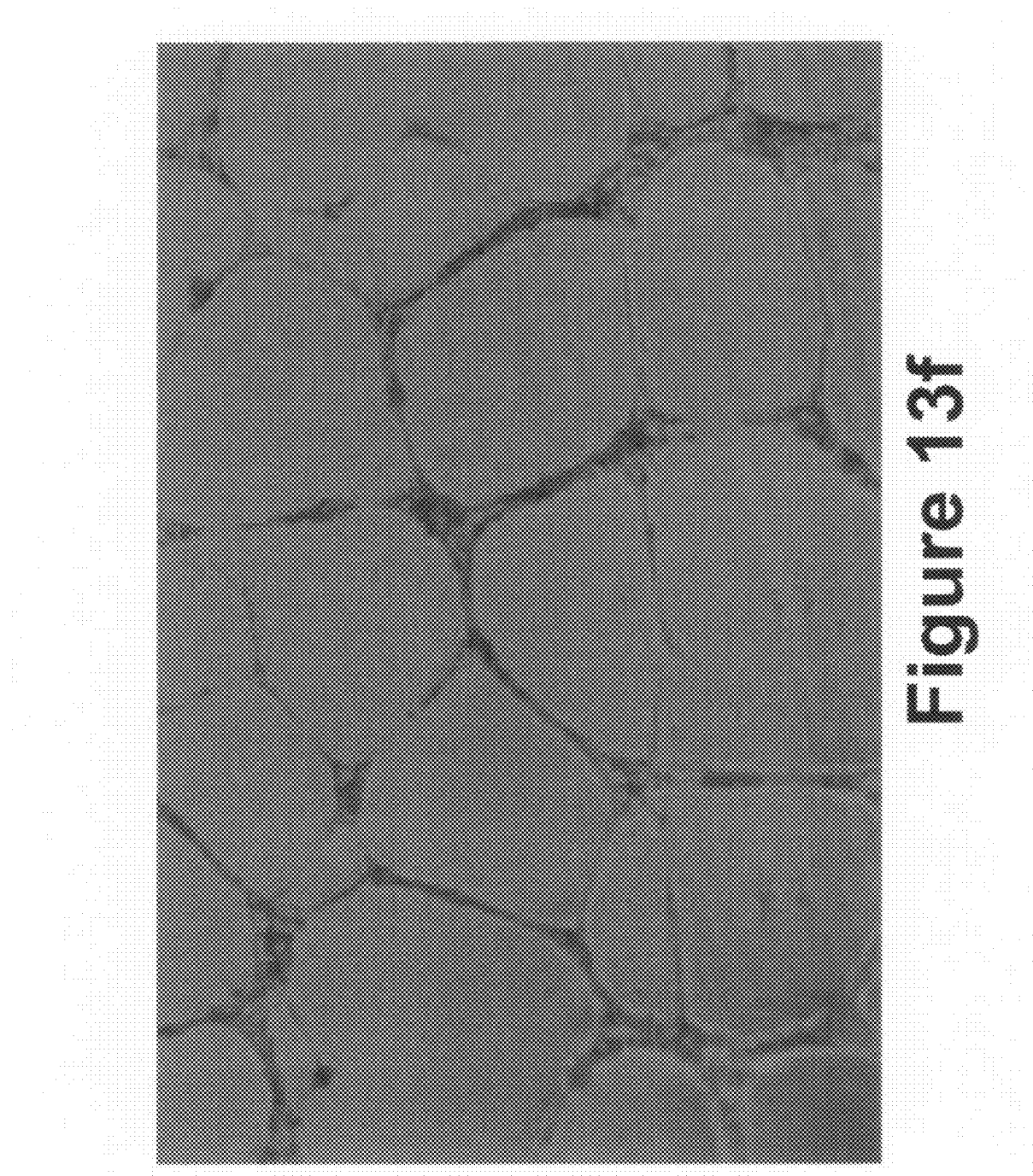

FIGS. 13a-j are photomicrographs depicting the effect of the peptides on cells tube formation. FIGS. 13a-e demonstrate MVEC tube formation induced by 8 hours incubation of VEGF (FIG. 13b), YR (FIG. 13c), QF (FIG. 13d), VL (FIG. 13e), as compared to untreated control (FIG. 13a). Photos were taken after 8 incubation; Magnification×100. FIGS. 13f-j demonstrate EC tube formation induced by 20 hours incubation of FGF (FIG. 13g), YR (FIG. 13h), QF (FIG. 13i), VL (FIG. 13j), as compared to untreated control (FIG. 13f).

Figure 14A:
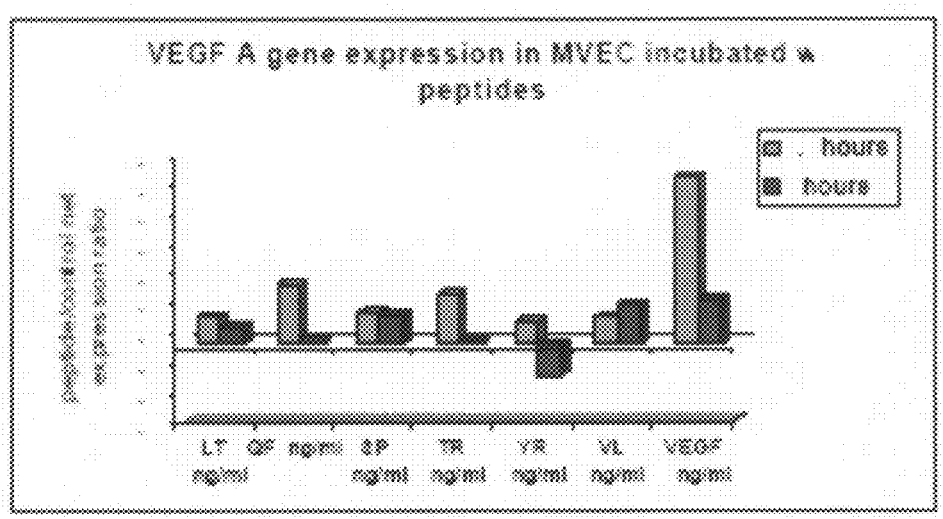
Figure 14B:
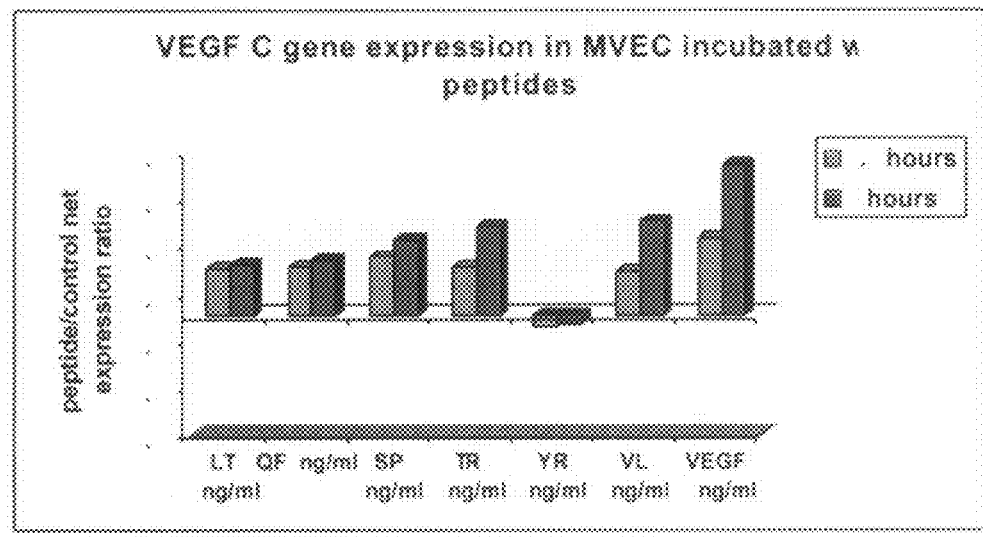
Figure 14C:
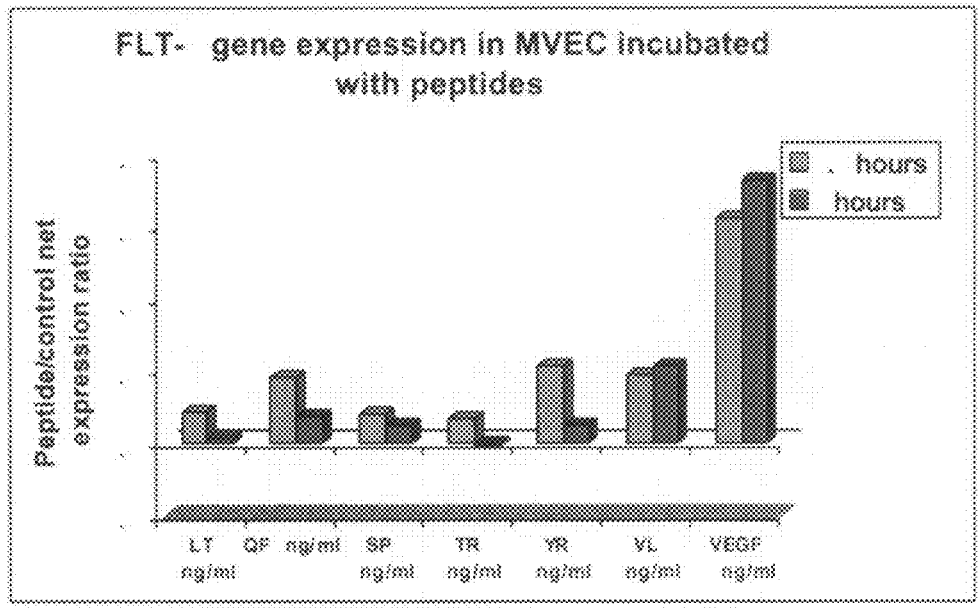
Figure 14D:
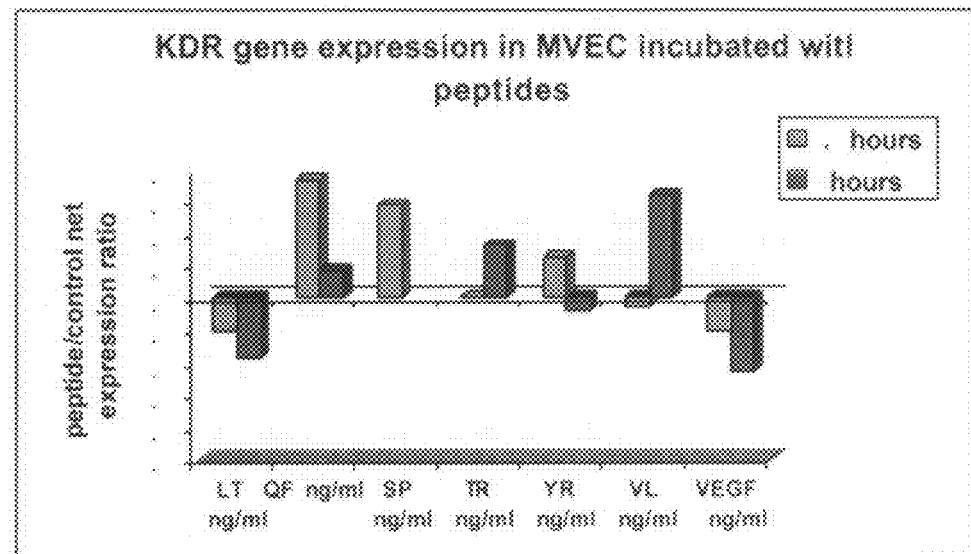
Figure 14E:
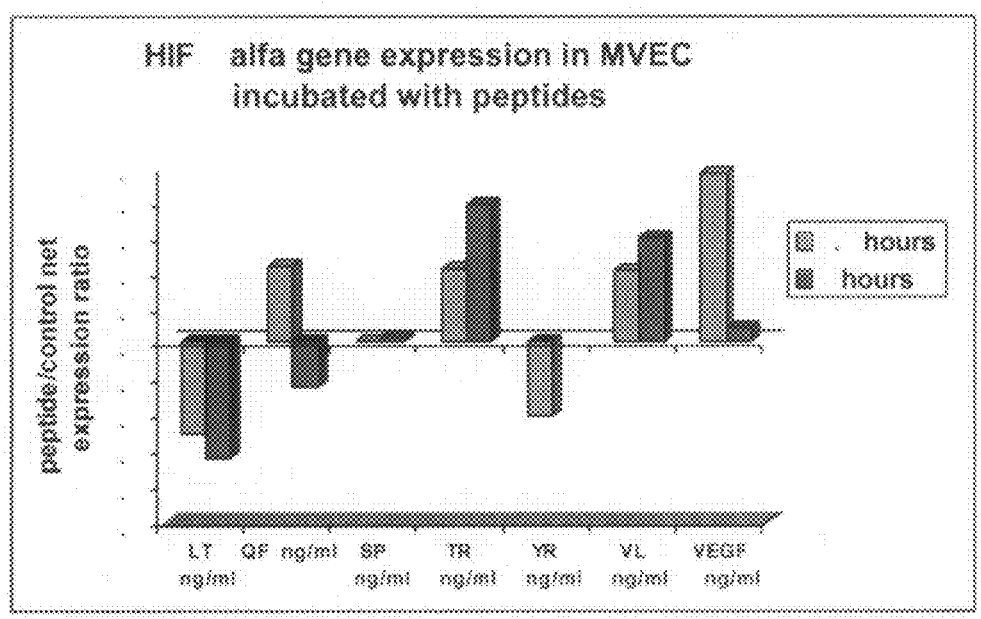

FIGS. 14a-e are bar graphs depicting the effect of synthetic peptides on gene expression of the following genes in MVECs: FIG. 14a—VEGF-A; FIG. 14b—VEGF-C; FIG. 14c—FLT-1; FIG. 14d—KDR; FIG. 14e—HEF-1α. The synthetic peptides (LT, QF, SP, TR, YR and VL at concentration of 1 ng/ml) or VEGF (at concentration of 10 ng/ml) were added to the cells and gene expression was determined using real-time PCR 1.5 and 6 hours following the peptide or VEGF addition. Results are presented as net expression ratio of treated cells as compared to untreated controls.

Figure 15:
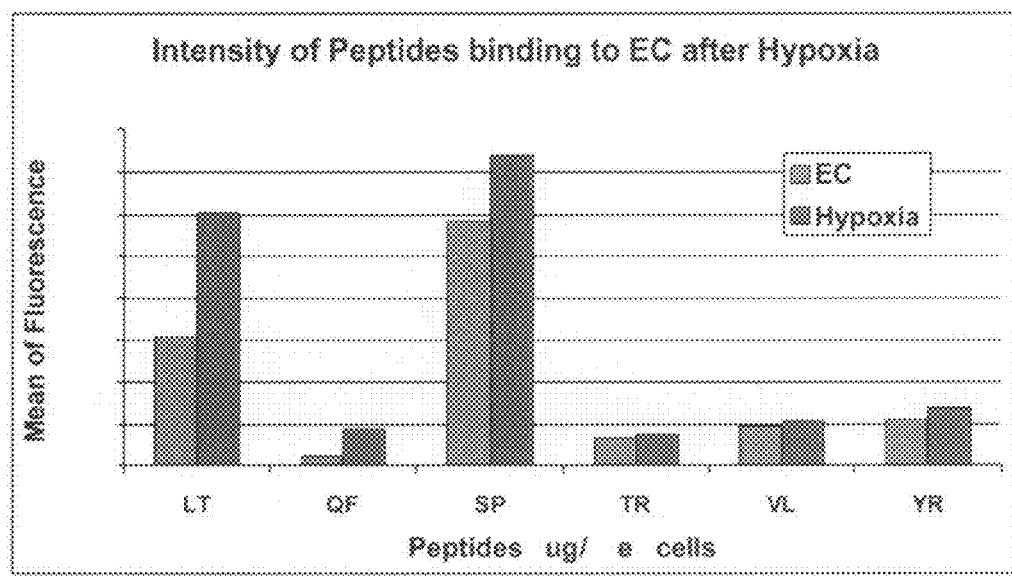

FIG. 15 is a bar graph demonstrating the intensity of synthetic peptides binding to ECs exposed to the effect of hypoxia treatment Flow cytometry analysis was effected on the binding of 6 μg FITC labeled synthetic peptide (LT, QF, SP, TR, VL and YR) to $10^5$ untreated ECs or ECs after hypoxia. The bars compare mean fluorescence (488 nm) obtained after 2 hours incubation of the FITC labeled synthetic peptides with ECs. Data was collected using FACS.

FIGS. 16a-b are graphs depicting the intensity of synthetic peptides binding to ECs exposed to the effect of hypoxia. The graphs present flow cytometry analysis of 6 μg FITC labeled SP peptide (FIG. 16a) or LT peptide (FIG. 16b) to $10^5$ ECs following 2 hours incubation. Red line—ECs without hypoxia; green line—ECs after hypoxia; black line—isotype control.

Figure 17A:
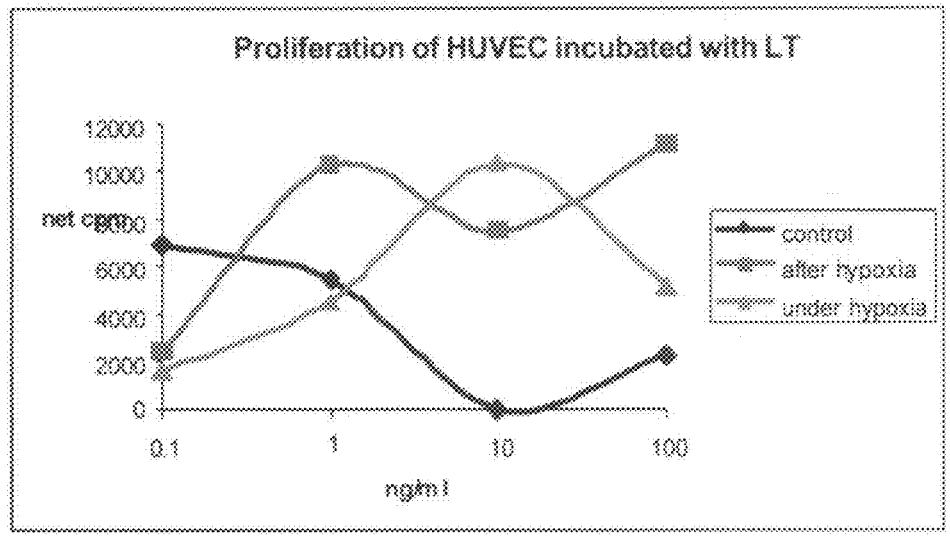
Figure 17B:
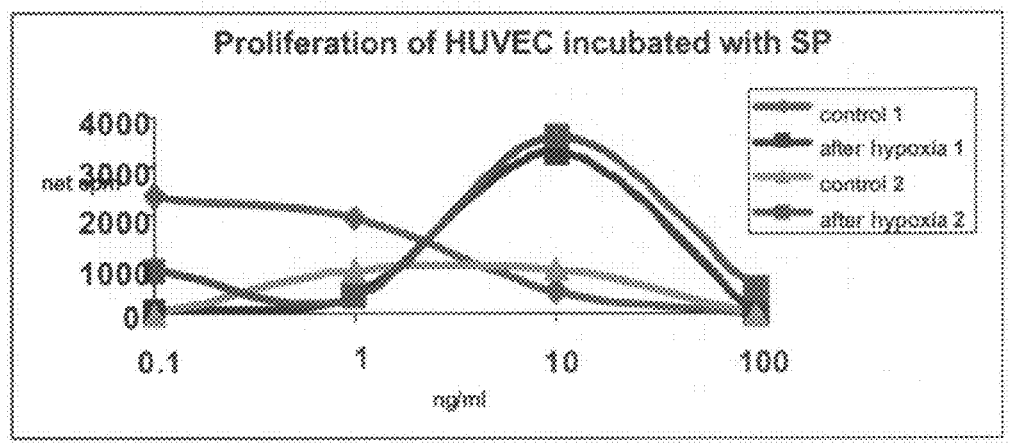
Figure 17C:
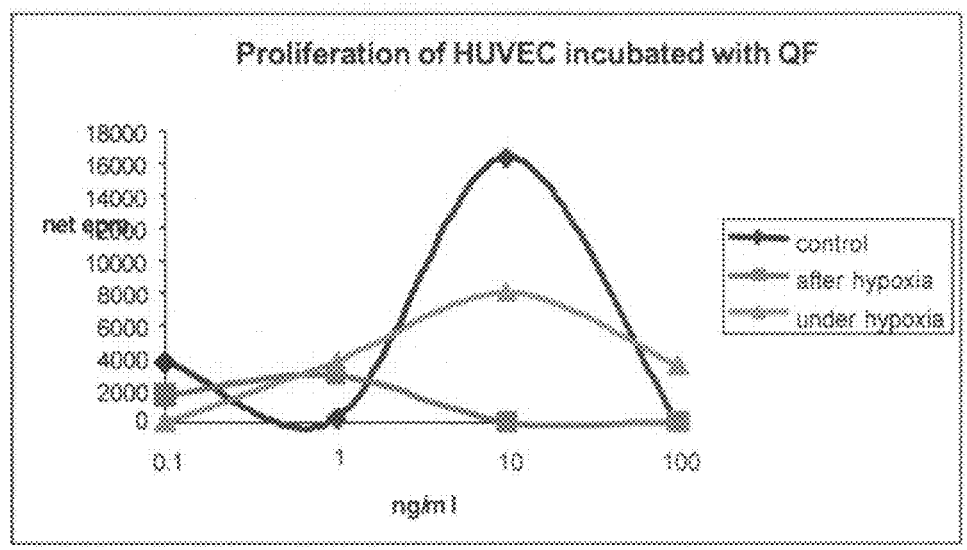

FIGS. 17a-f are graphs depicting the effect of synthetic peptides on cells proliferation. FIGS. 17a-c illustrate the proliferation of HLUVECs induced by LT (FIG. 17a), SP (FIG. 17b), or QF (FIG. 17c) at concentrations of 0.01, 1, 10, and 100 ng/ml, following 24 hours incubation in EBM-2. FIGS. 10d-f illustrate the proliferation of MVECs induced by LT (FIG. 17d), SP (FIG. 17e), or QF (FIG. 17f) at concentrations of 0.01, 1, 10, and 100 ng/ml following 24 hours incubation in EBM-MV. The plots compare the proliferation of cells under normal conditions (control), under hypoxic conditions or after hypoxic conditions. Data was obtained by measuring radioactive [$^3$H]-Thymidine uptake into cells in a scintillation β counter by cpm/min in the last 6 hours of incubation.

Figure 18A:
Figure 18B:
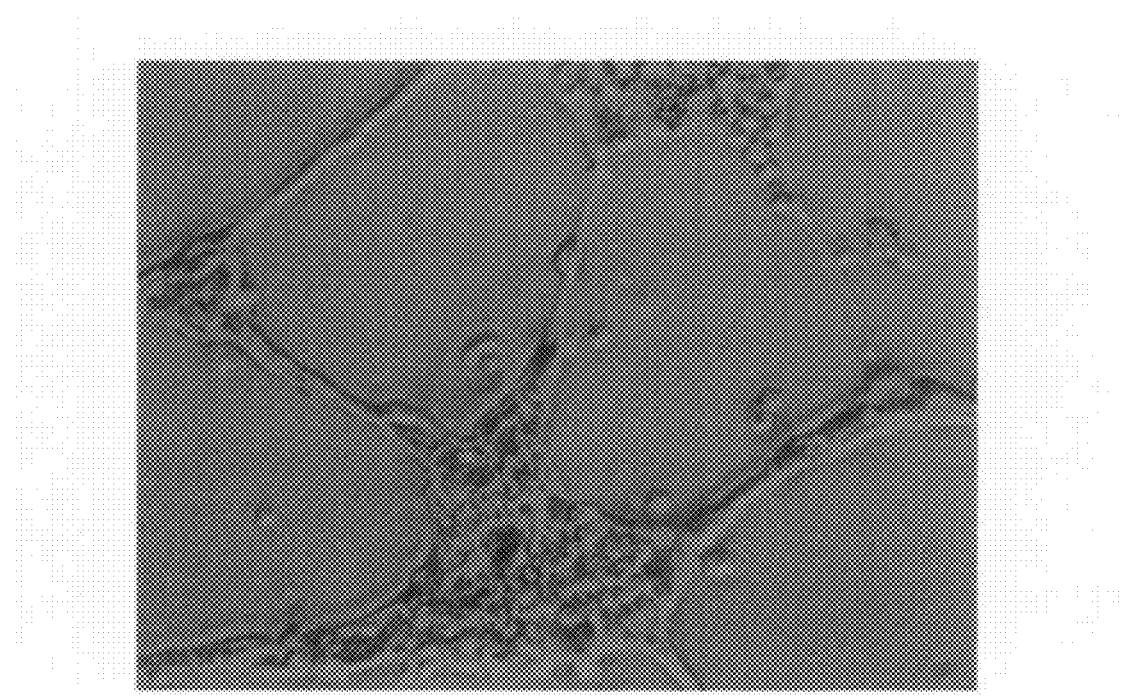
Figure 18C:
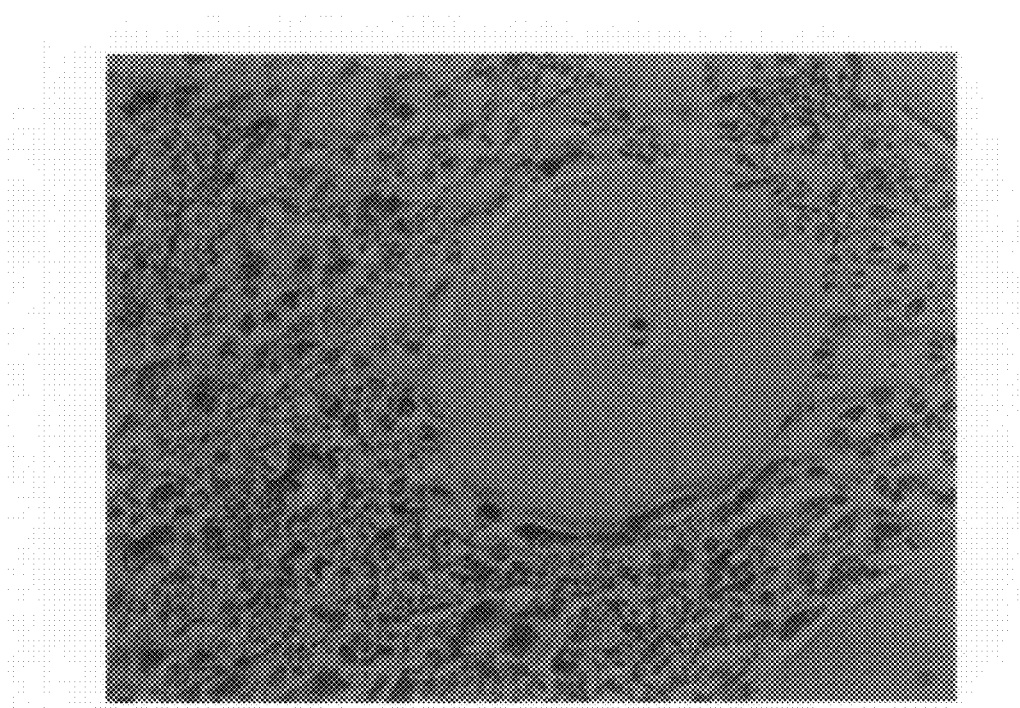
Figure 18D:
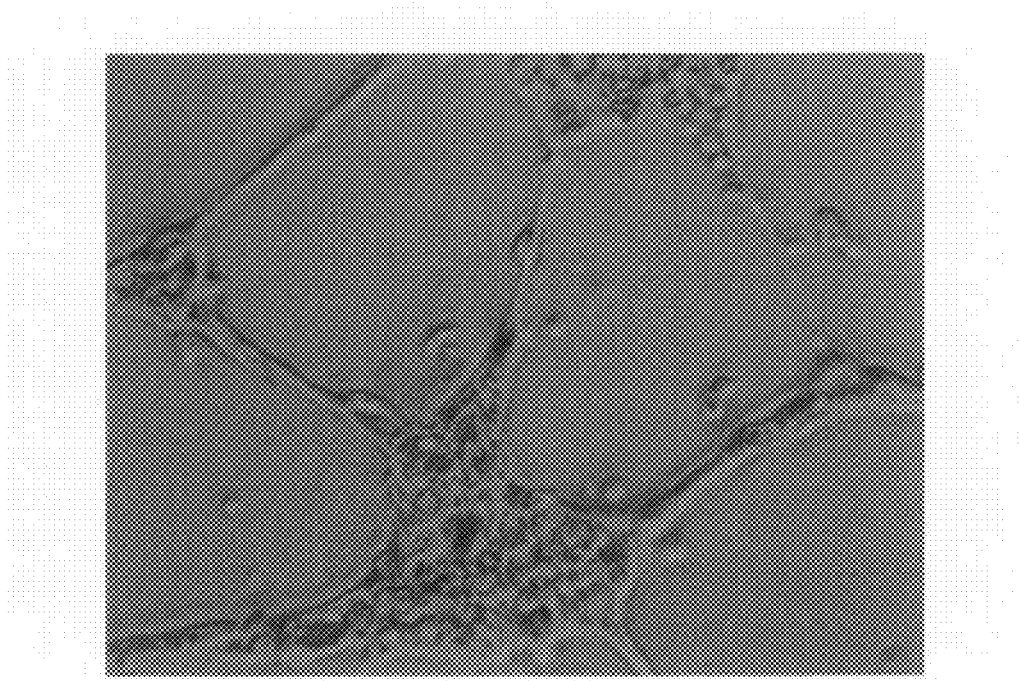
Figure 18E:
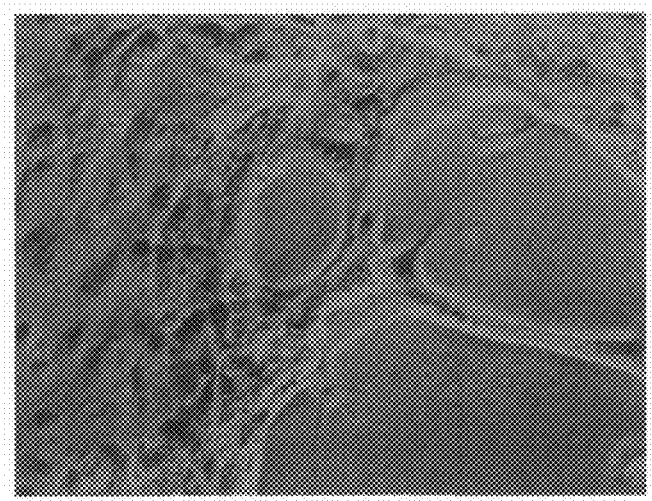

FIGS. 18a-e are photomicrographs depicting the effect of SP on HUVEC (FIGS. 18a-c) and MVEC (FIGS. 18d-e) tube formation under hypoxic conditions. FIGS. 18a-c demonstrate EC tube formation induced by 18 hours incubation with FGF (FIG. 18b), or SP (FIG. 18c) as compared to control (FIG. 18a). FIGS. 18d-e demonstrate MVEC tube formation induced by 18 hours incubation with FGF (FIG. 18d), or SP (FIG. 18e). Photos were taken after 18 hours incubation. Magnification×100.

Figure 19A:
Figure 19B:
Figure 19C:
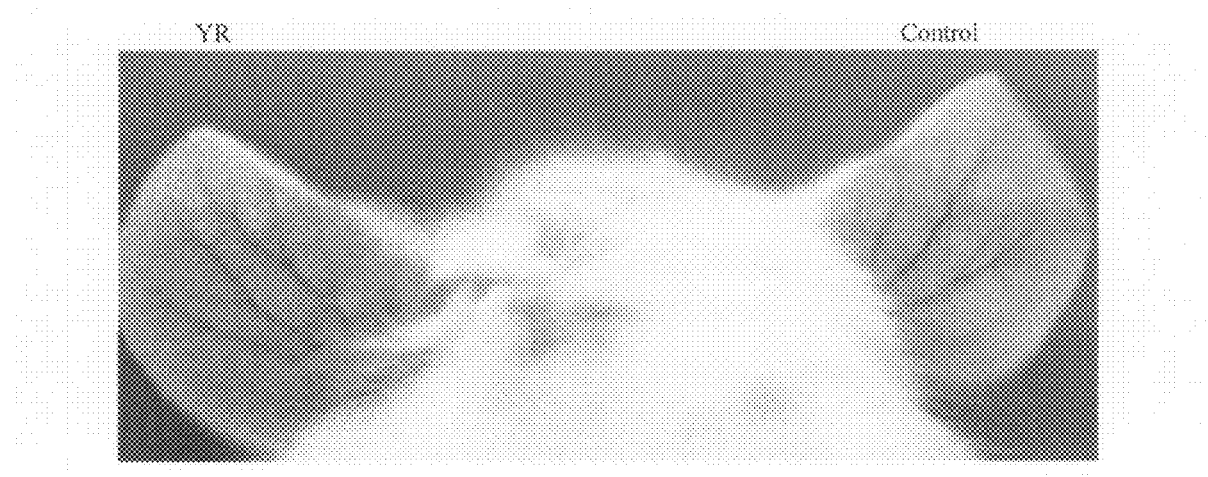
Figure 19D:
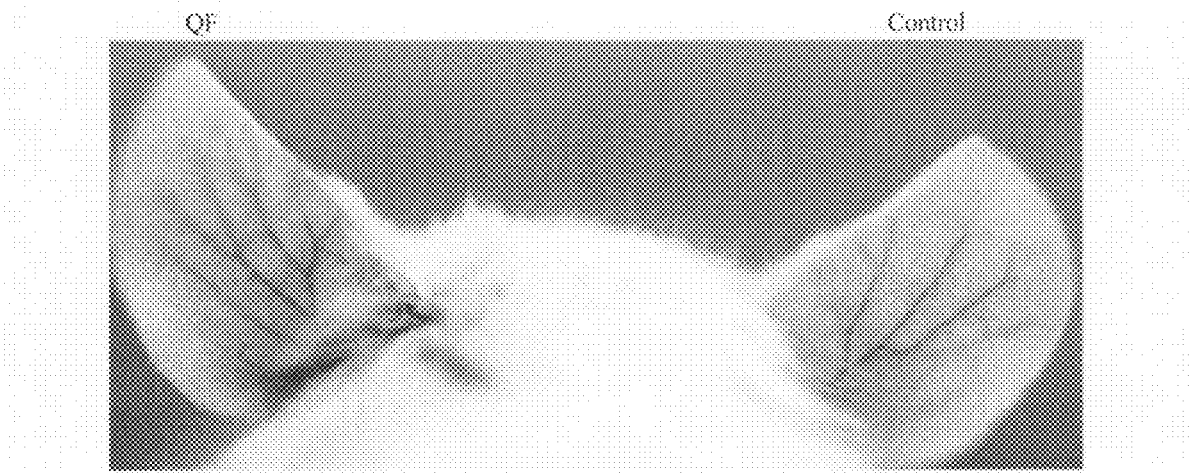
Figure 19E:

FIGS. 19a-e are photomicrographs depicting the effect of synthetic peptides on vascularization of mouse ears. The figures demonstrate the vascularization as induced by subcutaneous injection of VEGF (100 ng/mouse ear, FIG. 19a), LT (10 μg/ear; FIG. 19b), YR (10 μg/ear; FIG. 19c), QF (μg/ear; FIG. 19d), or SP (FIG. 19e, 0.1 μg/ear). Each injection was carried out in a final volume of 10 μl, i.e., 10 μg/10 μl PBS, 0.1 μg/10 μl PBS or 10 μl PBS (Control). Photos were taken 2 days following injection.

Figure 20A:
Figure 20B:

FIGS. 20a-b are photomicrographs depicting the effect of TR peptide on vascularization of mouse ear. Shown are histology sections demonstrating vascularization and neo-vascularization induced by 10 μg TR (FIG. 20b) as compared to control (FIG. 20a). Note, injection of TR peptide reveals large blood vessel formation and neovascularization as demonstrated by capillary blood vessels with single erytrocyte cell.

Figure 21:
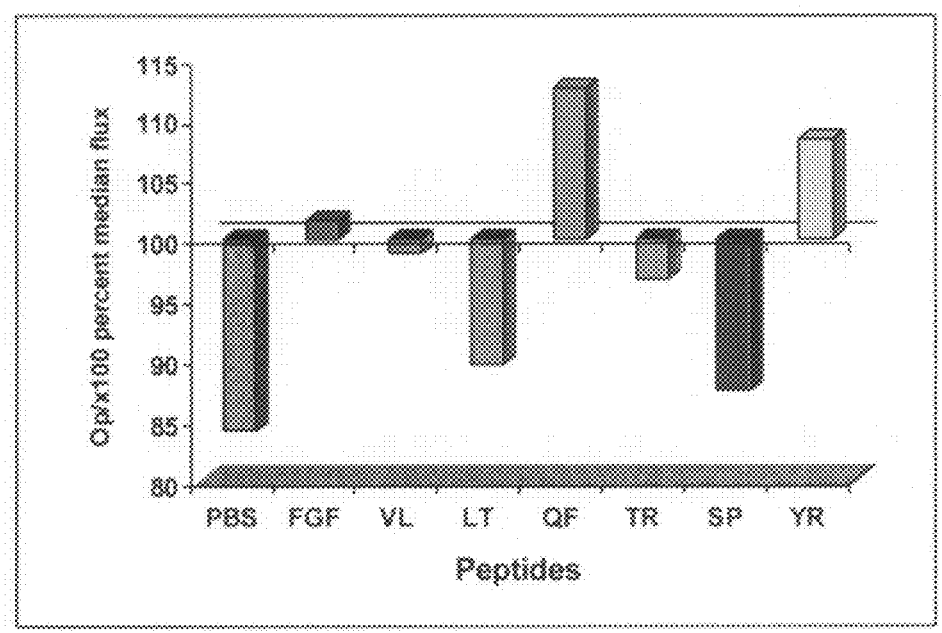

FIG. 21 is a bar graph depicting median flux of ischemic hind limb/control in a rat ischemic hind limb model. The Figure presents the ischemic hind limb blood flow measured at days 4, 7, 9 and 13. Results are the mean of 4, 7 9, and 13 days after peptide inoculation after 600 μg of VL, LT, QF, TR, SP, YR, FGF or PBS injection to the ischemic leg as compared to the other leg. Results are expressed as OP/control ×100 median flux (Percent median flux of the operated leg versus non operated control leg). Data was obtained at days 4, 7, 9, 13 using a Laser Doppler Blood Flow analyzer.

FIGS. 22a-c illustrate the uncovering a conserved sequence motif which is shared by the peptides of the present invention and the mouse VEGF-B (Swiss-Prot Accession: VEGB_MOUSE). FIG. 22a—the amino acid sequences of the peptides of the present invention; FIG. 22b—alignment of the amino acid sequences of VL, QF, YR and TR and scanning by e-Motif uncovers a conserved motif "pw[il][de].y"; FIG. 22c—alignment of the amino acid sequences of VL, QF, YR and TR with mouse VEGF-B.

DESCRIPTION OF THE PREFERRED EMBODIMENTS

The present invention is of peptides, which can be used for promoting tissue angiogenesis. Specifically, the present invention can be used to treat angiogenesis-dependent diseases, such as ischemic vascular diseases.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Angiogenesis is the process of generating new capillary blood vessels involving an interplay between cells and soluble factors (1). The process is characterized by the migration of activated endothelial cells that proliferate to form new vessels, which are surrounded by layers of periendothelial cells, including pericytes for small blood vessels and smooth muscle cells for large blood vessels.

Angiogenesis-dependent diseases are a consequence of an imbalanced angiogenic process resulting in an excessive amount of new blood vessels or insufficient number of blood vessels. Insufficient angigenesis is related to a large number of diseases and conditions, such as coronary artery diseases and delayed wound healing.

Therapeutic angiogenesis is aimed at stimulating new blood vessel growth. The concept of such a therapy is based on the premise that the inherent potential of vascularization in a vascular tissue can be utilized to promote the development of new blood vessels under the influence of the appropriate angiogenic molecules.

While reducing the present invention to practice, the present inventors used a 12-mer phage display peptide library to uncover peptides that are able to bind the cell-surface of endothelial cells incubated under normoxic or hypoxic conditions.

As is illustrated in the Examples section which follows, the peptides of the present invention triggered angiogenic reactions including, endothelial cell-proliferation and migration, aortic ring sprouting, tube formation and in-vivo vascularization. These findings suggest that the peptides of the present invention can be used in the treatment of various angiogenesis-dependent diseases, such as ischemic-vascular diseases. Furthermore, characterization of the nature of endothelial cell signaling by these peptides will provide the basis for the development of targeted angiogenic therapy for diseases, such as cardiovascular disease.

Thus, according to one aspect of the present invention there is provided a peptide including an amino acid sequence as set forth in SEQ ID NO: 2, 4, 6, 8, 10 or 12, the peptide is at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, and no more than 50 amino acid residues in length.

According to another aspect of the present invention there is provided a peptide including an amino acid sequence selected from the group consisting of SEQ ID NOs: NO:13, 27 or 32, the peptide is at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, and no more than 50 amino acid residues in length.

As is shown in Example 6 of the Examples section, the peptides of this aspect of the present invention share a conserved amino acid sequence (SEQ ID NO:13, 27 or 32) with mammalian vascular endothelial growth factor B (VEGF-B, SwissProt/TrEMBL Accession: VEGB_MOUSE), thereby substantiating the angiogenic function attributed to the peptides of this aspect of the present invention.

Preferably, the peptide of the present invention includes the sequence set forth by SEQ ID NO: 2, 6, 8 or 12, more preferably the peptide of the present invention includes the sequence set forth by SEQ ID NO:6 or 8.

According to another preferred embodiment of this aspect of the present invention the amino acid sequence is as set forth in SEQ ID NO: 2, 6, 8, or 12, preferably the amino acid sequence is as set forth in SEQ ID NO:6 or 8.

The present invention also envisages the use of peptides containing more than one consensus sequence as provided in SEQ ID NO:14.

According to yet another aspect of the present invention there is provided a peptide including an amino acid sequence as set forth in SEQ ID NO: 14, the peptide is at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, and no more than 50 amino acid residues in length.

The term "peptide" as used herein encompasses native peptides (either degradation products, synthetically synthesized peptides or recombinant peptides) and peptidomimetics (typically, synthetically synthesized peptides), as well as peptoids and semipeptoids which are peptide analogs, which may have, for example, modifications rendering the peptides more stable while in a body or more capable of penetrating into cells. Such modifications include, but are not limited to N terminus modification, C terminus modification, peptide bond modification, including, but not limited to, CH2—NH, CH2—S, CH2—S=O, O=C—NH, CH2—O, CH2—CH2, S=C—NH, CH=CH or CF=CH, backbone modifications, and residue modification. Methods for preparing peptidomnimetic compounds are well known in the art and are specified, for example, in Quantitative Drug Design, C.A. Ramsden Gd., Chapter 17.2, F. Choplin Pergamon Press (1992), which is incorporated by reference as if fully set forth herein.

Further details in this respect are provided hereinunder. Peptide bonds (—CO—NH—) within the peptide may be substituted, for example, by N-methylated bonds (—N(CH$_3$)—CO—), ester bonds (—C(R)H—C—O—O—C(R)—N—), ketomethylen bonds (—CO—CH2—), α-aza bonds (—NH—N(R)—CO—), wherein R is any alkyl, e.g., methyl, carba bonds (—CH2—NH—), hydroxyethylene bonds (—CH(OH)—CH2—), thioamide bonds (—CS—NH—), olefinic double bonds (—CH=CH—), retro amide bonds (—NH—CO—), peptide derivatives (—N(R)—CH2—CO—), wherein R is the "normal" side chain, naturally presented on the carbon atom.

These modifications can occur at any of the bonds along the peptide chain and even at several (2-3) at the same time.

Natural aromatic amino acids, Trp, Tyr and Phe, may be substituted for synthetic non-natural acid, such as Phenylglycine, TIC, naphthylelanine (Nol), ring-methylated derivatives of Phe, halogenated derivatives of Phe or o-methyl-Tyr.

In addition to the above, the peptides of the present invention may also include one or more modified amino acids or one or more non-amino acid monomers (e.g. fatty acids, complex carbohydrates etc).

As used herein in the specification and in the claims section below the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Tables 1 and 2 below list naturally occurring amino acids (Table 1) and non-conventional or modified amino acids (e.g., synthetic, Table 2) which can be used with the present invention.

TABLE 1

| Amino Acid | Three-Letter Abbreviation | One-letter Symbol |
|---|---|---|
| alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| glycine | Gly | G |
| Histidine | His | H |
| isoleucine | Ile | I |
| leucine | Leu | L |
| Lysine | Lys | K |
| Methionine | Met | M |
| phenylalanine | Phe | F |
| Proline | Pro | P |
| Serine | Ser | S |
| Threonine | Thr | T |
| tryptophan | Trp | W |
| tyrosine | Tyr | Y |
| Valine | Val | V |
| Any amino acid as above | Xaa | X |

TABLE 2

| Non-conventional amino acid | Code |
|---|---|
| α-aminobutyric acid | Abu |
| α-amino-α-methylbutyrate | Mgabu |
| aminocyclopropane-carboxylate | Cpro |
| aminoisobutyric acid | Aib |
| aminonorbornyl-carboxylate | Norb |
| cyclohexylalanine | Chexa |
| cyclopentylalanine | Cpen |
| D-alanine | Dal |
| D-arginine | Darg |
| D-aspartic acid | Dasp |
| D-cysteine | Dcys |
| D-glutamine | Dgln |
| D-glutamic acid | Dglu |
| D-histidine | Dhis |
| D-isoleucine | Dile |
| D-leucine | Dleu |
| D-lysine | Dlys |
| D-methionine | Dmet |
| D-ornithine | Dorn |
| D-phenylalanine | Dphe |
| D-proline | Dpro |
| D-serine | Dser |
| D-threonine | Dthr |
| D-tryptophan | Dtrp |
| D-tyrosine | Dtyr |
| D-valine | Dval |
| D-α-methylalanine | Dmala |
| D-α-methylarginine | Dmarg |
| D-α-methylasparagine | Dmasn |
| D-α-methylaspartate | Dmasp |
| D-α-methylcysteine | Dmcys |
| D-α-methylglutamine | Dmgln |
| D-α-methylhistidine | Dmhis |
| D-α-methylisoleucine | Dmile |
| D-α-methylleucine | Dmleu |
| D-α-methyllysine | Dmlys |
| D-α-methylmethionine | Dmmet |
| D-α-methylornithine | Dmorn |
| D-α-methylphenylalanine | Dmphe |
| D-α-methylproline | Dmpro |
| D-α-methylserine | Dmser |
| D-α-methylthreonine | Dmthr |
| D-α-methyltryptophan | Dmtrp |
| D-α-methyltyrosine | Dmty |
| D-α-methylvaline | Dmval |

TABLE 2-continued

| Non-conventional amino acid | Code |
|---|---|
| D-α-methylalnine | Dnmala |
| D-α-methylarginine | Dnmarg |
| D-α-methylasparagine | Dnmasn |
| D-α-methylasparatate | Dnmasp |
| D-α-methylcysteine | Dnmcys |
| D-N-methylleucine | Dnmleu |
| D-N-methyllysine | Dnmlys |
| N-methylcyclohexylalanine | Nmchexa |
| D-N-methylornithine | Dnmorn |
| N-methylglycine | Nala |
| N-methylaminoisobutyrate | Nmaib |
| N-(1-methylpropyl)glycine | Nile |
| N-(2-methylpropyl)glycine | Nile |
| N-(2-methylpropyl)glycine | Nleu |
| D-N-methyltryptophan | Dnmtrp |
| D-N-methyltyrosine | Dnmtyr |
| D-N-methylvaline | Dnmval |
| γ-aminobutyric acid | Gabu |
| L-t-butylglycine | Tbug |
| L-ethylglycine | Etg |
| L-homophenylalanine | Hphe |
| L-α-methylarginine | Marg |
| L-α-methylaspartate | Masp |
| L-α-methylcysteine | Mcys |
| L-α-methylglutamine | Mgln |
| L-α-methylhistidine | Mhis |
| L-α-methylisoleucine | Mile |
| D-N-methylglutamine | Dnmgln |
| D-N-methylglutamate | Dnmglu |
| D-N-methylhistidine | Dnmhis |
| D-N-methylisoleucine | Dnmile |
| D-N-methylleucine | Dnmleu |
| D-N-methyllysine | Dnmlys |
| N-methylcyclohexylalanine | Nmchexa |
| D-N-methylornithine | Dnmorn |
| N-methylglycine | Nala |
| N-methylaminoisobutyrate | Nmaib |
| N-(1-methylpropyl)glycine | Nile |
| N-(2-methylpropyl)glycine | Nleu |
| D-N-methyltryptophan | Dnmtrp |
| D-N-methyltyrosine | Dnmtyr |
| D-N-methylvaline | Dnmval |
| γ-aminobutyric acid | Gabu |
| L-t-butylglycine | Tbug |
| L-ethylglycine | Etg |
| L-homophenylalanine | Hphe |
| L-α-methylarginine | Marg |
| L-α-methylaspartate | Masp |
| L-α-methylcysteine | Mcys |
| L-α-methylglutamine | Mgln |
| L-α-methylhistidine | Mhis |
| L-α-methylisoleucine | Mile |
| L-α-methylleucine | Mleu |
| L-α-methylmethionine | Mmet |
| L-α-methylnorvaline | Mnva |
| L-α-methylphenylalanine | Mphe |
| L-α-methylserine | mser |
| L-α-methylvaline | Mtrp |
| L-α-methylleucine | Mval Nnbhm |
| N-(N-(2,2-diphenylethyl) carbamylmethyl-glycine | Nnbhm |
| 1-carboxy-1-(2,2-diphenyl ethylamino)cyclopropane | Nmbc |
| L-N-methylalanine | Nmala |
| L-N-methylarginine | Nmarg |
| L-N-methylasparagine | Nmasn |
| L-N-methylaspartic acid | Nmasp |
| L-N-methylcysteine | Nmcys |
| L-N-methylglutamine | Nmgin |
| L-N-methylglutamic acid | Nmglu |
| L-N-methylhistidine | Nmhis |
| L-N-methylisolleucine | Nmile |
| L-N-methylleucine | Nmleu |
| L-N-methyllysine | Nmlys |
| L-N-methylmethionine | Nmmet |
| L-N-methylnorleucine | Nmnle |
| L-N-methylnorvaline | Nmnva |

TABLE 2-continued

| Non-conventional amino acid | Code |
|---|---|
| L-N-methylornithine | Nmorn |
| L-N-methylphenylalanine | Nmphe |
| L-N-methylproline | Nmpro |
| L-N-methylserine | Nmser |
| L-N-methylthreonine | Nmthr |
| L-N-methyltryptophan | Nmtrp |
| L-N-methyltyrosine | Nmtyr |
| L-N-methylvaline | Nmval |
| L-N-methylethylglycine | Nmetg |
| L-N-methyl-t-butylglycine | Nmtbug |
| L-norleucine | Nle |
| L-norvaline | Nva |
| α-methyl-aminoisobutyrate | Maib |
| α-methyl-γ-aminobutyrate | Mgabu |
| α-methylcyclohexylalanine | Mchexa |
| α-methylcyclopentylalanine | Mcpen |
| α-methyl-α-napthylalanine | Manap |
| α-methylpenicillamine | Mpen |
| N-(4-aminobutyl)glycine | Nglu |
| N-(2-aminoethyl)glycine | Naeg |
| N-(3-aminopropyl)glycine | Norn |
| N-amino-α-methylbutyrate | Nmaabu |
| α-napthylalanine | Anap |
| N-benzylglycine | Nphe |
| N-(2-carbamylethyl)glycine | Ngln |
| N-(carbamylmethyl)glycine | Nasn |
| N-(2-carboxyethyl)glycine | Nglu |
| N-(carboxymethyl)glycine | Nasp |
| N-cyclobutylglycine | Ncbut |
| N-cycloheptylglycine | Nchep |
| N-cyclohexylglycine | Nchex |
| N-cyclodecylglycine | Ncdec |
| N-cyclododeclglycine | Ncdod |
| N-cyclooctylglycine | Ncoct |
| N-cyclopropylglycine | Ncpro |
| N-cycloundecylglycine | Ncund |
| N-(2,2-diphenylethyl)glycine | Nbhm |
| N-(3,3-diphenylpropyl)glycine | Nbhe |
| N-(3-indolylyethyl) glycine | Nhtrp |
| N-methyl-γ-aminobutyrate | Nmgabu |
| D-N-methylmethionine | Dnmmet |
| N-methylcyclopentylalanine | Nmcpen |
| D-N-methylphenylalanine | Dnmphe |
| D-N-methylproline | Dnmpro |
| D-N-methylserine | Dnmser |
| D-N-methylserine | Dnmser |
| D-N-methylthreonine | Dnmthr |
| N-(1-methylethyl)glycine | Nva |
| N-methyla-napthylalanine | Nmanap |
| N-methylpenicillamine | Nmpen |
| N-(p-hydroxyphenyl)glycine | Nhtyr |
| N-(thiomethyl)glycine | Ncys |
| penicillamine | Pen |
| L-α-methylalanine | Mala |
| L-α-methylasparagine | Masn |
| L-α-methyl-t-butylglycine | Mtbug |
| L-methylethylglycine | Metg |
| L-α-methylglutamate | Mglu |
| L-α-methylhomo phenylalanine | Mhphe |
| N-(2-methylthioethyl)glycine | Nmet |
| N-(3-guanidinopropyl)glycine | Narg |
| N-(1-hydroxyethyl)glycine | Nthr |
| N-(hydroxyethyl)glycine | Nser |
| N-(imidazolylethyl)glycine | Nhis |
| N-(3-indolylyethyl)glycine | Nhtrp |
| N-methyl-γ-aminobutyrate | Nmgabu |
| D-N-methylmethionine | Dnmmet |
| N-methylcyclopentylalanine | Nmcpen |
| D-N-methylphenylalanine | Dnmphe |
| D-N-methylproline | Dnmpro |
| D-N-methylserine | Dnmser |
| D-N-methylthreonine | Dnmthr |
| N-(1-methylethyl)glycine | Nval |
| N-methyla-napthylalanine | Nmanap |
| N-methylpenicillamine | Nmpen |
| N-(p-hydroxyphenyl)glycine | Nhtyr |
| N-(thiomethyl)glycine | Ncys |
| penicillamine | Pen |
| L-α-methylalanine | Mala |
| L-α-methylasparagine | Masn |
| L-α-methyl-t-butylglycine | Mtbug |
| L-methylethylglycine | Metg |
| L-α-methylglutamate | Mglu |
| L-α-methylhomophenylalanine | Mhphe |
| N-(2-methylthioethyl)glycine | Nmet |
| L-α-methyllysine | Mlys |
| L-α-methylnorleucine | Mnle |
| L-α-methylornithine | Morn |
| L-α-methylproline | Mpro |
| L-α-methylthreonine | Mthr |
| L-α-methyltyrosine | Mtyr |
| L-N-methylhomophenylalanine | Nmhphe |
| N-(N-(3,3-diphenylpropyl) carbamylmethyl(1)glycine | Nnbhe |

The peptides of the present invention are preferably utilized in a linear form although it will be appreciated that in cases where cyclization does not severely interfere with peptide characteristics, cyclic forms of the peptide can also be utilized. Cyclic peptides can either be synthesized in a cyclic form or configured so as to assume a cyclic form under desired conditions (e.g., physiological conditions).

It will be appreciated that since one of the main obstacles in using short peptide fragments in therapy is their proteolytic degradation by stereospecific cellular proteases, the peptides of the present invention are preferably synthesized from D-isomers of natural amino acids [i.e., inverso peptide analogues, Tjernberg (1997) J. Biol. Chem. 272; 12601-5, Gazit (2002) Curr. Med. Chem. 9:1667-1675].

Additionally, the peptides of the present invention include retro, inverso, and retro-inverso analogues thereof. It will be appreciated that complete or extended partial retro-inverso analogues of hormones have generally been found to retain or enhance biological activity. Retro-inversion has also found application in the area of rational design of enzyme inhibitors (see U.S. Pat. No. 6,261,569).

As used herein a "retro peptide" refers to peptides that are made up of L-amino acid residues which are assembled in opposite direction to the native peptide sequence.

Retro-inverso modification of naturally occurring polypeptides involves the synthetic assembly of amino acids with α-carbon stereochemistry opposite to that of the corresponding L-amino acids, i.e., D- or D-allo-amino acids in inverse order to the native peptide sequence. A rerto inverso analogue, thus, has reversed termini and reversed direction of peptide bonds, while essentially maintaining the topology of the side chains as in the native peptide sequence.

It will be appreciated that incorporation of any of the above-mentioned amino acid modifications including conserved changes in amino acid residues of the peptides of the present invention can be effected, as long as the angiogenic function (e.g., endothelial cell proliferation, migration, vascular sprouting, vascularization) of the peptides of the present invention is retained. To test this, any of the angiogenesis assays described hereinbelow and in the Examples section which follows can be effected.

The peptides of present invention can be biochemically synthesized, such as by using standard solid phase techniques. These methods include exclusive solid phase synthesis, partial solid phase synthesis methods, fragment condensation, classical solution synthesis. These methods are preferably utilized when the peptide is relatively short (i.e., 10 kDa) and/or when it cannot be produced by recombinant techniques (i.e., not encoded by a nucleic acid sequence) and therefore involves different chemistry.

Solid phase peptide synthesis procedures are well known in the art and further described by John Morrow Stewart and Janis Dillaha Young, Solid Phase Peptide Syntheses (2nd Ed., Pierce Chemical Company, 1984).

Synthetic peptides can be purified by preparative high performance liquid chromatography [Creighton T. (1983); Proteins, structures and molecular principles. WH Freeman and Co. N.Y.] and the composition of which can be confirmed via amino acid sequencing.

Recombinant techniques are preferably used when large amounts of the peptides are required. Such recombinant techniques are described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al., (1984) Science 224: 838-843, Gurley et al. (1986) Mol. Cell. Biol. 6:559-565 and Weissbach & Weissbach, 1988, Methods for Plant Molecular Biology, Academic Press, NY, Section VIII, pp 421-463.

To produce a peptide of the present invention using recombinant technology, a polynucleotide encoding a peptide of the present invention (e.g., SEQ ID NO: 1, 3, 5, 7, 9 or 11) is ligated into a nucleic acid expression construct, which includes the polynucleotide sequence under the transcriptional control of a promoter sequence suitable for directing constitutive tissue specific or inducible transcription in the host cells, as further described hereinbelow.

Other then containing the necessary elements for the transcription and translation of the inserted coding sequence, the expression construct of the present invention can also include sequences engineered to enhance stability, production, purification, yield or toxicity of the expressed polypeptide. Such a fusion protein can be designed so that the fusion protein can be readily isolated by affinity chromatography, e.g., by immobilization on a column specific for the heterologous protein. Where a cleavage site is engineered between the peptide moiety and the heterologous protein, the peptide can be released from the chromatographic column by treatment with an appropriate enzyme or agent that disrupts the cleavage site [e.g., see Booth et al. (1988) Immunol. Lett 19:65-70; and Gardella et al., (1990) J. Biol. Chem. 265:15854-15859].

A variety of prokaryotic or eukaryotic cells can be used as host-expression systems to express the peptide coding sequence. These include, but are not limited to, microorganisms, such as bacteria transformed with a recombinant bacteriophage DNA, plasmid DNA or cosmid DNA expression vector containing the peptide coding sequence; yeast transformed with recombinant yeast expression vectors containing the peptide coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the peptide coding sequence. Mammalian expression systems can also be used to express the peptides of the present invention. Bacterial systems are preferably used to produce recombinant peptides, according to the present invention, thereby enabling a high production volume at low cost.

Other expression systems, such as insects and mammalian host cell systems, which are well known in the art, can also be used by the present invention.

In any case, transformed cells are cultured under effective conditions, which allow for the expression of high amounts of recombinant peptides. Effective culture conditions include, but are not limited to, effective media, bioreactor, temperature, pH and oxygen conditions that permit protein production. An effective medium refers to any medium in which a cell is cultured to produce the recombinant peptides of the present invention. Such a medium typically includes an aqueous solution having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art.

Depending on the vector and host system used for production, resultant proteins of the present invention may either remain within the recombinant cell; be secreted into the fermentation medium; be secreted into a space between two cellular membranes, such as the periplasmic space in E. coli; or be retained on the outer surface of a cell or viral membrane.

Following a certain time in culture, recovery of the recombinant protein is effected. The phrase "recovering the recombinant protein" refers to collecting the whole fermentation medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

The peptides of the present invention are preferably retrieved in "substantially pure" form. As used herein, "substantially pure" refers to a purity that allows for the effective use of the protein in the diverse applications, described herein As mentioned hereinabove, the peptides of the present invention can be used to promote angiogenesis (i.e., vascularization) in a tissue of a subject even under hypoxic conditions.

As used herein the term "subject" refers to a mammal, such as a canine, a feline, a bovine, a porcine, an equine. Preferably, the subject of the present invention is human.

The subject of this aspect of the present invention may suffer from an angiogenesis-dependent disease or disorder. Examples include, but are not limited to delayed wound-healing, delayed ulcer healing, reproduction associated disorders, arteriosclerosis, myocardial ischemia, peripheral ischemia, cerebral ischemia, retinopathy, remodeling disorder, von Hippel-Lindau syndrome, diabetes and hereditary hemorrhagic telengiectasia.

It will be appreciated that the peptides of the present invention can also be expressed from a nucleic acid construct administered to the subject employing any suitable mode of administration, described hereinabove (i.e., in-vivo gene therapy). Alternatively, the nucleic acid construct is introduced into a suitable cell via an appropriate gene delivery vehicle/method (transfection, transduction, homologous recombination, etc.) and an expression system as needed and then the modified cells are expanded in culture and returned to the individual (i.e., ex-vivo gene therapy). However, to enable secretion of the peptides of the present invention the polynucleotides encoding thereof (e.g., SEQ ID NO: 1, 3, 5, 7, 9 or 11) preferably further include a polynucleotide sequence which encodes an in-frame signal peptide (e.g., the signal peptide of human VEGF-B Swiss-Prot/TrEMBL Accession VEGB_HUMAN).

To enable cellular expression of the peptides of the present invention, the nucleic acid construct of the present invention further includes at least one cis acting regulatory element As used herein, the pbrase "cis acting regulatory element" refers to a polynucleotide sequence, preferably a promoter, which binds a trans acting regulator and regulates the transcription of a coding sequence located downstream thereto.

Any available promoter can be used by the present methodology. In a preferred embodiment of the present invention, the promoter utilized by the nucleic acid construct of the present invention is active in the specific cell population transformed. Examples of cell type-specific and/or tissue-specific promoters include promoters, such as albumin that is liver specific [Pinkert et al, (1987) Genes Dev. 1:268-277], lymphoid specific promoters [Calame et al., (1988) Adv. Immunol. 43:235-275]; in particular promoters of T-cell receptors [Winoto et al., (1989) EMBO J. 8:729-733] and immunoglobulins; [Baneji et al (1983) Cell 33729-740], neuron-specific promoters, such as the neurofilament promoter [Byrne et al (1989) Proc. Natl. Acad. Sci. USA 86:5473-5477], pancreas-specific promoters [Edlunch et al. (1985) Science 230:912-916] or mammary gland-specific promoters, such as the milk whey promoter (U.S. Pat. No. 4,873,316 and European Application Publication No. 264,166). The nucleic acid construct of the present invention can further include an enhancer, which can be adjacent or distant to the promoter sequence and can function in up regulating the transcription therefrom.

The nucleic acid construct of the present methodology preferably further includes an appropriate selectable marker and/or an origin of replication. Preferably, the construct utilized is a shuttle vector, which can propagate both in *E. coli* (wherein the construct comprises an appropriate selectable marker and origin of replication) and be compatible for propagation in cells, or integration in a gene and a tissue of choice. The construct according to the present invention can be, for example, a plasmid, a bacmid, a phagemid, a cosmid, a phage, a virus or an artificial chromosome.

Currently preferred in vivo nucleic acid transfer techniques include transfection with viral or non-viral constructs, such as adenovirus, lentivirus, Herpes simplex I virus, or adeno-associated virus (AAV) and lipid-based systems. Useful lipids for lipid-mediated transfer of the gene are, for example, DOTMA, DOPE, and DC-Chol [Tonkinson et al., Cancer Investigation, 14(1): 54-65 (1996)]. The most preferred constructs for use in gene therapy are viruses, most preferably adenoviruses, AAV, lentiviruses, or retrbviruses. A viral construct, such as a retroviral construct includes at least one transcriptional promoter/enhancer or locus-defining element(s), or other elements that control gene expression by other means, such as alternate splicing, nuclear RNA export, or post-translational modification of messenger. Such vector constructs also include a packaging signal, long terminal repeats (LTRs) or portions thereof, and positive and negative strand primer binding sites appropriate to the virus used, unless it is already present in the viral construct. In addition, such a construct typically includes a signal sequence for secretion of the peptide or antibody from a host cell in which it is placed. Preferably the signal sequence for this purpose is a mammalian signal sequence. Optionally, the construct may also include a signal that directs polyadenylation, as well as one or more restriction sites and a translation termination sequence. By way of example, such constructs will typically include a 5' LTR, a tRNA binding site, a packaging signal, an origin of second-strand DNA synthesis, and a 3' LTR or a portion thereof. Other vectors can be used that are non-viral, such as cationic lipids, polylysine, and dendrimers.

The peptides or the nucleic acid construct encoding same of the present invention can be provided to an individual per se, or as part of a pharmaceutical composition where one peptide or more is mixed with a pharmaceutically acceptable carrier.

As used herein a "pharmaceutical composition" refers to a preparation of one or more of the active ingredients described herein with other chemical components, such as physiologically suitable carriers and excipients. The purpose of a pharmaceutical composition is to facilitate administration of a compound to an organisnm.

Herein the term "active ingredient" refers to the peptide preparation or the nucleic acid construct encoding same, which is accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases. One of the ingredients included in the pharmaceutically acceptable carrier can be for example polyethylene glycol (PEG), a biocompatlble polymer with a wide range of solubility in both organic and aqueous media (Mutter et al. (1979).

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedulary injections as well as intrathecal, direct intraventricular, intravenous, inrtaperitoneal, intranasal, or intraocular injections.

Alternately, one may administer a preparation in a local rather than systemic manner, for example, via injection of the preparation directly into a specific region of a patient's body.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the invention may be formulated in aqueous solutions, preferably in physiologically compatible buffers, such as Hank's solution, Ringer's solution, or physiological salt buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers, such as sugars, including lactose, sucrose, mannitol, or sorbitol; cellulose preparations, such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers, such as polyvinylpyrrolidone (PVP). If desired, disintegrating agents may be added, such as cross-linked polyvinyl pyrrolidone, agar, or alginic acid or a salt thereof, such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler, such as lactose, binders, such as starches, lubricants, such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichlorotetrafluoroethane or carbon dioxide. In the case of a pressurized aerosol, the dosage unit may be determined by providing a valve to deliver a metered amount. Capsules and cartridges of; e.g., gelatin for use in a dispenser may be formulated containing a powder mix of the compound and a suitable powder base, such as lactose or starch The preparations described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents, such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils, such as sesame oil, or synthetic fatty acids esters, such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The preparation of the present invention may also be formulated in rectal compositions, such as suppositories or retention enemas, using, e.g., conventional suppository bases, such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients effective to prevent, alleviate or ameliorate symptoms of disease or prolong the survival of the subject being treated.

Determination of a therapeutically effective amount is well within the capability of those skilled in the art.

For any preparation used in the methods of the invention, the therapeutically effective amount or dose can be estimated initially from in vitro assays. For example, a dose can be formulated in animal models and such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. [See e.g., Fingl, et al., (1975) "The Pharmacological Basis of Therapeutics", Ch. 1 p.1].

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions including the preparation of the present invention formulated in a compatible pharmaceutical carrier may also be prepared, placed in an appropriate container, and labeled for treatment of an indicated condition.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

Due to their selective binding to endothelial cells, the peptides of the present invention can be used to target agents fused thereto to ECs and thus can also be used for treating, i.e., curing, preventing or substantially reducing symptoms of angiogenesis-dependent diseases which are characterized by hyper-vascularization. For example, such fusions which include drugs can be used to inhibit tumor growth by destruction of the tumor vasculature.

Examples of drugs which can be included in such compositions include, but are not limited to, toxins, such as enzymatically active toxins of bacterial, fungal, plant, or animal origin, or fragments thereof [e.g., diphteria toxin, exotoxin A chain of *Pseudomonas aeruginosa*, ricin A chain, abrin A chain, modeccin A chain, α-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes], radioisotopes (e.g., $^{125}$I, $^{131}$I, $^{90}$Y, $^{212}$Bi $^{198}$Re) and chemotherapeutic agents (e.g., alkylating agents, folic acid antagonists, anti-metabolites of nucleic acid metabolism, antibiotics, pyrimidine analogs, 5-fluorouracil, cisplatin, purine nucleosides, amines, amino acids, triazol nucleosides, or corticosteroids. Specific examples include, Adriamycin, Doxorubicin, 5-Fluorouracil, Cytosine arabinoside (i.e., Ara-C), Cyclophosphamide, Thiotepa, Busulfan, Cytoxin, Taxol, Toxotere, Methotrexate, Cisplatin, Melphalan, Vinblastine, Bleomycin, Etoposide, Ifosfamide, Mitomycin C, Mitoxantrone, Vincreistine, Vinorelbine, Carboplatin, Teniposide, Daunomycin, Carminomycin, Aminopterin, Dactinomycin, Mitomycins, Esperamicins (see U.S. Pat. No. 4,675,187), Melphalan, and other related nitrogen mustards. Also included in this definition are hormonal agents that act to regulate or inhibit hormone action on tumors, such as tamoxifen and onapristone.

Fusions between the peptides of the present invention and drugs can be generated using a variety of bifunctional protein-coupling agents, such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bisazido compounds (such as bis-(p-azidobenzoyl)hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin fusion can be prepared as described in Vitetta et al., Science, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the peptide. See WO94/11026; U.S. Pat. No. 6,426,400; Laske, D. W., Youle, R. J., and Oldfield, E. H. (1997) Tumor regression with regional distribution of the targeted toxin TF-CRM107 in patients with malignant brain tumors. Nature Medicine 3:1362-1368.

A growing body of evidence indicates that angiogenesis is essential to the progression of cancer. In fact, the extent of neovascularity is strongly correlated with metastases in primary breast carcinoma, bladder cancer, prostrate cancer, non-small cell lung cancer, cutaneous melanomas, and uterine cervix carcinoma [Ferrar N., Breast Cancer Research and Treatment 36: 127-137 (1995)]. Thus, assessing the angiogenic phenotype of tumors will provide a strong indication to disease outcome. Other diseases or conditions which are characterized by hypervascularization or hypovascularization include, but are not limited to, retinal neovascularization, neovascularization in atherosclerotic plaques, hemangiomas, arthritis, and psoriasis, as well as the diseases described hereinabove. See Folknan, J. New England J. of Med. 333:1757-63 (1995).

Thus, the ability of the peptides of the present invention to bind specifically to the cell-surface of endothelial cells, suggests the use thereof as potent detectors of vascularization. This may be important for detecting the presence of; assessing predisposition to, or monitoring progression of an angiogenesis-dependent diseases.

Thus, the present invention also envisages a method of detecting a presence or an absence of endothelial cells in a biological sample.

The method is effected by incubating the biological sample with a peptide of the present invention capable of binding to the cell-surface of endothelial cells and detecting the peptide, to thereby detect the presence or the absence of endothelial cells in the biological sample.

The biological sample utilized for detection is preferably a tissue sample such as a biopsy specimen. Methods of obtaining tissue biopsies from mammals are well known in the art (see Hypertext Transfer Protocol://World Wide Web dothealthatoz dotcom/healthatoz/Atoz/default dothtml).

At least one peptide of the present invention is contacted with the biological sample under conditions suitable for complex formation (i.e., buffer, temperature, incubation time etc.); suitable conditions are described in Example 1 of the Examples section.

Peptide-cell complexes within a biological sample can be detected via any one of several methods known in the art, which methods can employ biochemical and/or optical detection schemes.

To facilitate complex detection, the peptides of the present invention are highlighted preferably by a tag or an antibody. It will be appreciated that highlighting can be effected prior to, concomitant with or following complex formation, depending on the highlighting method. As used herein the term "tag" refers to a molecule, which exhibits a quantifiable activity or characteristic. A tag can be a fluorescent molecule including chemical fluorescers, such as fluorescein or polypeptide fluorescers, such as the green fluorescent protein (GFP) or related proteins (World Wide Webdotclontechdotcom). In such case, the tag can be quantified via its fluorescence, which is generated upon the application of a suitable excitatory light. Alternatively, a tag can be an epitope tag, a fairly unique polypeptide sequence to which a specific antibody can bind without substantially cross reacting with other cellular epitopes. Such epitope tags include a Myc tag, a Flag tag, a His tag, a leucine tag, an IgG tag, a streptavidin tag and the like.

It will be appreciated that the peptides of the present invention may also be used as potent detectors of endothelial cells in vivo. A designed peptide capable of binding endothelial cells, labeled non-radioactively or with a radio-isotope, as is well known in the art can be administered to an individual to diagnose the onset or presence of angiogenesis-dependent disease, discussed hereinabove. The binding of such a labeled peptide after administration to endothelial cells can be detected by in vivo imaging techniques known in the art.

It will be appreciated that such a detection method can also be utilized in an assay for uncovering potential drugs useful in inhibition or promotion of angiogenesis. For example, the present invention may be used for high throughput screening of test compounds (i.e., putative angiogenic molecules). Typically, the peptides of the present invention are radiolabeled, to reduce assay volume. The peptides are allowed to bind endothelial cells prior to, concomitant with or following binding of the test compound. A competition assay is then effected by monitoring displacement of the label by a test compound [Han (1996) J. Am. Chem. Soc. 118:4506-7 and Esler (1996) Chem. 271:8545-8].

Once a putative angiogenic molecule is identified it is further evaluated using angiogenesis assays which are well known in the art. Examples include, but are not limited to, the chick chorioallantoic membrane, rabbit cornea assay, sponge implant models, matrigel and tumor models (see also the assays described in the Examples section which follows).

The peptides of the present invention can be included in a diagnostic or therapeutic kilt For example, the peptides can be packaged in a one or more containers with appropriate buffers and preservatives and used for diagnosis or for directing therapeutic treatment. Thus, the peptides, for example, can be each mixed in a single container or placed in individual containers. Preferably, the containers include a label. Suitable containers include, for example, bottles, vials, syringes, and test tubes. The containers may be formed from a variety of materials, such as glass or plastic.

In addition, other additives, such as stabilizers, buffers, blockers and the like may also be added.

The peptides of such kits can also be attached to a solid support, such as beads, array substrate (e.g., chips) and the like and used for diagnostic purposes.

Peptides included in kits or immobilized to substrates may be conjugated to a detectable label, such as described hereinabove.

The kit can also include instructions for determining if the tested subject is suffering from, or is at risk of developing, a condition, disorder, or disease associated with disregulated angiogenesis.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Selection of Novel Potential Angiogenesis-Inducing Phage Display Peptides

Novel peptides that potentially induce angiogenesis were identified by positive affinity selection (i.e., biopanning) of a random phage display peptide library using human umbilical vein endothelial cells [HUVECs, ECs (the two abbreviations are used interchangeably throughout the document)], followed by Enzyme-Linked Immunosorbent Assay (ELISA) of positive phage clones to ECs.

Materials and Experimental Methods

Phage Display Peptide Library—The Random Phage Display Peptide Library employed in this study was purchased from New England Biolabs (NEB), Inc. (Beverly, Mass., USA). The phage display library is based on a combinatorial library of random peptide 12-mers fused to a minor coat protein (pIII) of M13 phage. The displayed 12-mer peptides are expressed at the N-terminus of pIII. The library consists of about $2.7 \times 10^9$ electroporated sequences amplified once to yield 20 copies of each sequence in 10 μl of phage suspension.

The phage display peptide library was screened by five rounds of positive affinity selection (biopanning) using differentially-treated ECs: a) ECs without treatment (under normoxia), b) ECs following 3 hours of hypoxia treatment, and c) ECs following 24 hours of hypoxia treatment. Each positive selection was preceded by a negative selection using human Peripheral Blood Lymphocytes (PBLs). Each round of biopanning was effected by elution of the bound phage with 0.2 M glycine-HCl and incubation of the unbound phages on the second EC plate. This procedure was executed three times. Phages of the three elution steps were pooled for the second round of biopanning and so on. After the fifth round of biopanning, 40 individual clones from each group of cells screened were isolated so that, in all, 120 individual clones were obtained.

Human Umbilical Vein Endothelial Cells (HUVECs)—HUVECs (ECs), were isolated by Collagenase digestion as previously described [Jaffe et al., J. Clin. Invest., 52(11): 2757-64, 1973]. ECs were cultured with M199 supplemented with 20% FCS, $10^4$ units of penicillin, 10 mg/ml of streptomycin sulfate, 10 mg/ml of neomycin sulfate (Biological Industries, Kibbutz Beit Haemek, Israel), 25 μg/ml of EC growth supplement (Biomedical Technologies, Inc., Stoughton, Mass., USA), and 5 U/ml of Heparin (SIGMA, Rehovot, Israel). HUVECs were harvested with Trypsin (0.25%), EDTA (0.05%, Biological Industries, Kibbutz Beit Haemek, Israel) and incubated on 60 mm petri dishes coated with 1% gelatin for 24 hours. Following incubation, cells were washed and incubated with M199 supplemented with 10% FCS. ECs were subjected to four different treatments: a) no treatment, b) 3 hours of hypoxia, c) 6 hours of hypoxia, or d) 24 hours of hypoxia. Subsequently, monolayers were washed with PBS and dried overnight. Cells were rehydrated with PBS containing 5% FCS and 0.1% sodium azide and maintained at 4° C. until biopanning.

Hypoxia treatment—ECs were subjected to hypoxia for 3, 6, or 24 hours in a gas mixture containing 94% $N_2$, 5% $CO_2$, and 1% $O_2$ in a hypoxia chamber (Billups-Rothenberg, Delmar, Calif., USA).

Screening of positive clones by ELISA—The binding of positive clones from each group was re-evaluated by ELISA. For this purpose, ECs under normoxic conditions, ECs following 3, 6, or 24 hours of hypoxia, or human PBL (as controls) were plated at $20 \times 10^3$ cells/well on 96 well plates. Plates were re-hydrated by overnight incubation at 4° C. in PBS supplemented with 3% BSA, followed by three washes with PBS. Phage from each of the 120 clones isolated were dispersed on the ELISA plates at concentrations of $10^{10}$, $10^9$, or $10^8$ phage per well and incubated for two hours at room temperature. Plates were then washed three times with PBS containing 0.05% Tween, followed by three washes with double distilled water (DDW). After washing, an anti-M13 HRP antibody (Amersham Pharmacia Biotech UK Limited, Buckinghamshire, UK) at a 1:5,000 dilution was added and incubated for 2 hours at room temperature ° C., following which the plates were washed 5 times in the presence of PBS and 0.05% Tween-20. The BRP reaction was carried out using 100 μl of tetramethyl benzidine liquid substrate (DAKO TMB substrate chromogen, DAKO Corporation, Carpinteria, Calif., USA) for a 15 minute-incubation following which the reaction was terminated by the addition of 50 μl of 1 M HCl. Plates were read at 450 nm in an ELISA reader (SLT 400ATC, SLT LAB Instruments, Austria).

Statistical and graphical methods—Statistical analysis was effected by analysis of variance (ANOVA) with appropriate post-hoc tests, generally Dunnett's, for a comparison to a control or Tukey-Kramer HSD for multiple comparisons. Results were considered statistically significant at $P<0.05$.

Results

EC-binding peptides were selected using phage display peptide library—A phage display peptide library was subjected to five rounds of positive affinity selections (biopanning) using ECs under physiological conditions (i.e., normoxia) or following hypoxia. The second step of selection of peptide-presenting phage was effected by ELISA using ECs and lymphocyte-coated plates as controls. Fifteen different peptide-presenting phages at a concentration of $10^9$ (FIG. 1a) and $10^{10}$ (FIG. 1b) phages per well were screened by ELISA on four different EC preparations (ECs at normoxic conditions and ECs following 3, 6, and 24 hours of hypoxia). FIG. 1a and Table 3 hereinbelow, illustrate selected peptides which exhibited statistically significant differences ($p<0.05$) between binding of NO phage (i.e., unmodified M13 phage) and binding of certain peptide-presenting phages as determined using ANOVA analysis of $10^9$ selected phage indicated

TABLE 3

| Peptide-presenting phage | |
|---|---|
| Peptide | Cells |
| SP | EC |
| SP | H3 |
| TR | EC |
| TR | H3 |
| TR | H6 |
| TR | H24 |
| VL | EC |
| VL | H3 |
| VL | H6 |
| VL | H24 |
| YR | EC |
| YR | H3 |
| YR | H6 |
| YR | H24 |

Table 3:
Peptide-presenting phage selected from EC (ECs at normoxic conditions), H3 (ECs following 3 hours of hypoxia), H6 (ECs following 6 hours of hypoxia), and H24 (ECs following 24 hours of hypoxia).
$P < 0.05$.

Similarly, statistically significant peptides which were selected using ANOVA analysis performed on $10^{10}$ phages ($p<0.05$) are shown in FIG. 1b.

Altogether, these findings demonstrate the identification of specific peptide-presenting phages which are capable of specifically binding ECs under either normoxia or hypoxia Example 2

Selected Peptide-Presenting Phages are Capable of Inducing Angiogenesis In Vitro The ability of selected peptide-presenting phages to induce angiogenesis in vitro was evaluated by inducing EC proliferation, migration or sprouting of aortic rings.

Materials and Experimental Methods

Identification of DNA sequences from selected peptide-presenting phages—DNA from all isolated selected clones was purified by incubation with iodide buffer and ethanol according to the manufacturer's instructions (NEB, Beverly, Mass., USA). This rapid procedure produces template of sufficient purity for automated DNA sequencing with dye-labeled dideoxynucleotides. The 96 gIII (NEB) sequencing primer was utilized for automated DNA sequencing by the Sequencing Unit of Tel Aviv University, Tel Aviv, Israel.

ECs and hypoxia treatment—ECs were isolated, cultured, and subjected to hypoxia treatments as described in Example 1, hereinabove.

EC proliferation assay—ECs ($40 \times 10^3$ cells/well) were seeded on 24-well plates coated with 1% gelatin and were further cultured in the presence of M199 medium supplemented with 20% FCS, $10^4$ units of penicillin, 10 mg/ml of streptomycin sulfate, 10 mg/ml of neomycin sulfate (Biological Industries, Kibbutz Beit Haemek, Israel), 25 μg/ml of endothelial cell growth supplement (Biomedical Technologies, Inc., Stoughton, Mass., USA) and 5 U/ml of heparin (SIGMA, Rehovot, Israel). After 24 hours, cells were washed with serum-free medium (SFM) and incubated with SFM for another 24 hours at 37° C. Subsequently, $10^6$ selected phages were added per well and plates were incubated for another 24 hours. Abortive phages (those lacking a cloned peptide) were used as negative controls and were designated NO. Two μCi/well of [$^3$H]-Thymidine (SIGMA, Rehovot, Israel) were added for the last 6 hours of incubation, following which the cells were fixed for 16 hours with 10% TCA at 4° C. and washed with absolute ethanol. For cell lysis, NaOH (300 μl of 0.5 M per well) was added to the cells for a 15-minute incubation at 37° C., following which cell lysates were transferred to scintillation vials containing 2 ml of scintillation liquid (Ultima Gold, Packard Bioscience, Meriden, Conn., USA) and counted cpm/min in a β counter (Scintillation β Counter 1600 TR, Packard A Camberra Company, Meriden, Conn., USA).

EC migration assay—EC migration was evaluated by the Chemicon QCM 96-well Migration Assay (Chemicon International, Temecula, Calif., USA) according to the manufacturer's instructions. Briefly, the kit's migration chamber comprises an insert membrane with 8 μm pores and a feeder tray containing the peptides as chemoattractants. Cell migration was evaluated by placing the cells in the migration chamber and following their migration to the bottom of the membrane.

For the migration/chemoattractant assay, ECs from passage 3 were incubated for 24 hours on gelatin-coated plates in the presence of the M199 SFM. Following trypsinization, $2 \times 10^4$ ECs were incubated for 5 hours in each of the 96 wells of the migration chamber. The peptide-presenting phages ($10^5$ or $10^6$) were added to the feeder tray to chemoattractant the cells without being in physical contact with the cells. Cells which reached the bottom of the membrane (i.e., migratory cells) were dissociated from the membrane following the incubation with a cell detachment buffer. The migratory cells were subsequently lysed and detected by the molecular probe CyQuant GR dye which exerts green fluorescent enhancement when bound to cellular nucleic acid.

For activation migration assays, $10^5$ or $10^6$ peptide-presenting phages were incubated (for 5 hours) with ECs in the migration chamber. NO phages (unmodified M13 phages) served as negative control in both migration assays. Results were determined by a fluorescent ELISA reader at 480/520 nm (Fluostar BMG Lab Teck) and are presented in net values from which the control values were subtracted.

Aortic ring formation assay—Adventitia of human mammary or radial artery was stripped and cut into 1 mm long rings. The bottom of each well of a sterile 96-well plate was coated with 20 μg of fibronectin (Biological Industries, Kibbutz Beit Haemek, Israel) and the rings were positioned in the center of each well containing 150 ml of Dulbecco's modified Eagle's medium (DMEM, Biological Industries) supplemented with 10% FCS. For aortic ring formation, $10^6$ peptide-presenting phages were added to each well and the plates were incubated for 7 days in the presence of 5% $CO_2$ at 37° C. Unmodified M13 phages (NO) were used as negative controls. Arterial rings were removed and the extent of cell proliferation was estimated using the XTT assay (biological Industries) according to the manufacturer's instructions.

Experimental Results

Characterization of identical EC-binding peptides from various EC-treated cells—DNA sequence analysis of the cloned regions of the positively selected peptide-presenting phages revealed the presence of identical clones among the various ECs. Moreover, some peptide-presenting phages (e.g., VL, LP, TR) were common in both cells grown under normoxia (EC) and cells grown under hypoxia (H24). Other peptide-presenting phages, e.g., YR or LT, were from ECs exposed to 3 or 24 hours of hypoxia, respectively. On the other hand, while SP was common to ECs exposed to 3 and 24 hours of hypoxia, others (e.g., ST, QF, NS), were from ECs grown under nomoxia (Table 4, hereinbelow).

TABLE 4

Number of identical sequences obtained from positively-selected peptide-presenting phages

| Peptide | EC | H3 | H24 |
| --- | --- | --- | --- |
| VL | 22 | — | 10 |
| LP | 2 | 29 | 9 |
| TR | 2 | — | 2 |
| ST | 2 | — | — |
| QF | 4 | — | — |
| NS | 2 | — | — |
| SP | — | 3 | 2 |
| YR | — | 2 | — |
| LT | — | — | 4 |
| HR | — | — | 3 |
| HY | — | — | 2 |
| TP | — | — | — |
| NR | — | — | — |
| SA | — | — | — |

Table 4:
The number of identical clones present in positively-selected peptide-presenting phages from EC (ECs under normoxic conditions), H3 (ECs following 3 hours of hypoxia), or H24 (ECs following 24 hours of hypoxia).

Peptide-presenting phages are capable of inducing EC proliferation and migration—Six individual clones (VL, LT, QF, SP, YR, and TR) were tested using the Chemicon QCM 96-well Migration Assay for the capacity of the presented peptides to induce EC proliferation and migration. The DNA and protein sequences of the selected peptides are displayed in Table 5, hereinbelow.

TABLE 5

Sequences of selected peptides and nucleic acid encoding same

| PeptideID # | Nucleic acid sequence (SEQ ID) | Amino acid sequence (SEQ ID) |
| --- | --- | --- |
| VL | GTTCCGTGGATGGAGCCGGCTTATCAGAGGTTTCTG (SEQ ID NO:1) | VPWMEPAYQRFL (SEQ ID NO:2) |
| LT | CTGCTTGCGGATACGACGCATCATAGGCCGTGGACT (SEQ ID NO:3) | LLADTTHHRPWT (SEQ ID NO:4) |
| QF | CAGCCTTGGTTGGAGCAGGCTTATTATAGTACGTTT (SEQ ID NO:5) | QPWLEQAYYSTF (SEQ ID NO:6) |
| SP | TCTGCGCATGGGACGTCTACTGGTGTTCCGTGGCCG (SEQ ID NO:7) | SAHGTSTGVPWP (SEQ ID NO:8) |
| YR | TATCCGCATATTGATTCGCTTGGTCATTGGCGGCGG (SEQ ID NO:9) | YPHIDSLGHWRR (SEQ ID NO:10) |

TABLE 5-continued

Sequences of selected peptides and nucleic acid encoding same

| PeptideID # | Nucleic acid sequence (SEQ ID) | Amino acid sequence (SEQ ID) |
|---|---|---|
| TR | ACTTTGCCGTGGCTGGAGGAGTCTTATTGGCGTCCT (SEQ ID NO:11) | TLPWLEESYWRP (SEQ ID NO:12) |

Table 5: Presented are the amino acid sequences of the selected peptides and the nucleic acid sequences encoding same.

As is shown in FIG. 2, all six selected peptide-presenting phages induced (at a concentration of $10^6$/well) increased proliferation of ECs as compared with the unmodified, empty, phages (NO).

The selected peptide-presenting phages are capable of inducing EC migration—The ability of the peptide-presenting phages to induce EC migration of activated ECs was tested by placing the peptide-presenting phages with the ECs in migration chambers. Two of the tested peptide-presenting phages. (QF and LT) induced migration of the activated ECs at a concentration of $10^5$ (FIG. 3a) or $10^6$ (FIG. 3b) phages per well. On the other hand, placement of the peptide-presenting phages at two different concentrations on the feeder tray revealed the ability of YR (of the six peptide-presenting phages) to induce migration as chemoattractants at $10^5$ phages per well (FIG. 4a), and the ability of QF, SP, TR and LT to induce migration as chemoattractants at a concentration of $10^6$ phages per well (FIG. 4b).

Aortic ring sprouting by peptide presenting phages—Aortic rings were tested for sprouting in the presence of peptide-presenting phages. FIG. 5 demonstrates proliferation of cells originating from the aortic rings, induced by peptide presenting phages. ANOVA analysis comparing the six peptide-presenting phages indicated an overall clear difference in the proliferation of cells derived from the aortic rings (P=0.0003). In addition, post-hoc tests indicated statistically significant differences between the VL peptide-presenting phage and the S24 empty phage control (i.e., NO).

These results demonstrate that the peptide-presenting phages of the present invention are capable of inducing EC migration and proliferation, i.e., are capable of inducing angiogenesis in vitro.

Example 3

Synthetic Peptides are Capable of Inducing Angiogenesis In Vitro Under Normoxic Conditions Peptides corresponding to the selected peptide-presenting phages were synthesized and their potential to induce angiogenesis in vitro was evaluated, as follows.

Materials and Experimental Methods

Peptide synthesis—Peptides were synthesized by SynPep (Dublin, Calif., USA). HPLC purity analysis demonstrated that the purity of each synthetic peptide was higher than 97%. Peptide QF was dissolved in 50% water/50% acetonitrile. All other peptides were dissolved in water.

Fluorescein labeling of synthetic peptides—Fluorescein Isothiocyanate (FTIC, Pierce, Rockford, Ill.) is an amino-reactive probe that reacts in an alkine environment with primary amines to form a stable fluorescent derivative. 12.5 µl of FITC (10 mg/ml) were added per 1 mg of peptide diluted in 0.5 M bicarbonate buffer (pH 9.5) and agitated in the dark for 2 hours. 0.1 ml of 1.5 M hydroxilamine was then added per 1 ml of reaction mixture and agitated for an additional 30 minutes at room temperature. Unbound FITC was removed by dialysis in the presence of PBS.

Peptide binding to ECs—ECs were cultured in M199 supplemented with 10% FCS. For peptide binding assays, the cells were trypsinized and $10^5$ cells were suspended in PBS supplemented with 5% FCS and 0.1% sodium azide. Cells were incubated for 2 hours (on ice, in the dark) in the presence of 1-6 µg of FITC-labeled peptides, following which the stained cells were washed twice with PBS. Samples were analyzed by FACS (FACScan, Becton Dickinson, San Jose, Calif., USA). For control, $0.5 \times 10^6$ of PBLs were utilized.

Proliferation of ECs in the presence of synthetic peptides—ECs were incubated in the presence of EBM-2 medium containing supplements (Cambrex BioWhittaker Cell Biology Products, Walkersville, USA). Cells were passaged every 3 days by harvesting cells with 0.25% Trypsin/0.05% (Biological Industries) and re-plating the cells at a concentration of $10^4$ cells per a 25 $cm^2$ flask. ECs from passage 3 were used for proliferation experiments.

ECs ($12 \times 10^3$ cells/well) were seeded on 24-well plates in EBM-2 medium containing supplements. Following a 24-hours incubation, cells were subjected to 24 hours of starvation in supplements-free medium (SFM). Synthetic peptides (SP, LT, TR, and VL) were each added at concentrations of 0.05, 0.1, 1, 10, or 100 ng/ml for 24 hours. For a proliferation assay, 2 µCi/well of [$^3$H]-Thymidine (SIGMA, Rehovot, Israel) were added for a 6-hour incubation, following which the plates were washed 3 times with PBS. For cell lysis, the plates were incubated for 15 minutes at 37° C. with 300 µl/well of 0.5 M NaOH. Subsequently, cell lysates were transferred to scintillation vials containing 2 ml of scintillation liquid (Ultima Gold, Packard Bioscience, Meriden, Conn., USA) and counted (cpm/min) in a β counter (Scintillation β Counter 1600 TR, Packard A Camberra Company, Meriden, Conn., USA).

Proliferation of dermal microvascular endothelial cells (MVECs) in the presence of synthetic peptides—MVECs were incubated with synthetic peptides (LT, SP, and YR) as described above for HUVECs (ECs), except that the MVECs were seeded in EBM-MV medium containing supplements (Cambrex BioWhittaker Cell Biology Products) and MVECs from passage 4 (rather than 3) were used for proliferation experiments.

Migration assays in the presence of synthetic peptides—EC migration was evaluated as described in Example 2, hereinabove. Following typsinization, ECs ($25 \times 10^3$) were incubated in migration chambers. For the chemoattractant migration assay, synthetic peptides were added to the feeder tray at 5, 10, 20, and 50 ng/ml and incubated with the cells for 5 or 15 hours. For migration activation assays, synthetic peptides at 0.1, 1, and 10 ng/ml were incubated with the cells in the migration chamber for 5 or 15 hours.

MVEC migration was evaluated as described above except that MVECs from passage 3 were incubated in EBM-MV SFM. Synthetic peptides were added at 10 ng/ml to the feeder tray for chemoattractant migration assay as well as for activation of migration assays. The presence of migratory cells was detected using the fluorescent ELISA reader at 480/520 nm (Fluostar BMG Lab Teck) as described in Example 2, hereinabove.

Sprouting of aortic rings by synthetic peptides—Human mammary or radial artery was prepared in a 96-well plate as described in Example 2, hereinabove. Peptides were added in increasing concentrations (1, 10, 100, and 1,000 ng/ml) to each well containing the aortic ring. Plates were incubated at 37° C. in the presence of 5% $CO_2$ for 7 days. Arterial rings were removed and cell proliferation was assessed using the XTT assay (Biological Industries) according to the manufacturer's instructions.

Tube formation assay—ECs from passage 3 or MVECs from passage 4 were harvested with trypsin and incubated for 24 hours in SFM. Twenty-four—well plates were pre-coated with 250 µl of Cultrex Basement Membrane Extract with reduced growth factors (R&D Systems, Minneapolis, Minn., USA). Five hundred microliters of medium containing $10^6$ cells were transferred to the coated wells. Synthetic peptides, FGF, YR, QF, or VL were added to ECs, and VEGF, YR, QF, or VL were added to MVECs at 10 ng/ml. Plates were incubated for 24 hours at 37° C. in the presence of 5% $CO_2$. HUVECs and MVECs were photographed under a light microscope at 20 hours and 8 hours, respectively.

Real Time PCR—MVECs from passage 3 were incubated for 24 hours in EBM-MV supplement-free medium (starving media). Following starvation, 1 ng/ml of synthetic peptides LT, QF, SP, TR, YR, and VL and 10 ng/ml of VEGF were added to the plates. Following 1.5 or 6 hours of incubation, total RNA was extracted using TRIsol reagent (Invitrogen Life Technologies, Carlsbad Calif., USA) and 0.8 µg of the extracted RNA was used as a template for reverse transcription (Invitrogen) using random primers (SuperScript III First-Strand Synthesis System for RT-PCR (hvitrogen, Carlsbad Calif., USA) according to the manufacturer's instructions.

Resulting cDNAs were subjected to real time PCR amplification using the ABI prism 7000 Sequence Detection System (Applied Biosystems, Foster City, Calif., USA). Oligonucleotide primers were designed using Primer Express Software (Applied Biosystems, Foster City, Calif., USA) according the translated region of VEGF-A (Accession No:NM_003376), VEGF-C (Accession No:NM_005429), KDR (Accession No:NM_002253), FLT-1 (Accession No:NM_002019), HIF-α (Accession No:HSU22431), and GAPDH (Accession No:NM_002046) and are listed in Table 6, hereinbelow. Briefly, a reaction mixture of 20 µl consisting of DDW, oligonucleotide primers (500 nM), cDNA (3 µl), and SYBR Green PCR master kit (Applied Biosystems, Foster City, Calif., USA) was subjected to an amplification program of 15 seconds at 95° C., and 60 seconds at 60° C. for 40 cycles. Results were analyzed using the Sequence Detector Software Version 1 (Applied Biosystenis).

TABLE 6

Oligonucleotide primers for amplification of selected genes cDNA

| Gene name | Sense primer (SEQ ID) | Anti-sense primer (SEQ ID) |
|---|---|---|
| VEGF-A | CTACCTCCACCATGCCAAGTG (SEQ ID NO:15) | TGCGCTGATAGACATCCATGA (SEQ ID NO:16) |
| VEGF-C | TTCCTGCCGATGCATGTGTA (SEQ ID NO:17) | TGTTCGCTGCCTGACACTGT (SEQ ID NO:18) |
| KDR | TCAGGCAGCTCACAGTCCTAGAG (SEQ ID NO:19) | ACTTGTCGTCTGATTCTCCAGGTT (SEQ ID NO:20) |
| FLT-1 | TCAGCGCATGGCAATAATAGA (SEQ ID NO:21) | ACCAAGGTGCTAGCCATCTTATTC (SEQ ID NO:22) |
| HIF-α | AGTGTACCCTAACTAGCCGAGGAA (SEQ ID NO:23) | GCCTGTGCAGTGCAATACCTT (SEQ ID NO:24) |
| GAPDH | GTCGGAGTCAACGGATTTGG (SEQ ID NO:25) | GGCAACAATATCCACTTTACCAGAGT (SEQ ID NO:26) |

Statstcal and graphical methods—See Example 1, hereinabove.

Experimental Results

Synthetic peptides bind ECs in vitro—Six synthetic peptides LT, QF, SP, TR, VL, and YR (displayed in Table 5) were synthesized in order to evaluate their ability to induce angiogenesis in vitro and in vivo. Specific binding of the above-described synthetic peptides to ECs was tested. The peptides were FITC-labeled and binding to ECs was analyzed by FACS. As is shown in FIGS. 6a-i and FIG. 7, the synthetic peptides bound specifically to ECs but not to lymphocytes (PBLs). Increasing concentrations of peptides (FIGS. 6c-i, red lines) resulted in increased binding to ECs (94-96% binding) relative to a lower concentration (FIGS. 6c-i, green lines).

Synthetic peptides are capable of inducing proliferation under normoxia—Synthetic peptides were assayed for their effect on proliferation of HUVECs under normoxic conditions. ECs were seeded on 24 well plates in SFM for 24 hours and then synthetic peptides were added at increasing concentrations for an additional 24 hours. A significant dose-dependent increase in [$^3$H]-Thymidine uptake was observed in ECs incubated with the LT, SP, TR, and VL peptides (FIG. 8a). Peptides LT, TR, and SP, at 10 ng/ml each, induced the highest proliferative response, leading to 1.7, 1.8, and 1.6-fold increases, respectively. On the other hand, VL, at 1 ng/ml, induced the highest proliferative response leading to a 1.8 fold increase.

A significant increase in [$^3$H]-Thymidine uptake was also demonstrated for MVECs incubated with LT, SP or YR (FIG. 8b). The increase was in a dose dependent manner with the highest proliferation response in a concentration of 1 ng/ml for all three peptides. At this concentration, LT YR and SP increased MVECs proliferation response by 1.8, 1.7 and 1.4 fold, respectively (FIG. 8b).

Cells migration by synthetic peptides—To test the effect of the synthetic peptides on EC cell migration, synthetic peptides at concentrations of 5, 10, 20, and 50 ng/ml were added to the feeder tray. A dose-dependent induced migration was observed for LT (FIG. 9a) and SP (FIG. 9b). The effect appears to reach a plateau at high concentrations, which would be predicted based on pharmacokinetics. The exact pharmacologic profile of this attraction requires further study. A smaller effect of induced migration was noted for VL and TR when used as chemoattractants (FIG. 9c).

The synthetic peptides are capable of activating migration of EC cells—To further test the effectiveness of the synthetic peptides in activating migration, the synthetic peptides were incubated with the ECs in the migration chambers. FIG. 10 illustrates that each of these peptides, within a 5 hours span, induces statistically significantly more ECs migration than control ECs without the peptide present. By 15 hours, however, the migration of cells has been reduced, so that no statistical difference is seen between any peptide-treated cells and control epithelial cells (FIG. 10).

MVECs were also shown to migrate due to synthetic peptides induction. The experiment performed with the test peptides demonstrated their effectiveness as chemoattractants to induce migration of MVECs in a dose dependent manner. FIG. 11a illustrates that each of the test peptides, within a 5 hours span, induced more cell migration than control endothelial cells without the peptide present (results are in net values from which the control values were subtracted). At 10 ng/ml, LT, QF, YR SP, TR and VL induced a 3.5, 2.4, 2.4, 2, 2, and 2-fold increase in MVECs migration respectively.

MVECs were also directly activated. by the synthetic peptides. TR, SP, QF, and YR were all shown to induce MVECs migration (by 2.6, 2.1, 2.3 and 1.8 folds, respectively), at 1 ng/ml (FIG. 11b).

Aortic rings sprouting by synthetic peptides—As described before for the peptide-presenting phages, aortic rings induced sprouting was evaluated by addition to the cultured aortic rings purified synthetic peptides at different concentrations. Four peptides (QF, YR, LT, and VL) were compared for their ability to induce cell proliferation in aortic rings. Clear differences between the peptides (after correction for control optical density) were observed at the noted peptide concentrations (FIG. 12).

Figure 13G:
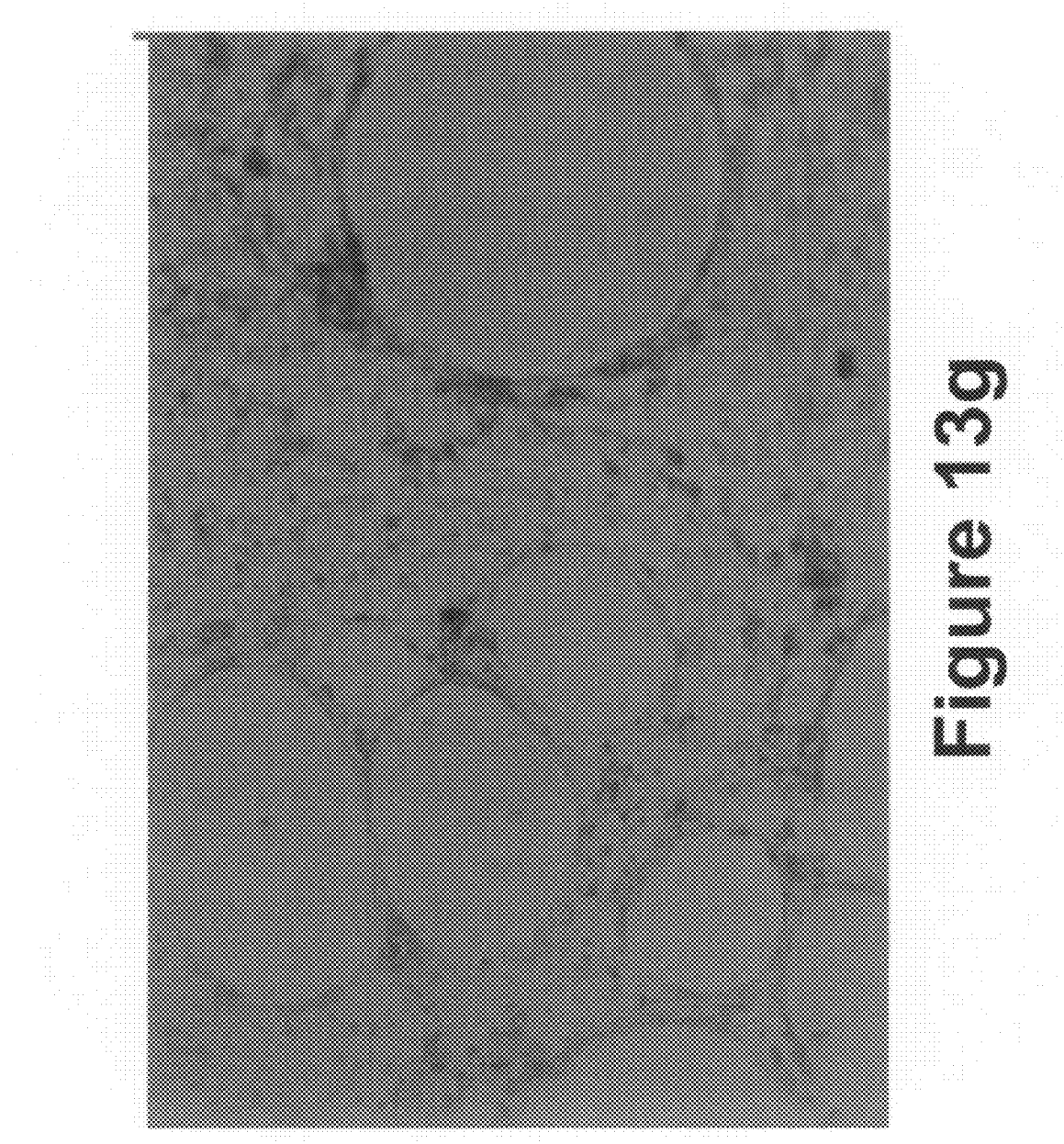
Figure 13I:
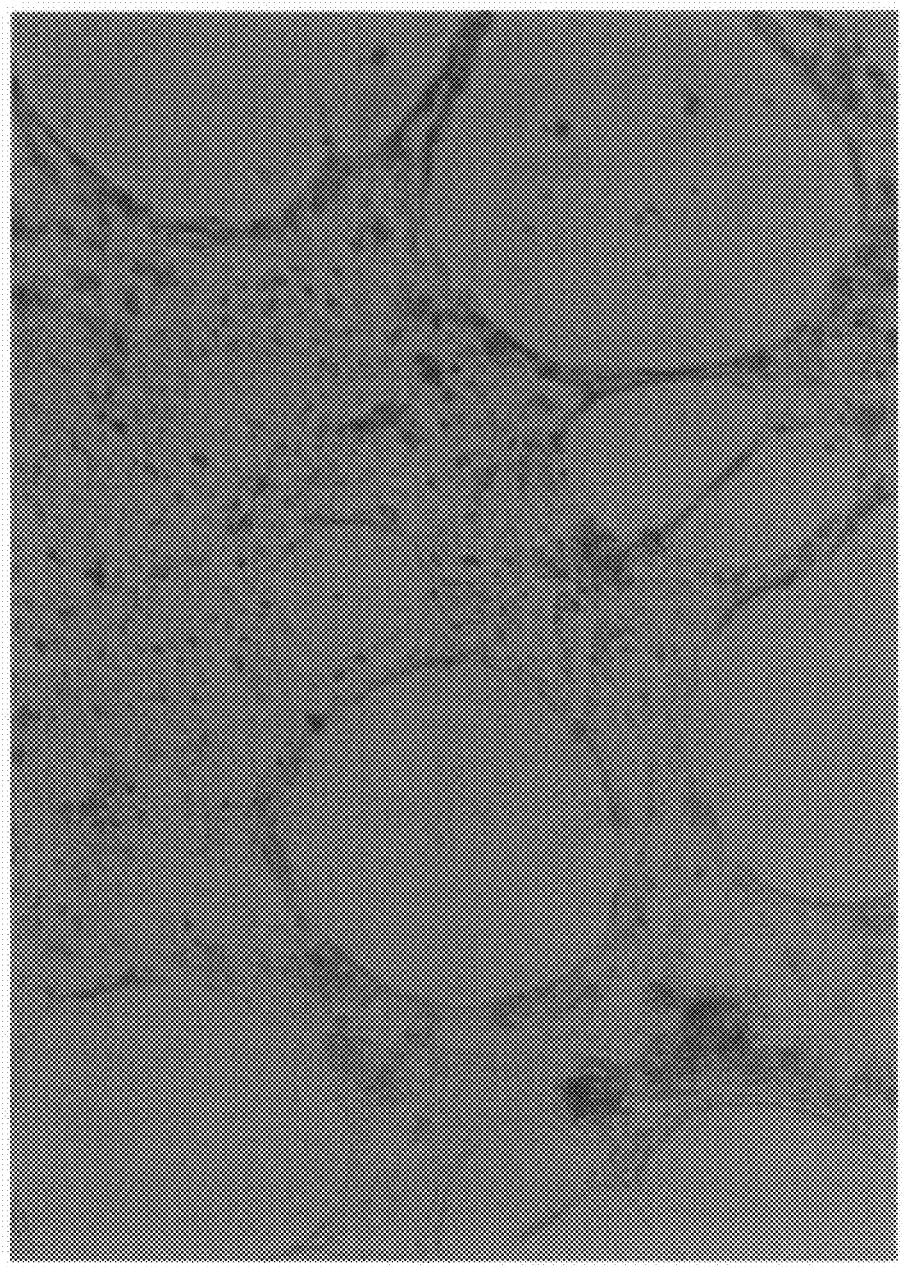
Figure 13J:
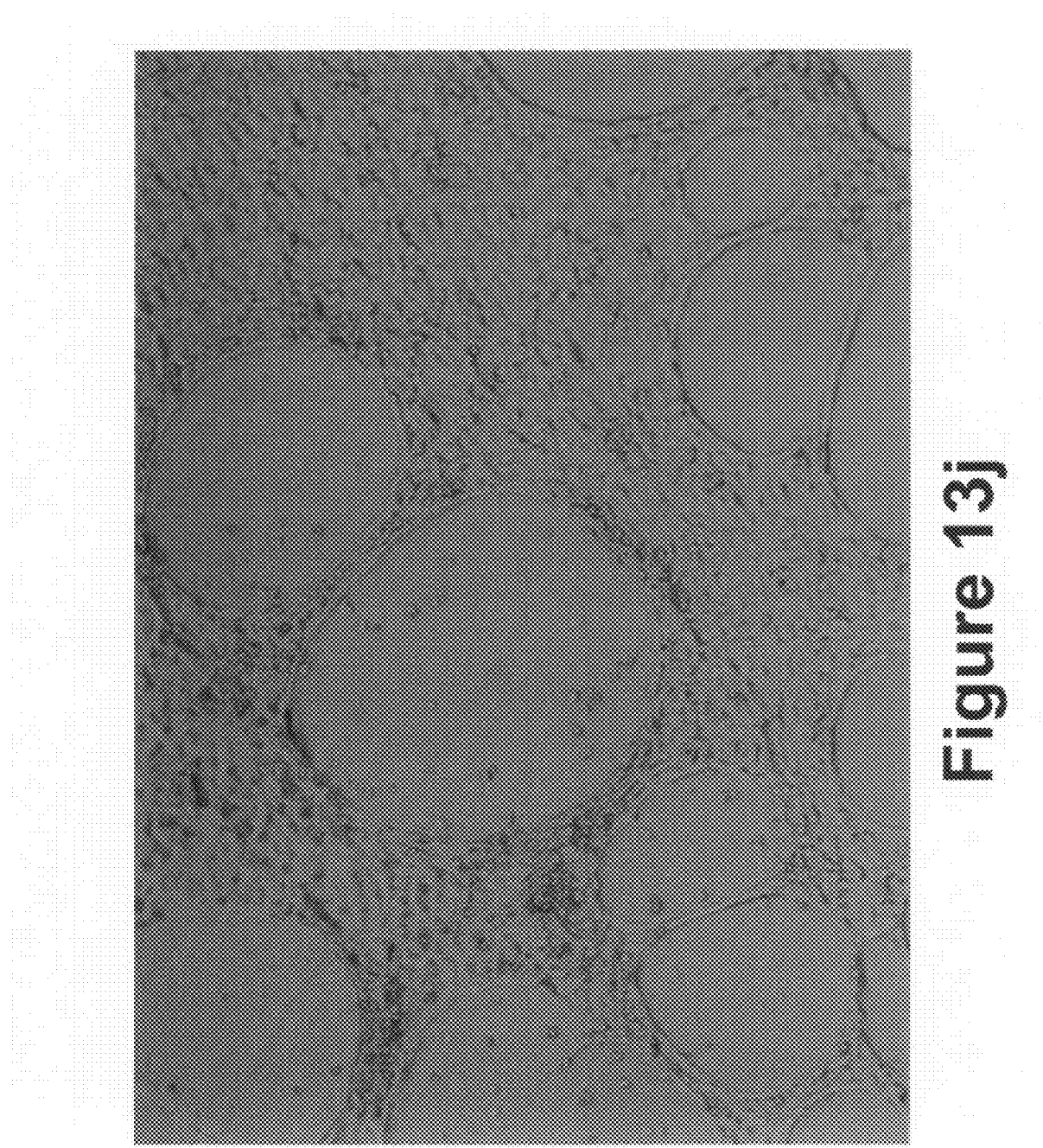

Tube Formation—ECs and MVECs were incubated on matrigel in the presence of peptides and array formation was analyzed. Peptides (YR, QF and VL) added to MVECs at concentration of 10 ng/ml, resulted in a significant increase in tube formation (FIGS. 13c-e) as compared to untreated cells (FIG. 13a). This increase was similar to the effect of VEGF on these cells (FIG. 13b). The same effect of increased tube formation was induced by these peptides when added to ECs (FIG. 13h-j) as compared to untreated cells (FIG. 13f). This increase was similar to the effect of FGF on ECs (FIG. 13g).

As described for the peptide-presenting phages, the synthetic peptides produced, could-induce in vitro angiogenic effects in ECs. In all angiogenic effects tested, at least one (while in most cases more) of the synthetic peptides tested showed significant effect over control. These results indicate that these peptides may be also capable of in vivo angiogenesis.

Peptides effect on gene expression in MVECs—The effect of the synthetic peptides on the expression in MVECs of selected genes (VEGF-A, VEGF-C, KDR, FLT-1 and HIF-1α) related to the VEGF pathway (a major pathway that participated in angiogenic process) was tested. Synthetic peptides were added at 1 ng/ml for 1.5 and 6 hours. After incubation with peptide, RNA was extracted from MVECs and Real Time PCR was performed. Gene expression was calculated as peptide/control (cells without peptide treatment) ratio.

The different peptides exhibited varying effects on the expression of the genes tested as demonstrated in FIGS. 14a-e and summarized in Table 7, hereinbelow.

TABLE 7

The effect of the different peptides on gene expression

| Gene | Synthetic peptide | Expression after 1.5 hours | Synthetic peptide | Expression after 6 hours |
|---|---|---|---|---|
| VEGF-A (FIG. 14a) | QF, TR, YR, VL, LT, SP | + | VL QF, TR, YR | + − |
| VEGF-C (FIG. 14b) | QF, TR, VL, LT, SP | + | QF, TR, VL, LT, SP | + |
| FLT-1 (FIG. 14c) | QF, TR, YR, VL, LT, SP | + | QF, YR | − |
| KDR (FIG. 14d) | QF, SP, YR LT | + − | TR, VL YR | + − |
| HIF (FIG. 14e) | QF, TR, VL LT, YR | + − | TR, VL LT, QF | + − |

Table 7:
The increased (+) or non-increased (−)gene expression is presented for the noted genes as a result of incubation with the noted synthetic peptides.

As is shown in Table 7 hereinabove, all 6 peptides tested were shown to induce the expression of some of the genes tested. These results may lead to the molecular mechanism by which these peptides induce angiogenesis.

Example 4

The Effect of Hypoxia on In Vitro Induced Angiogenesis by Synthetic Peptides

The ability of selected peptides to induce angiogenesis was evaluated by induction of cell binding, proliferation, migration and tube formation assays under hypoxic condition.

Materials and Experimental Methods

Peptides synthesis and Fluorescein labeling—See Example 3, hereinabove.

ECs and hypoxia conditions—ECs were isolated, cultured, and subjected to hypoxia conditions as described in Example 1, hereinabove.

FACS analysis of peptide binding to ECs with and without hypoxia treatment—ECs were exposed to hypoxia conditions and then prepared for FACS analysis as described in Example 3, hereinabove. Cells were stained with 6 μg of SP or LT labeled peptide. Samples were analyzed by Fluorescence Activated Cell Sorter (FACScan Beckton Dickinson, Calif., USA).

Synthetic peptides induced proliferation or migration after and under hypoxia treatment—Cell proliferation or migration assays were performed as described in Example 3, hereinabove, except that cells were divided to 3 groups: control cells, cells after exposure to hypoxia conditions or cells proliferating under hypoxia conditions. For cell proliferation assays, ECs were incubated with QF, LT and SP and MVECs were incubated with LT, SP, and YR. For cell migration assays, ECs were incubated with EBM-2 and MVECs were incubated with EBM-MV media.

Tube formation assay after and under hypoxia treatment—Tube formation assay was performed as described in Example 3, hereinabove, except that the cells were divided to 3 groups: control cells, cells after exposure to hypoxia conditions, and cells on matrigel basement that form tubes under hypoxia treatment.

Statistical and graphical methods—was performed as described in Example 1, hereinabove.

Experimental Results

Synthetic peptides bind to ECs after hypoxia treatment—Peptide binding assays were performed on ECs grown under normoxia or ECs following hypoxia. As is shown in FIGS. 15 and 16a-b, while LT and SP exhibited increased binding to ECs exposed to hypoxia, the other peptides (i.e., QF, TR, VL and YR) exhibited similar intensity of binding to ECs under both conditions.

Synthetic peptides induced proliferation under and following hypoxia treatment—The effect of synthetic peptides (QF, LT and SP) on proliferation of ECs was tested under and following hypoxia treatment as compared to control. ECs were seeded on 24 well plates in serum free media for 24 hours, following which synthetic peptides were added to cells in various concentrations for additional 24 hours.

FIGS. 17a-b demonstrate a significant dose-dependent increase in [$^3$H]-Thymidine uptake in ECs incubated with the LT and SP peptides under and following hypoxia. As is shown in FIG. 17a, while LT (at a concentration of 10 ng/ml) resulted in a 3.5-fold increase of cell proliferation after hypoxia, LT at 1 ng/ml resulted in a 1.7-fold increase in cell proliferation under hypoxia. Similarly, SP (at a concentration of 10 ng/ml) increased cell proliferation after hypoxia in 2 fold (FIG. 17b). On the other hand, QF did not show increase in proliferation of endothelial cells after or under hypoxia treatment (FIG. 17c).

Figure 17D:
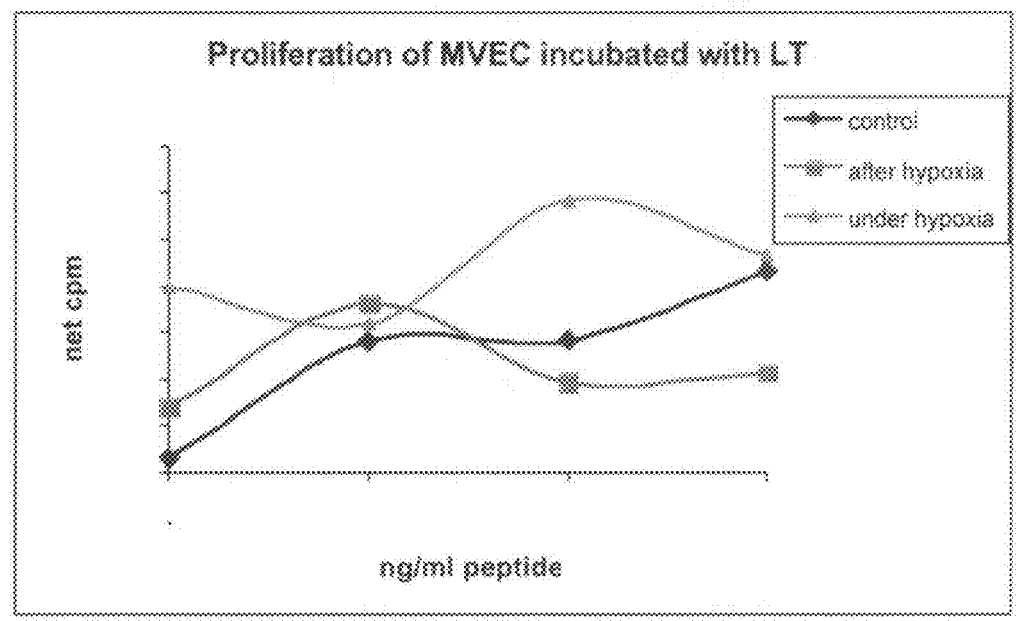
Figure 17E:
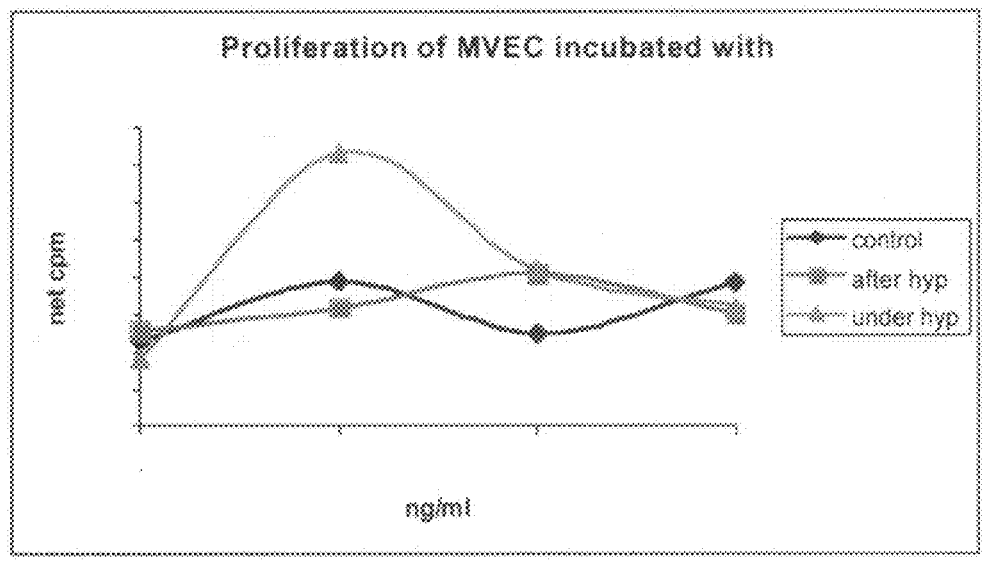
Figure 17F:
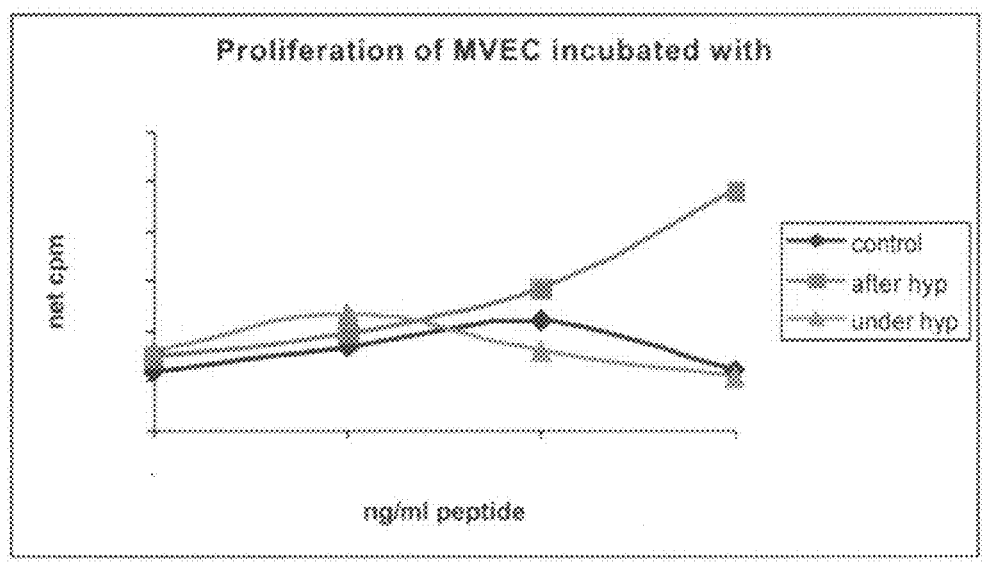

The effect of these synthetic peptides (QF, LT and SP) on the proliferation of MVECs under the same conditions was also tested. FIGS. 17d-e demonstrate a significant dose-dependent increase in [$^3$H]-Thymidine uptake in MVECs which were incubated with the peptides LT and SP after and under hypoxia. LT increased 1.7 fold MVECs proliferation after hypoxia at 1 ng/ml and at 10 ng/ml under hypoxia conditions (FIG. 17d). SP increased MVECs proliferation after hypoxia in 1.5 fold at 10 ng/ml and 1.9 fold under hypoxia conditions at 1 ng/ml (FIG. 17e). QF did not show increase proliferation of MVECs under hypoxic conditions compared to normoxic conditions (FIG. 17f).

Table 8, hereinbelow, summarizes the set of experiments testing the effect of the synthetic peptides of the present invention on HUVEC or MVEC cell proliferation under normoxia, following hypoxia or under hypoxia.

TABLE 8

The effect of synthetic peptides on cell proliferation
PROLIFERATION

|  | Normal | | After hypoxia | | Under hypoxia | |
| --- | --- | --- | --- | --- | --- | --- |
|  | HUVEC | MVEC | HUVEC | MVEC | HUVEC | MVEC |
| YR | ++ | ++ | − | − | + | + |
| LT | − | ++ | ++ | ++ | ++ | ++ |
| SP | − | − | ++ | ++ | ++ | ++ |

TABLE 8-continued

The effect of synthetic peptides on cell proliferation
PROLIFERATION

|  | Normal | | After hypoxia | | Under hypoxia | |
| --- | --- | --- | --- | --- | --- | --- |
|  | HUVEC | MVEC | HUVEC | MVEC | HUVEC | MVEC |
| QF | + | + | + | − | − | − |
| TR | ++ | ++ | − | − | − | − |
| VL | ++ | − | − | − | + | + |
| FGF | ++ | ++ | ++ | + | + | + |

Table 9, hereinbelow, summarizes the set of experiments testing the effect of the synthetic peptides of the present invention on HUVEC or MVEC cell migration.

TABLE 9

The effect of synthetic peptides on cell migration
MIGRATION

|  | Normal conditions | | Under hypoxia | |
| --- | --- | --- | --- | --- |
|  | HUVEC | MVEC | HUVEC | MVEC |
| None | − | − | − | − |
| YR | + | + | + | + |
| LT | +++ | +++ | − | − |
| SP | − | + | + | ++ |
| QF | ++ | ++ | + | ++ |
| TR | ++ | + | + | ++ |
| VL | + | + | ++ | + |
| FGF | ++ | ++ | + | + |

Tube formation assay after and under hypoxia treatment—The effect of synthetic peptides of the present invention on tube formation of ECs and MVECs was tested by their incubation on matrigel in the presence of LT, SP and QF peptides.

Addition of 10 ng/ml peptides QF under normoxic conditions, similar to the effect of VEGF or bFGF, resulted in a significant increase in tube formation in comparison to untreated ECs (FIGS. 13d and i). SP and LT under normoxic conditions did not induce tube formation (Data not shown). Peptide SP however, was effective only in tube formation under hypoxia conditions (FIG. 18a-e).

Table 10, hereinbelow, summarizes the set of experiments testing the effect of the synthetic peptides of the present invention on tube formation.

TABLE 10

The effect of synthetic peptides on tube formation
TUBE FORMATION

|  | Normal conditions | | After hypoxia | | Under hypoxia | |
| --- | --- | --- | --- | --- | --- | --- |
|  | HUVEC | MVEC | HUVEC | MVEC | HUVEC | MVEC |
| None | − | − | − | − | − | − |
| YR | ++ | ++ | − | − | ++ | ++ |
| LT | − | − | − | − | − | − |
| SP | − | − | − | − | ++ | ++ |
| QF | ++ | ++ | + | + | − | − |
| TR | − | − | − | − | − | − |
| VL | ++ | ++ | − | − | − | − |
| FGF | ++ | ++ | ++ | ++ | − | − |

EXAMPLE 5

Peptide-Induced In Vivo Angiogenesis

The synthetic peptides of the present invention were used to induce in vivo angiogenesis in a mouse ear model and rat or mice ischemic hind-limb models.

Materials and Experimental Methods

In Wivo angiogenesis in a mouse-ear model—Ear angiogenesis studies were a modification of an approach described previously (Pettersson, 2000). Synthetic peptides in a concentration of 1, 10 and 20 μg/15 μl per mouse were injected subcutaneously into the ears of nude mice and Balb/C mice. Contralateral ears were injected only with PBS. Digital photographs were obtained 2, 4, 6, and 20 days after injection. Two days after peptide inoculation, angiogenic effect of peptides could be observed.

Histological sections—Histological sections of the mouse-ears injected with the angiogenic peptides were performed by fixing tissues in 4% buffered formalin. Sections were embedded in paraffin blocks sectioned in 4 μm thick layers and stained with hematoxolin-eosin.

Rat ischemic hind-limb model and laser-Doppler imager analysis—A rat ischeric hind limb model was used for evaluation of the in vivo potential of angiogenesis induced by the selected synthetic peptides. Ischemia was created in the rat left hind limb by ligation the femoral artery. The right hind limb served as a control. A day after the operation each of the peptides was injected into two sites close to the ligation and one site distal to the ligation. Each rat was treated with each of the peptides in a total amount of 600 μg.

The blood flow was measured using a Laser Doppler Blood Flow analyzer (MoorLDI, Moor Instrument, Wilmington, Del.) at 2, 6, 9 and 13 days after peptides injections. The average perfusion of each limb was computed and blood flow was expressed as the ischemic (left)/control (right) blood flow ratio.

Mouse ischemic hind limb model—Ischemia was created in the mouse left hind limb by ligation of the femoral artery. The right hind limb served as control. A day after the operation each of the peptides was injected into one site close to the ligation and one site distal to the ligation. Each mouse was treated with each of the peptides in a total amount of 10 μg.

Physiological observations—Ischemic mice were evaluated for their ability to climb a ladder on day 1, 4, 7, and 10-post operation. The scoring system was as follows: 1—walk and climb; 2—walk and climb with some difficulty, 3—walk and cannot climb the ladder; 4—walk with difficulties and cannot climb the ladder.

Blood perfusion in ischemic mice—The percent of blood perfusion was measured using a Laser Doppler Imager (PeriMed, Sweden) at 14 and 19 days after peptides injections. The average percent perfusion of each limb was computed and expressed as the ischemic (left)/control (right) blood perfusion ratio.

Statistical and graphical methods—were performed as described in Example 1, hereinabove.

Experimental Results

In vivo angiogenesis in a mouse-ear model—Injection of the synthetic peptides or VEGF into the ears of nude mice and Balb/C mice resulted in increased number of blood vessels in the ears of mice injected with 10 μg of LT, YR, QF and SP (FIGS. 19b-e) or VEGF (FIG. 19a). Histological examination of stained sections of the ears revealed an increase in the number of blood vessels and the appearance of neo-vascularizations in peptide injected ears (FIGS. 20a-b, Table 11, hereinbelow).

TABLE 11

Blood vessels induced by peptide injection

| Peptide | Concentration | Days after inoculation | Number of blood vessels |
|---------|---------------|------------------------|-------------------------|
| FGF     | 3 ng/ear      | 5                      | 11                      |
| control | —             | 5                      | 7                       |
| VEGF    | 10 ng/ear     | 5                      | 17                      |
| control | —             | 5                      | 10                      |
| LT      | 10 μg/ear     | 5                      | 18                      |
| control | —             | 5                      | 13                      |
| SP      | 10 μg/ear     | 5                      | 15                      |
| control | —             | 5                      | 9                       |
| YR      | 10 μg/ear     | 5                      | 11                      |
| control | —             | 5                      | 12                      |
| TR      | 10 μg/ear     | 5                      | 15                      |
| control | —             | 5                      | 9                       |
| QF      | 10 μg/ear     | 5                      | 21                      |
| control | —             | 5                      | 15                      |
| VL      | 10 μg/ear     | 5                      | 14                      |
| control | —             | 5                      | 12                      |

Table 12, hereinbelow, summarizes the data obtained from a set of experiments testing the effect of the peptides of the present invention on in vivo ear angiogenesis.

TABLE 12

In vivo ear angiogenesis induced by AngioPeptides

|     | No. of mice | PBS Injected | Peptide/PBS |
|-----|-------------|--------------|-------------|
| PBS | 10          | 11.1         | 0.8         |
| LT  | 10          | 11.3         | 3           |
| SP  | 10          | 10           | 1           |
| YR  | 8           | 12.1         | 7.6         |
| TR  | 10          | 9.5          | 5.5         |
| VL  | 10          | 9.8          | 5.6         |
| QF  | 10          | 12.2         | 0.9         |
| FGF | 10          | 11.42        | 2.08        |

Table 12:
Synthetic peptides or PBS were injected to mice ears as described under Materials and Experimental Methods and the number of blood vessels were counted in PBS injected or the peptide injected ear.
Peptide/PBS = the ratio between the No. of blood vessels in the peptide-injected ear and the No. of blood vessels in the PBS-injected ear.

Laser-Doppler analysis in a rat ischemic hind-limb model—The blood flow of ischemic hind limb was measured after 600 μg peptide injection using a Laser Doppler Blood Flow analyzer (MoorLDI, Moor Instrument) at 4 time points (at days 2, 6, 9 and 13). The percent of median flux of the operated leg/control leg of rats treated with peptides was calculated for each peptide injected. Treatment of rats with the peptides QF and YR showed 112.5 and 108.2 percent increase of median flux of the ischemic leg/control leg, respectively (FIG. 21).

Physiological evaluation of the ability of the ischemic mice to climb a ladder were followed on day 1, 4, 7, and 10-post operation and the results are summarized in Table 13, hereinbelow.

TABLE 13

Physiological evaluation of ischemic mice following peptide injection

| Injection | Day 1 | Day 4 | Day 7 | Day 10 |
|-----------|-------|-------|-------|--------|
| PBS       | 3.07  | 3     | 2     | 2      |
| FGF       | 2.57  | 2     | 1     | 1      |
| YR        | 2.75  | 2.5   | 1.4   | 1      |
| TR        | 3.05  | 2.5   | 1.6   | 1.4    |

TABLE 13-continued

Physiological evaluation of ischemic mice following peptide injection

| Injection | Day 1 | Day 4 | Day 7 | Day 10 |
|---|---|---|---|---|
| QF | 2.83 | 2 | 1.6 | 1.2 |
| LT | 3.07 | 2.25 | 1.6 | 1.2 |
| VL | 2.75 | 2 | 1.6 | 1.4 |
| SP | 2.85 | 2.25 | 1.75 | 1.6 |

Table 13:
Physiological score of mice with hind limb ischemia as determined by the ability to clime a ladder.
Shown are the mean scores of 10 mice in each group.
The scoring system was as following:
1 - walk and climb;
2 - walk and climb with some difficulty;
3 - walk and cannot climb the ladder;
4 - walk with difficulties and cannot climb the ladder.

The results presented in Table 13, hereinabove, demonstrate the ability of the peptides of the present invention to prevent at least some of the physiological difficulties present in ischemic mice (e.g., climbing a ladder).

Injection of the synthetic peptides of the present invention increases blood perfusion in ischemic mice—To further test the potential of the synthetic peptides of the present invention to induce angiogenesis in vivo, the percent of blood perfusion was measured in ischemic mice using a Laser Doppler Imager (PeriMed, Sweden) at 14 and 19 days following peptides injections. The average percent perfusion of each limb was computed and expressed as the ischemic (left)/control (right) blood perfusion ratio. Significant differences were observed between the peptides (P=0.0102). As is shown in Table 14, hereinbelow, a significant increase in the percent of blood perfusion ratio was observed in mice injected with QF and YR.

TABLE 14

The blood perfusion ratio (in percentages) of the ischemic vs. control limbs

| Level | Number | Mean | Std Dev | Std Err Mean |
|---|---|---|---|---|
| FGF | 4 | 93.438 | 8.3423 | 4.171 |
| LT | 4 | 78.275 | 11.0320 | 5.516 |
| PBS | 9 | 82.436 | 7.2285 | 2.410 |
| QF | 4 | 112.222 | 22.4931 | 11.247 |
| SP | 8 | 84.478 | 15.2471 | 5.391 |
| TR | 8 | 86.006 | 16.4668 | 5.822 |
| VL | 8 | 95.560 | 12.2757 | 4.340 |
| YR | 4 | 104.349 | 22.0348 | 11.017 |

Altogether, these results strongly suggest the use of the synthetic peptides of the present invention, and especially, the QF and YR as angiogenic, anti-ischemic agents.

Example 6

A Conserved Sequence Motif (SEQ ID NO: 13) Supports the Angiogenic Function Attributed to the Peptides of the Present Invention Sequence analysis of the isolated peptides revealed a conserved amino acid sequence (SEQ ID NO: 27 or 32) which is shared by 3-4 of the peptides VL; QF, TR and possibly YR (see FIGS. 22a-c).

This sequence was found by the eMOTIF scan software (Biochemistry, Stanford University, Hypertext Transfer Protocol://dnadotstanforddotedu/emotif/emotif-scandothtml) to be shared with mouse vascular endothelial growth factor B precursor (Swiss-Prot Accession: VEGB_MOUSE), which has a very similar human homologue. The following peptide sequences YR (shared); LT and SP may belong to a different group. Interestingly these two groups of peptide were isolated under two different test conditions, while the first (VL, QF and TR) were isolated under normoxic conditions the second groups of peptides (YR, LT and SP) were selected under hypoxic conditions, suggesting that these two groups bind to different cellular determinants or with different affinities.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

REFERENCES CITED (Additional References are Cited in the Text)

1. Liekens S, De Clerk E, Netts J. Angiogenesis: regulators and clinical applications. Biochemical Pharmacology 61:253-270, 2001.

2. Lewis B, Flugelman M, Weisz A, Keren-Tal I, Schaper W. Angiogenesis by gene therapy: a new horizon for myocardial revascularization? Cardiovascular Research. 35:490-497, 1997.

3. Risau W. What if anything, is an angiogenic factor? Cancer Metastasis Review 15:149-151, 1996.

4. Monacci W T, Merill M J, Oldflield E H. Expression of vascular permeability factor/vascular endothelial growth factor in normal rat tissues. Am. J. Physiology 264:C1362-C1002, 1993.

5. Nomura M, Yamagishi S, Harada S, Hayashi Y, Yamashima T, Yamashita J and Yamamoto H. Possible participation of autocrine and paracrine vascular endothelial growth factors in hypoxia induced proliferation of endothelial cell and pericytes. J. Biological Chemistry 47:28316-28324, 1995.

6. Ikeda E, Achen M G, Breier G, Risau W. Hypoxia induced transcriptional activation and increased mRNA stability of vascular endothelial growth factor in C6 glioma cells. J. Biol. Chem. 270:19761-19766, 1995.

7. Shweiki D, Itin A, Soller D, Keshet E. Vascular endothelial growth factor induced by hypoxia may mediate hypoxia initiated angiogenesis. Nature, 359:843-845, 1992.

8. Wang G L, Jiang B, Rue E, Semenza G. Hypoxia inducible factor 1 is a basic helix loop helix pas heterodimer regulated by cellular oxygen tension. Proc. Natl. Acad. Sci. USA 92:5510-5514, 1995

9. Wang L, Xiong M, Che D, Liu S, Hao C, Zheng X The effect of hypoxia on expression of basic fibroblast growth factor in pulmonary vascular pericytes. J. Tongji Med Univ. 20:265-267, 2000.

10. Bainbridge J, Haiyan J, Bagherzadeh A, Selwood D, Ali R, Zachery L Introduction of a chemical constraint in a short peptide derived from human aFGF elicits mitogenic structural determinants. Biochemical and Biophysical Research Communications 302: 793-799, 2003.

11. Liu R, Enstrom A, Lam K. Combinatorial peptide library for immunobiology research. Experimental Hematology 31:11-30, 2003.

12. Giordano R., Cardo-Vila J., Lahdenrata, Pasqualini R, Arap W. Biopanning and rapid analysis of selective interactive ligands. Nature Medicine 7:1249-1253, 2001.

13. Hetian L, Ping A, Shumei S, Xiaoing L, Luowen H, Jian W, Lin M, Meisheng L, Junshan Y, Chengchao S. A novel peptide isolated from a phage display library inhibits tumor growth and metastasis by blocking the binding of vascular endothelial growth factor to its kinase domain receptor. J Biol Chem.277:43137-43142, 2002.

14. Conway E, Collen D, Carmeliet P. Molecular mechanisms of blood vessels growth. Cardiovascular Research. 40:507-521, 2001.

---

What is claimed is:

1. An isolated peptide comprising the amino acid sequence set forth in SEQ ID NO:6 or 10, the peptide being no more than 50 amino acids in length.

2. An isolated peptide consisting of the amino acid sequence set forth in SEQ ID NO:6 or 10.

3. The isolated peptide of claim 1, wherein the peptide is a cyclic peptide.

4. The isolated peptide of claim 1, wherein the peptide is a linear peptide.

5. A composition-of-matter comprising a peptide which comprises the amino acid sequence set forth in SEQ ID NO:6, wherein said peptide is no more than 50 amino acids in length, and an additional peptide which comprises the amino acid sequence set forth in SEQ ID NO:10, wherein said additional peptide is no more than 50 amino acids in length.

6. A composition-of-matter comprising a peptide which consists of the amino acid sequence set forth in SEQ ID NO: 6 and an additional peptide which consists of the amino acid sequence set forth in SEQ ID NO: 10.

7. A pharmaceutical composition comprising as an active ingredient the peptide of claim 1 and a pharmaceutically acceptable carrier or diluent.

8. The pharmaceutical composition of claim 7, wherein the peptide is a linear peptide.

9. The pharmaceutical composition of claim 7, wherein the peptide is a cyclic peptide.

10. A pharmaceutical composition comprising as an active ingredient the peptide of claim 2, and a pharmaceutically acceptable carrier or diluent.

11. A composition for targeting a drug to endothelial cells, the composition comprising the drug fused to a peptide consisting of the amino acid sequence set forth in SEQ ID NO:6 or 10.

12. A composition for targeting a drug to endothelial cells, the composition comprising the drug fused to the peptide of claim 1.

* * * * *